(12) United States Patent
Voelker et al.

(10) Patent No.: US 8,980,604 B2
(45) Date of Patent: Mar. 17, 2015

(54) MUTANT GLYCEROL DEHYDROGENASE (GLYDH) FOR THE PRODUCTION OF A BIOCHEMICAL BY FERMENTATION

(75) Inventors: Francois Voelker, Montrond les Bains (FR); Laurence Dumon-Seignovert, Pont du Chateau (FR); Isabelle Meynial-Salles, Fourquevaux (FR); Philippe Soucaille, Deyme (FR)

(73) Assignee: Metabolic Explorer, Saint Beauzire (FR)

( * ) Notice: Subject to any disclaimer, the term of this patent is extended or adjusted under 35 U.S.C. 154(b) by 301 days.

(21) Appl. No.: 13/387,337

(22) PCT Filed: Jul. 30, 2010

(86) PCT No.: PCT/EP2010/061129
§ 371 (c)(1),
(2), (4) Date: Jan. 26, 2012

(87) PCT Pub. No.: WO2011/012702
PCT Pub. Date: Feb. 3, 2011

(65) Prior Publication Data
US 2012/0135487 A1      May 31, 2012

Related U.S. Application Data

(60) Provisional application No. 61/229,775, filed on Jul. 30, 2009.

(30) Foreign Application Priority Data

Jul. 30, 2009   (EP) ..................................... 09166812

(51) Int. Cl.
| | | |
|---|---|---|
| C12N 9/04 | (2006.01) | |
| C12N 15/09 | (2006.01) | |
| C12P 7/18 | (2006.01) | |
| A61K 38/00 | (2006.01) | |

(52) U.S. Cl.
CPC ................. *C12P 7/18* (2013.01); *C12N 9/0006* (2013.01)
USPC ......... 435/190; 435/440; 435/285.1; 530/350

(58) Field of Classification Search
CPC combination set(s) only.
See application file for complete search history.

(56) References Cited

U.S. PATENT DOCUMENTS

| 2009/0136993 A1* | 5/2009 | Bridge et al. ................. 435/68.1 |
| 2009/0209001 A1* | 8/2009 | Schuermann et al. ........ 435/69.1 |
| 2010/0047878 A1* | 2/2010 | Nagai et al. .................... 435/107 |

FOREIGN PATENT DOCUMENTS

| EP | 1 762 621 | 3/2007 |
| WO | 98/25432 | 6/1998 |
| WO | WO2013052604 A1 * | 11/2013 ............... C12N 9/02 |

OTHER PUBLICATIONS

Altaras et al. (1999) Metabolic Engineering of a 1,2-Propanediol Pathway in *Escherichia coli*., Appl. Environ. Microbiol., vol. 65, No. 3, pp. 1180-1185.*
SEQ Alignment (2014) "SEQ ID No. 2 of US US20100047878", pp. 1-2.*
European Search Report Based on European Application EP 09 16 681 Dec. 15, 2009.
International Search Report Based on PCT/EP2010/061129 Mailed on Oct. 11, 2010.
Asnis et al.; "A Glycerol Dehydrogenase From *Escherichia coli*"; J. Biol. Chem.; vol. 203; pp. 153-159, (1953).
McGregor et al.; "Purification and Kinetic Characterization of a Monovalent Cation-Activated Glycerol Dehydrogenase From Aerobacter Aerogenes"; The Journal of Biological Chemistry; May 25, 1974; vol. 249; No. 10; pp. 3132-3139.
Nishise et al.; "Further Characterization of Glycerol Dehydrogenase From Cellulomonas SP. NT3060"; Agric. Biol. Chem.; 1984; vol. 48; No. 6; pp. 1603-1609.
Spencer et al.; "Isolation and Characterisation of the Glycerol Dehydrogenase From *Bacillus stearothermophilus*"; Biochimica Et Biophysica Acta, 994; 1989; pp. 279-279; Elsevier.
Ruzheinikov et al.; "Glycerol Dehydrogenase: Structure, Specificity, and Mechanism of a Family III Polyol Dehydrogenase"; Structure; 2001; vol. 9; pp. 789-802; Elsevier Science Ltd.
Mallinder et al.; "Cloning and Characterization of a Gene From *Bacillus stearothermophilus* Var. Non-Diastaticus Encoding a Glycerol Dehydrogenase"; Gene; 1991; vol. 110; pp. 9-16.
Truniger et al.; "Mapping and Cloning of GLDA, The Structural Gene of the *Escherichia coli* Glycerol Dehydrogenase"; Journal of Bacteriology; Mar. 1994; vol. 176; No. 6; pp. 1796-1800.
Kelley et al.; "D-1-Amino-2-Propanol:NAD+ Oxidoreductase"; The Journal of Biological Chemistry; Feb. 25, 1984; vol. 259; No. 4; pp. 2124-2129; The American Society of Biological Chemists, Inc.
Tang et al; "Purification and Properties of a Nicotinamide Adenine Dinucleotide-Linked Dehydrogenase That Serves an *Escherichia coli* Mutant for Glycerol Catabolism"; Jouranal of Bacteriology; Oct. 1979; vol. 140, No. 1, pp. 182-187.
Lee et al.; "Preparation of Optically Active 1,2-Diols and Alpha-Hydroxy Ketones Using Glycerol Dehydrogenase as Catalyst: Limits to Enzyme-Catalyzed Synthesis Due to Noncompetitive and Mixed Inhibition by Product"; J. Org. Chem; vol. 51; pp. 25-36; American Chemical Society, (1986).

(Continued)

*Primary Examiner* — Maryam Monshipouri
*Assistant Examiner* — Samuel Liu
(74) *Attorney, Agent, or Firm* — Miles & Stockbridge PC.

(57) ABSTRACT

The present invention concerns a method for the production of 1,2-propanediol, comprising culturing a microorganism modified for an improved production of 1,2-propanediol in an appropriate culture medium and recovery of the 1,2-propanediol which may be further purified wherein the microorganism expresses a glycerol dehydrogenase (GlyDH) enzyme the inhibition of which activity by NAD+ and/or its substrate and/or its product is reduced.
The present invention also relates to a mutant glycerol dehydrogenase (GlyDH) comprising at least one amino acid residue in the protein sequence of the parent enzyme replaced by a different amino acid residue at the same position wherein
 the mutant enzyme has retained more than 50% of the glycerol dehydrogenase activity of the parent enzyme and
 the glycerol dehydrogenase activity of the mutant GlyDH is less inhibited by NAD+ and/or by its substrate as compared to the parent enzyme and/or by its product as compared to the parent enzyme.

11 Claims, 5 Drawing Sheets

(56) References Cited

OTHER PUBLICATIONS

Subedi et al.; "Role of GLDA in Dihydroxyacetone and Methylglyoxal Metabolism of *Escherichia coli* K12"; FEMS Microbiol Lett 279; 2008; pp. 180-187; Federation of European Microbiology Societies: Blackwell Publishing Ltd.

Altaras et al.; "Metabolic Engineering of a 1,2-Propanediol Pathway in *Escherichia coli*"; Applied and Environmental Microbiology; Mar. 1999; vol. 65; No. 3; pp. 1180-1185; American Society for Microbiology.

Cooper; "Metabolism of Methylglyoxal in Microorganisms"; Ann. Rev. Microbiol.; 1984; vol. 38; pp. 49-68.

Totemeyer et al.; "From Famine to Feast: The Role of Methylglyoxal Production in *Escherichia coli*"; Molecular Microbiology; 1998; vol. 27; No. 3; pp. 553-562; Blackwell Science Ltd.

Ferguson et al.; "Methylglycoxal Production in Bacteria: Suicide or Survival"; Arch Microbiol; 1998; vol. 170; pp. 209-218; Spring-Verlag.

Misra et al.; "Glyoxalase III From *Escherichia coli*: A Single Novel Enzyme for the Conversion of Methylglyoxal Into D-Lactate Without Reduced Glutathione"; Biochem. J.; 1995; vol. 305; pp. 999-1003.

Cameron et al.; "Metabolic Engineering of Propanediol Pathways"; Biotechnol. Prog.; vol. 14; pp. 116-125; American Chemical Society and American Institute of Chemical Engineers, (1998).

Bennett et al.; "Microbial Formation, Biotechnological Production and Applications of 1,2-Propanediol"; Appl Microbiol Biotechnol; 2001; vol. 55; pp. 1-9; Springer-Verlag.

Ko et al.; "Conversion of Methylglyoxal to Acetol by *Escherichia coli* Adlo-Keto Reductases"; Journal of Bacteriology; Aug. 2005; vol. 187; No. 16; pp. 5782-5789; American Society for Microbology.

The Uniprot Consortium; 2008; Nucleic Acids Res.; vol. 36; pp. D190-D195.

Guldener et al.; "A New Efficient Gene Disruption Cassette for Repeated Use in Budding Yeast"; Nucleic Acids Research; 1996; vol. 24; No. 13; pp. 2519-2524; Oxford University Press.

Schiestl et al.; "High Efficiency Transformation of Intact Yeast Cells Using Single Stranded Nucleic Acids as a Carrier"; Curr Genet; 1989; vol. 16; pp. 339-346; Spinger-Verlag.

Shevchuk et al.; "Construction of Long DNA Molecules Using Long PCR-Based Fusion of Several Fragments Simultaneously"; Nucleic Acids Research; 2004; vol. 32; No. 2; Oxford University Press.

Liese et al.; "Enzymatic Resolution of 1-Phenyl-1,2-Ethanediol by Enantioselective Oxidation: Overcoming Product Inhibition by Continuous Extraction"; Biotechnology and Bioengineering; 1996; vol. 51; pp. 544-550, John Wiley & Sons, Inc.

Rasko et al.; "The Pangenome Structure of *Escherichia coli*: Comparative Genomic Analysis of *E. coli* Commensal and Pathogenic Isolates"; J. Bacteriol.; Database Uniprot; 2008, vol. 190; pp. 6881-6893; XP002557327.

Touchon et al.; "Organised Genome Dynamics in the *Escherichia coli* Species Results in Highly Diverse Adaptive Paths"; Plos Genet. Database Uniprot; 2009; vol. 5; pp. E1000344-E1000344; XP002557328.

* cited by examiner

```
            1
EGSA_PICTO  ----MNFNKI KSMHF--PSD VYIGH----- --DAILNIGS VVSKFLKSGE VLLIT-GENT -YNIAGKKVL
EGSA_THEVO  ----MEFQKY RTMHF--PRD VYIGH----- --DVLNRVLD VVDQNSRTRD VIIVT-GNTT -YELAGKKIV
EGSA_THEAC  ----MEFQKF RTMHF--PRD VYIGH----- --DVLEHIVD VVGENSRNKN AIIVS-GDLT -YELAGRKVH
EGSA_PYRAE  ------MKQL ESFQI--PRI VIFGP----- --GAILKTPL VVSELK-AGR ILVIS-GKSA -TTAYANQVA
EGSA_METJA  ---------- MIIVT--PRY TIIED----- --GAINKIEE ILKKLNLKNP LVIT--GKNT ----------
EGSA_AERPE  -----MYTSF HRIDL--PRT IVVGG----- --GVLDKAGG YVSGVAQRGS YVLVVSGPTV -SSKYFERLR
EGSA_HALSA  -----MFEKS TWIRL--PRN VVVGH----- --GVLDDAVE VVRDTHLTGR PLVVT-SPTP -KTVAAENVV
EGSA_SULSO  -----MNVKE HVISL--PRR VFVGH----- --DIVYDISI YFSQLGVTPP FLIVT-GTKY TKKIADKVIE
EGSA_SULAC  MLYKTVEIKE HIINL--PKH IYTGY----- --GILDNFRN YLQTLNLFQP FLVIT-GPVI HQEIFSKRIE
EGSA_SULTO  -----MELKE HIIDL--PKK VYIGY----- --DIIDNIKE YILSLNLSGP FLIVT-GPLV -RKIITDKII
EGSA_METMA  MKLTINKNSA KWMQL--PRD VLVGH----- --GVLEEVGD VCRDLKLKGN ALIVT-GSTT -QDVAGKRVS
EGSA_METAC  MKLTINKNSA KWMQL--PRD VLVGH----- --GVLEEIGD VCRDLKLKGN ALIVT-GNTT -RDVAGKRVS
EGSA_METKA  -----MSVPK KRMQL--PRE VVVGS----- --NVLPEVPK LLRSVGVPDG VVAVFSGRTT -MKIAGNEVA
EGSA_PYRKO  ------MERRI HLMQL--PRE VLLGE----- --NLTGEVVS VAKRIGLTGK ALVIY-GPKT -KEIAGRDVE
EGSA_PYRFU  ---------M HIMEF--PRE VILGK----- --NVISETVN VAKRLSFSSP VLVVY-GPKT -KEIAGKDVE
EGSA_PYRHO  ---------M HLMEF--PRE VILGK----- --NLIQEINN VIKRLKLGSP GLVVY-GPIT -KKIAGSNVE
EGSA_PYRAB  ---------M HLMEF--PRE VILGK----- --NLVPEVNN VIKRLKLESP GLVVY-GPVT -KKIAGESVK
GLDA_BACST  ------MAAE RVFIS--PAK YVQGK----- --NVITKIAN YLEGIG--NK TVVIA-DBIV -WKIAGHTIV
GLDA_CITFR  --------ML KVIQS--PAK YLQGP----- --DASTLFGQ YAKNLA--DS FFVIA-DDFV -MKLAGEKVL
GLDA_ECOL6  --------MD RIIQS--PGK YIQGA----- --DVINRLGE YLKPLA--ER WLVVG-DKFV -LGFAQSTVE
GLDA_PSEPU  --------MD RAIQS--PGK YVQGA----- --DALQRLGD YLKPLA--DS WLVIA-DKFV -LGFAEDTIR
YBDH_ECOLI  ---------- -MPHN--PIR VVVGPANYFS HPGSFNHLHD FFTDEQLSRA VWIY--GKRA -IAAAQTKLP
Y1167_SYNY3 ----MAPSIS PVTQP--LVS MAIAPTVVIR --SALAKAGE HLQKLG--SK GLVVT-GSHS -AELGEKSLQ

71
EGSA_PICTO  SNLND--FDV NVII-ASR-A TRDSIKSEE SLKNRRSGIV LGVGGGSKID IAKKIAY--- ----------
EGSA_THEVO  EILASSPYEV HLS--FAGEA NYENLKKIEE ETNDVNAGII IGVGGGTKID LAKKLAY--- ----------
EGSA_THEAC  DLLSTYGYEV HVF--LAGNA NYDTLERIEY ESLDIQAGIV IGVGGGAKID LAKKLAF--- ----------
EGSA_PYRAE  QLLSNYSVDV ---------V RYNEVD---- -LSKSSYDLV IGVGGGRFID MAKYSC---- ----------
EGSA_METJA  KKYCRFFYDI VYYD-----E ILNNLEIELK KYTAYDC--V IGIGGGRSID TGKYLAY--- ----------
EGSA_AERPE  ASLEAEGLTV GLKI-IRD-A TVETAEEVAR EALESRIEVV AGLGGGKSID VAKYASK--- ----------
EGSA_HALSA  AQFEAVGDDP AVVV-VEE-A TFNSVERVLG EAEAVDPGYL VGVGGGKAID IAKLASD--- ----------
EGSA_SULSO  NLPKDAKYEV --VE-IDS-A TLJDDVYMVEE VIKRISPSLL LGIGGGKVID VTKYAF---- ----------
EGSA_SULAC  EHIKDFKYEV --VI-VNK-S DLSEAEKVED IARQKGIKTI LGVGGGTVID IAKFTAY--- ----------
EGSA_SULTO  ENFKDESVEV VEVK-I---A SIDEVNKVEE MAKGSRINTI IGVGGGNIID VAKYVAY--- ----------
EGSA_METMA  RLLEDAGNST ETVL-TCR-A TMEEVDKLME LALNTEATFL LGVGSGRSID LAKLAST--- ----------
EGSA_METAC  TLLENAGSST EMVL-TCR-A TMEEVDKIMQ KASETGATFL LGIGSGRSID LAKLAST--- ----------
EGSA_METKA  DHLEEAGYQT SPVI-VKG-S TGDDVKKALE ALDEIDADVV AAVGGGKVID VAKVASY--- ----------
EGSA_PYRKO  DAIKSA-YEV SSLT-IRKGA TMEEVERTIE KIKDEGIGWV IAVGGGSTID VAKLSSF--- ----------
EGSA_PYRFU  RVLKEE-FDV HSVI-VKE-A TINEVEKVEG IIRDNKVKWA IAVGGGTIID VTKLASY--- ----------
EGSA_PYRHO  KIVKEE-FEV YSIT-VKE-A HINEVERVIS KIRDKGIKWA IAVGGGSIID VTKLASF--- ----------
EGSA_PYRAB  KAIRDE-FDV YSIT-VKK-A HIGEVEKVEA KIRDYNIKWA IAVGGGSIID VTKLASY--- ----------
GLDA_BACST  NELKKGNIAA EEVV-FSGEA SRNEVERIAN IARKAEAAIV IGVGGGKTLD TAKAVAD--- ----------
GLDA_CITFR  NGLHSHDISC HAER-FNGEC SHIEINRLIA ILKQHGCRGV VGIGGGKTLD TAKAIGY--- ----------
GLDA_ECOL6  KSFKDAGLVV EIAP-FGGEC SQNEIDRLRG IAETAQCGAI LGIGGGKTLD TAKALAH--- ----------
GLDA_PSEPU  QSLSKAGLAM DIVA-FNGEC SQGEVDRLCQ LATQNGRSAI VGIGGGKTLD TAKAVAF--- ----------
YBDH_ECOLI  PAFGLPGAKH --IL-FRGHC SESDVQQLAA ESGD-DRSVV IGVGGGALLD TAKALAR--- ----------
Y1167_SYNY3 TLQKNYGLTL PLAS-YLPDC AESSLEQLRR RVHQEQPDFI LGIGGGKALD TAKLLAH--- ----------

141
EGSA_PICTO  -------DLG IPFISVPTTP SHDGIASPRA SIY---DGKS VYSEEATM-P SAIVADTSIM VLAPYRYVAA
EGSA_THEVO  -------DKN LPFISIPTSP SHDGIASPRA SLR---RNGI SYSEEGAM-P IGVIADTSVM IKAPYRYLAA
EGSA_THEAC  -------DRK LPFVSVPTAP SHDGIASPRA SLR---RNGI SYSEEGAM-P IGVIADTAIM IKAPYRYLAA
EGSA_PYRAE  -------VHK KPLVVIPTAA SHDGIASPYV S-YTLSQKLQ TYGKIVAS-P VAIIADTSVI LSAPSRLLKA
EGSA_METJA  -------KLG IPFISVPTTA SNDGIASPIV SIR------- QPSFMVDA-P IAIIADTEII KKSPRRLLSA
EGSA_AERPE  -------RAG SVFVSIPTVA SHDGITSPFS SLK---GFDK PISRPAKA-P EAIIIDVDVI AEAPRRYNIA
EGSA_HALSA  -------HLN VGFVSIPTAA SHDGIVSGRG SVP---EGDT RHSVSAAP-P LAVIADTGVI ADAPWELTTA
EGSA_SULSO  -------RNS LEFVSIPTSP SHDGITSPFA SIK---GLQK PVSVKAKE-P LAIIADIEIL SLSPRRLINA
EGSA_SULAC  -------KID REFISIPTSP SHDGITSPFA AIK---GLGK PISIKAKE P LAIISDVEIL ASAPRRLINA
EGSA_SULTO  -------RIG KEFVSLPTAP SHDGITSPFA SIK---GLGK PTSVKAKG-P IAIIADINVL ASAPRRLINA
EGSA_METMA  -------RLE IPFISVPTAA SHDGIASSRA SVI---DNGK NASIQAQA-P LAVIADTEII SAAPYRFLAA
EGSA_METAC  -------RLE IPFVSVPTAA SHDGIASSRA SII---DNGK NASVQAQA-P IAVVADTEII SAAPFRFLVA
EGSA_METKA  -------RRG IPFISVPTSA SHDGIASPFA SIR---REGR PYSEPAQA-P LAILADIEVI REAPERLIRA
EGSA_PYRKO  -------KTG VPPISFPTTA SHDGIASANA SIK---DLGS KTSVKAVP-P VAVIADVKVI KTAPYRYLAA
EGSA_PYRFU  -------RAG IPFVSFPTTA SHDGIASANA SIK---GLGT KTSIKARP-P VAVIADIRII KSAPRRYLAA
EGSA_PYRHO  -------KMG IPPISFPTTA SHDGIASANA SIK---GLNV KTSIKAKP-P IAVIADIDVI KTAPKRYLAA
EGSA_PYRAB  -------RSG IPFISFPTTA SHDGIASANA SIR---GIEA KTSIKARP-P IAVIADIEVI KTAPRRYLAA
GLDA_BACST  -------ELD AYIVIVPTAA STDAPTSALS VIYSDDGVFE SYRFYKKN-P DLVLVDTKII ANAPPRLLAS
GLDA_CITFR  -------YQK LPVVIPTIA STDAPTSALS VIYTEAGEFE EYLIYPKN-P DMVVMDTAII AKAPVRLLVA
GLDA_ECOL6  -------FMG VPVAIAPTIA STDAPCSALS VIYTDEGEFD RYLLLPNN-P NMVIVDTKIV AGAPARLLAA
GLDA_PSEPU  -------FQK VPVAVAPTIA STDAPCSALS VLYTDEGEFD RYLMLPTN-P ALVVVDTAIV ARAPARLLAA
YBDH_ECOLI  -------RLG LPFVAVPTIA ATCAAWTPLS VWYNDAGQAL HYEIFDDA-N FMVLVEPEII LNAPQQYLLA
Y1167_SYNY3 -------QTQ LAIATVPTSA ATCAGWTALA NVYSETGAFR YDVALDRC-P DLLIVDYELI QRAEPRLLVA
```

Fig. 1A

```
           211
EGSA_PICTO   GAADVISNIT AVLDW--KLA NRLKGEEFS- STAAVMSEYA GRELIERSSM IQP-GLEESI W----LVTKQ
EGSA_THEVO   GAADVISNIS AVKDW--KLA HRLRGEEFS- SSAAAMSEYS AQEVISQVGE IRK-YDESSV W----LVTKN
EGSA_THEAC   GAADVISNLS AVKDW--KLA HRLKGEEFS- SSAAAMSEYS AQEVLSQINE IKK-YEESSV W----LVTKN
EGSA_PYRAE   GIGDLLGKII AVRDW--QLA EYAAHLAVTS YKIAATNARR IRNPTREEDV R----VLVKA
EGSA_METJA   GMGDIVSNIT AVLDW--KLA YKEKGEKYS- ESSAIFSKTI AKELISY--- VLNSDLSEYH N----KLVKA
EGSA_AERPE   GFGDLIGKYT AVLDW--RLA HKLRLEYYG- EYAASLALLS AKHVSQYAEE IAL-GTREGY R----VLLEA
EGSA_HALSA   GCADIISNYT AVKDW--KLA NRLQHVPYS- EYAGALSQMT AEMLVDNAAN IKF-ELEESA W----VVVKA
EGSA_SULSO   GIGDTIGKII AVRDW--KLA AKLRGEYYG- DYTASLALMS AKHAFQCTKI INK-DIKYGV R----MLMEA
EGSA_SULAC   GIGDTLGKIT AVRDW--RLA HKLRGEYYG- DYTASLALMS ARHALSCTKI INK-DIRAGV R----VLTEA
EGSA_SULTO   GIGDTIGKIT AVRDW--QLA AKLRGEYYG- DYTASLALMS AKHALSCAKI LDK-DVRAGV R----VLTEA
EGSA_METMA   GCGDIISNYT AVLDW--ELA SRLRNEYFG- EYAAALSRMA ARVVIENADS IKF-DHETSA R----LVVKA
EGSA_METAC   GCGDIISNYT AVLDW--ELA SRLRNEYFG- EYAAALSRMA ARVVIENADS IKF-EHETSA R----LVVKA
EGSA_METKA   GVGDVVSNVT AVKDW--RLA HRLRNEPYS- EYASSLSLMA ARIVMKNAKF IGK-LLPEGI K----KLVQA
EGSA_PYRKO   GVGDTISNLT AVRDW--QLA HRIKGEYYS- EYAASLSLMS AKMVMRNADI IRL-GNEESV R----KVIKA
EGSA_PYRFU   GVGDISNIT AVRDW--KLA HKIKGEYFS- EYAAALSLMS AKMVMRDAEI IRI-GDDEGV R----KVVKA
EGSA_PYRHO   GVGDIVSNIT AVRDW--KLA HKLKGEYFS- EYAASLSLMS AKMVIRDAEI IRI-GQDEGI R----KVVKA
EGSA_PYRAB   GVGDIVSNIT AVRDW--KLA HKLKGEYFS- EYAAALSLMS AKMVIRDAEI IRL-GNDEGV R----KVIKA
GLDA_BACST   GIADALATWV EARSVIKSGG KTMAGGIPT- IAAEAIAEKC EQTLFKYGKL AYESVKAKVV T----PALEA
GLDA_CITFR   GMGDALSTWF EAKACYDARA TSMAGGQST- VAALSLARLC YDTLLAEGEK ARFAAQAGVV T----DALER
GLDA_ECOL6   GIGDALATWF EARACSRSGA TTMAGGKCT- QAALALAELC YNTLLEEGEK AMLAAEQHVV T----PALER
GLDA_PSEPU   GIGDALATWF EARAASRSSA ATMAGGPAT- QTALNLARFC YDTLLEEGEK AMLAVQAQVV T----PALER
YBDH_ECOLI   GIGDTLAKWY EAV----VLA PQPETLPLTV RLGINNAQAI RDVLLNSSEQ ALSDQQNQQL TQSFCDVVDA
Y1167_SYNY3  GIGDAIAKWY EA-----SVS SGQSSDTFT- VAAVQQARIL RDILFQKSAE ALAQPGSETW R----EVVDA

281
EGSA_PICTO   ILASGAAMAI AGSSRPASGS EHLFSHAIEI LGPG-----S SIH------- -----GEQCA -MGSLISMYL
EGSA_THEVO   ILASGTAMAI AGNSRPGSGS EHLFAHALEA AGVN-----N MLH------- -----GEMCA -MGTTVSLYL
EGSA_THEAC   ILASGTAMAI AGNSRPGSGS EHLFAHALEA AGVE-----N MLH------- -----GEMCA -MGTVISMYL
EGSA_PYRAE   LIGCGVAMGI AGSSRPCSGS EHLFAHAIEL RLQEESS--E AVH------- -----GELVA -LGTIIMAYL
EGSA_METJA   LVGSGIAIAI ANSSRPASGS EHLFSHALDK LKEEYNLNIN SLH------- -----GEQCG -IGTIMMSYL
EGSA_AERPE   LVSSGTRPASGS EHLFAHALHI VARN-----K PLH------- -----GEAVG -VGTIMMAYL
EGSA_HALSA   LVSSGVAMSI ADSSRPASGS EHLFSHQLDR IAPG-----K ALH------- -----GHQVG -VGSILAEYL
EGSA_SULSO   LISSGVAMGM AGSTRPASGS EHLFAHAVEL IHPE-----G ILH------- -----GELVG -LGTIIMAYL
EGSA_SULAC   LISSGVAMGM AGSTRPASGS EHLFAHAIEL LYPN-----L GLH------- -----GELVA -LGTIMMAYI
EGSA_SULTO   LISSGVAMGM AGSTRPASGS EHLFAHAIEI LYPD-----L ALH------- -----GELVA -LGTILMAYI
EGSA_METMA   LVSNGVAMSI AGSSRPASGS EHMFSHALDR IAPK-----A ALH------- -----GEQCG -VGTIMMMYL
EGSA_METAC   LVSNGVAMSI AGSSRPASGS EHMFSHALDR IAPK-----P ALH------- -----GEQCG -VGTIMMMYL
EGSA_METKA   LISGGVAMSI AGSSRPCSGS EHLFSHALDV IAER-----P ALH------- -----GEQCG -VGTIIMEYL
EGSA_PYRKO   LISTGVAMSI AGSSRPASGA EHLFSHALDM LLDK-----P ALH------- -----GEQTG -LGTIIMAYL
EGSA_PYRFU   LISSGVAMSI AGSSRPASGA EHLFSHALDL LLEK-----P ALH------- -----GEQTG -IGTIIMAYL
EGSA_PYRHO   LISSGVAMSI AGSSRPASGA EHLFSHALDM LLDK-----P ALH------- -----GEQTG -IGTIIMAYL
EGSA_PYRAB   LISSGVAMSI AGSSRPASGA EHLFSHALDL LLDK-----P ALH------- -----GEQTG -IGTIIMAYL
GLDA_BACST   VVEANTLLSG LGFESGGLAA AHAIHNGFTA LEGEIH---H LTH------- -----GEKVA -FGTLVQLAL
GLDA_CITFR   IVEANTYLSG IGFESSGLAG AHAIHNGFTI LEECH----H LYH------- -----GEKVA -FGTLAQLVL
GLDA_ECOL6   VIEANTYLSG VGFESGGLAA AHAVHNGLTA IPDAH----H YYH------- -----GEKVA -FGTLTQLVL
GLDA_PSEPU   IVEANTYLSG VGFESGGVAA AHAVHNGLTA VAETH----H FYH------- -----GEKVA -FGVLVQLAL
YBDH_ECOLI   IIAGGGMVGG LGDRFTRVAA AHAVHNGLTV LPQTE----K FLH------- -----GTKVA -YGILVQSAL
Y1167_SYNY3  SLLMAGVIGG LGGANCRTVA AHAVHNGLTQ LPQAH----H ALH------- -----GEKVA -YGILVQLRL

351
EGSA_PICTO   HG----GDW- ----ELLKNT YRKIGLNTRA ESYGIGREVA IKALSIAHRI RPSRYTILG- ESDLSYNVAE
EGSA_THEVO   HD----DNW- ----QKIRDV FESLGVSVKA RDYGLKEEVV IEALRRAHAI RPERYTILG- ESDMSYDAAV
EGSA_THEAC   HD----ENW- ----QQIKEA FDNLGISIRS RDYGIEDEIV INALRTAHAI RPERYTILG- ESDMSYDAAV
EGSA_PYRAE   HG----INW- ----RRIKKI AEIVGLPTTL KQAGIDADMA VEALTTAHAL RPDRYTILG- -NGLSREAAR
EGSA_METJA   HE-KENKKLS G-LHEKIKMS LKKVDAPTTA KELGFDEDII IEALTMAHKI R-NRWTILR- -DGLSREEAR
EGSA_AERPE   HG----KNW- ----RRIRGL LKTVGAPTNA KELGVEDDEV VEALTIAARI RPERYTILG- EKGLTREAAE
EGSA_HALSA   HS-GQEGQW- ----MAVRDA LASLDAPTTA DELGVADDEV LAALTSAHEI R-DRYTILG- -GGISEVAAR
EGSA_SULSO   HG----INW- ----KIIRNF LKKIGFPVKA KDLGLSDEEV IKALTIAHTI RPERYTILG- DRGLTWSSAE
EGSA_SULAC   HG----INW- ----RRIRRA MKKIGLPVKA KQIGIPDEGI IKALTIAHTI RPERYTILG- DRGLTWSESAE
EGSA_SULTO   HG----INW- ----KKIKKA MKKVGLPTKA KQLGIPDEII IKALTIAHTI RPERYTILG- DRGLTWEAAE
EGSA_METMA   HG----GNW- ----QEIRDA LKKIGAPTNA EELGIEDKYI IEALLQAHSI RPDRYTILG- -NGLTLSAAE
EGSA_METAC   HG----GNW- ----QEIRDA LKKIGAPTTA VEALLHAHSI RPDRYTILG- -NGLTPSAAE
EGSA_METKA   HG----GNW- ----REIRET LETAGAPTTA EDLGVSDEEI IEALCRAHKI RPDRYTILG- DKGLTREAAR
EGSA_PYRKO   HG----MKW- ----ERVRET LKRVGAPTNA YELGIDPEVI IEALTIAHTI RPRRYTILG- KDGLTREAAR
EGSA_PYRFU   HG----INW- ----RKIKET LQKVGAPTTA YELGVDPEII IEALTIAHTI RPERYTILG- RDGLTREAAE
EGSA_PYRHO   HG----INW- ----KKIRDT LKIVGAPTTA YELGIDPEII IEALTIAHTI RPERYTILG- KEGITREAAE
EGSA_PYRAB   HG----INW- ----RKIKET LKTVGAPTSA YELGIDPEII IEALTIAHKI RPERYTILG- KEGLTREAAE
GLDA_BACST   EE-HSQQEI- ----ERYIEL YLSLDLPVTL EDIKLKDASR EDILKVAKAA TAEGETIHN- AFNVTADDVA
GLDA_CITFR   QN-SPMEEI- ----ETVLNF CQKVGLPVTL AEMGVKDDID GKIMAVAKAT CAEGETIHNM PFSVTPESVH
GLDA_ECOL6   EN-APVEEI- ----ETVAAL SHAVGLPITL AQLDIKEDVP AKMRIVAEAA CAEGETIHNM PGGATPDQVY
GLDA_PSEPU   EN-ASNAEM- ----QEVMSL CHAVGLPITL AQLDITEDIP TKMRAVAELA CAPGETIHNM PGGVTVEQVY
YBDH_ECOLI   LG--QDDVL- ----AQLTGA YQRFHLPTTL AELEVDINNQ AEIDKVIAHT LRPVESIHYL PVTLTPDTLR
Y1167_SYNY3  EELVSGNQLA ATARRQLLSF YDEIGLPKTL QDLGLGRISL EELRQTAEFT CLPNSDIHRL PFTVTPETLM
```

Fig. 1B

```
              421
EGSA_PICTO    RILSITGII-  ----------  ------
EGSA_THEVO    KALELTGII-  ----------  ------
EGSA_THEAC    KALELTGII-  ----------  ------
EGSA_PYRAE    RALEDTELI-  ----------  ------
EGSA_METJA    KLAEETGVI-  ----------  ------
EGSA_AERPE    ALARKTGVI-  ----------  ------
EGSA_HALSA    EAASRTGVI-  ----------  ------
EGSA_SULSO    KIARVTKIID  ----------  ------
EGSA_SULAC    KIARETGVIS  ----------  ------
EGSA_SULTO    KIAKETGIID  ----------  ------
EGSA_METMA    KVARITKVIN  ----------  ------
EGSA_METAC    KVARITKVIS  ----------  ------
EGSA_METKA    RAAEETGVIQ  ----------  ------
EGSA_PYRKO    KAAKITGVI-  ----------  ------
EGSA_PYRFU    RAAKITGVI-  ----------  ------
EGSA_PYRHO    KAAKITGVI-  ----------  ------
EGSA_PYRAB    KAAKITGVI-  ----------  ------
GLDA_BACST    DAIFAADQYA  KAYKEKHRK-  ------
GLDA_CITFR    AAILTADLLG  QQWLAR----  ------
GLDA_ECOL6    AALLVADQYG  QRFLQEWE--  ------
GLDA_PSEPU    GALLVADQLG  QHFLEF----  ------
YBDH_ECOLI    AAFKKVESFK  A---------  ------
Y1167_SYNY3   AAMVSTLVEE  QGTRQLFAQI  QDNSGL
```

Fig. 1C

SEQUENCE LISTING

<160> NUMBER OF SEQ ID NOS: 69

<210> SEQ ID NO 1
<211> LENGTH: 367
<212> TYPE: PRT
<213> ORGANISM: Escherichia coli

<400> SEQUENCE: 1

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Thr
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 2
<211> LENGTH: 367
<212> TYPE: PRT
<213> ORGANISM: Escherichia coli

<400> SEQUENCE: 2

```
Met Asp Arg Ile Ile Gln Ser Pro Gly Lys Tyr Ile Gln Gly Ala Asp
1               5                   10                  15
Val Ile Asn Arg Leu Gly Glu Tyr Leu Lys Pro Leu Ala Glu Arg Trp
            20                  25                  30
Leu Val Val Gly Asp Lys Phe Val Leu Gly Phe Ala Gln Ser Thr Val
        35                  40                  45
Glu Lys Ser Phe Lys Asp Ala Gly Leu Val Val Glu Ile Ala Pro Phe
    50                  55                  60
Gly Gly Glu Cys Ser Gln Asn Glu Ile Asp Arg Leu Arg Gly Ile Ala
65                  70                  75                  80
Glu Thr Ala Gln Cys Gly Ala Ile Leu Gly Ile Gly Gly Gly Lys Thr
                85                  90                  95
Leu Asp Thr Ala Lys Ala Leu Ala His Phe Met Gly Val Pro Val Ala
            100                 105                 110
Ile Ala Pro Thr Ile Ala Ser Asn Asp Ala Pro Cys Ser Ala Leu Ser
        115                 120                 125
Val Ile Tyr Thr Asp Glu Gly Glu Phe Asp Arg Tyr Leu Leu Leu Pro
    130                 135                 140
Asn Asn Pro Asn Met Val Ile Val Asp Thr Lys Ile Val Ala Gly Ala
145                 150                 155                 160
Pro Ala Arg Leu Leu Ala Ala Gly Ile Gly Asp Ala Leu Ala Thr Trp
                165                 170                 175
Phe Glu Ala Arg Ala Cys Ser Arg Ser Gly Ala Thr Thr Met Ala Gly
            180                 185                 190
Gly Lys Cys Thr Gln Ala Ala Leu Ala Leu Ala Glu Leu Cys Tyr Asn
        195                 200                 205
Thr Leu Leu Glu Glu Gly Glu Lys Ala Met Leu Ala Ala Glu Gln His
    210                 215                 220
Val Val Thr Pro Ala Leu Glu Arg Val Ile Glu Ala Asn Thr Tyr Leu
225                 230                 235                 240
Ser Gly Val Gly Phe Glu Ser Gly Gly Leu Ala Ala His Ala Val
                245                 250                 255
His Asn Gly Leu Thr Ala Ile Pro Asp Ala His His Tyr Tyr His Gly
            260                 265                 270
Glu Lys Val Ala Phe Gly Thr Leu Thr Gln Leu Val Leu Glu Asn Ala
        275                 280                 285
Pro Val Glu Glu Ile Glu Thr Val Ala Ala Leu Ser His Ala Val Gly
    290                 295                 300
Leu Pro Ile Thr Leu Ala Gln Leu Asp Ile Lys Glu Asp Val Pro Ala
305                 310                 315                 320
Lys Met Arg Ile Val Ala Glu Ala Cys Ala Glu Gly Glu Thr Ile
                325                 330                 335
His Asn Met Pro Gly Gly Ala Thr Pro Asp Gln Val Tyr Ala Ala Leu
            340                 345                 350
Leu Val Ala Asp Gln Tyr Gly Gln Arg Phe Leu Gln Glu Trp Glu
        355                 360                 365
```

<210> SEQ ID NO 3

```
<211> LENGTH: 24
<212> TYPE: DNA
<213> ORGANISM: Artificial Sequence
<220> FEATURE:
<223> OTHER INFORMATION: Oligonucleotide

<400> SEQUENCE: 3
caccatggac cgcattattc aatc                                      24

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide

<400> SEQUENCE: 4
ttattcccac tcttgcagga aacgc                                     25

<210> SEQ ID NO 5
<211> LENGTH: 45
<212> TYPE: DNA
<213> ORGANISM: Artificial Sequence
<220> FEATURE:
<223> OTHER INFORMATION: Oligonucleotide

<400> SEQUENCE: 5
gacaccaaaa tcgtcgctgg cacacctgca cgtctgctag cggcg               45

<210> SEQ ID NO 6
<211> LENGTH: 45
<212> TYPE: DNA
<213> ORGANISM: Artificial Sequence
<220> FEATURE:
<223> OTHER INFORMATION: Oligonucleotide

<400> SEQUENCE: 6
cgccgctagc agacgtgcag gtgtgccagc gacgattttg gtgtc               45

<210> SEQ ID NO 7
<211> LENGTH: 48
<212> TYPE: DNA
<213> ORGANISM: Artificial Sequence
<220> FEATURE:
<223> OTHER INFORMATION: Oligonucleotide

<400> SEQUENCE: 7
gcgatcgcac cgactatcgc ctctaacgat gcaccctgca gcgcattg            48

<210> SEQ ID NO 8
<211> LENGTH: 48
<212> TYPE: DNA
<213> ORGANISM: Artificial Sequence
<220> FEATURE:
<223> OTHER INFORMATION: Oligonucleotide

<400> SEQUENCE: 8
caatgcgctg cagggtgcat cgttagaggc gatagtcggt gcgatcgc            48

<210> SEQ ID NO 9
<211> LENGTH: 24
<212> TYPE: DNA
<213> ORGANISM: Artificial Sequence
<220> FEATURE:
<223> OTHER INFORMATION: Oligonucleotide

<400> SEQUENCE: 9
```
ccgacagtaa gacgggtaag cctg                                          24

<210> SEQ ID NO 10
<211> LENGTH: 22
<212> TYPE: DNA
<213> ORGANISM: Artificial Sequence
<220> FEATURE:
<223> OTHER INFORMATION: Oligonucleotide

<400> SEQUENCE: 10
agcttagtaa agccctcgct ag                                            22

<210> SEQ ID NO 11
<211> LENGTH: 100
<212> TYPE: DNA
<213> ORGANISM: Artificial Sequence
<220> FEATURE:
<223> OTHER INFORMATION: Oligonucleotide

<400> SEQUENCE: 11
catgggctag ctacgtatta attaaagatc tcctagggag ctcaccggtt aaaaataaga   60
gttaccttaa atggtaactc ttattttttt aggcgcgcca                        100

<210> SEQ ID NO 12
<211> LENGTH: 100
<212> TYPE: DNA
<213> ORGANISM: Artificial Sequence
<220> FEATURE:
<223> OTHER INFORMATION: Oligonucleotide

<400> SEQUENCE: 12
agcttggcgc gcctaaaaaa ataagagtta ccatttaagg taactcttat ttttaaccgg   60
tgagctccct aggagatctt taattaatac gtagctagcc                        100

<210> SEQ ID NO 13
<211> LENGTH: 28
<212> TYPE: DNA
<213> ORGANISM: Artificial Sequence
<220> FEATURE:
<223> OTHER INFORMATION: Oligonucleotide

<400> SEQUENCE: 13
gacctaggct ctaaaggagc aattatgg                                      28

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide

<400> SEQUENCE: 14
cgagctctta ttcccactct tgcagg                                        26

<210> SEQ ID NO 15
<211> LENGTH: 48
<212> TYPE: DNA
<213> ORGANISM: Artificial Sequence
<220> FEATURE:
<223> OTHER INFORMATION: Oligonucleotide

<400> SEQUENCE: 15
ggttcagaat ccaacgcaga agcggtgata tcccgtaaaa ccacaggc                48

```
<210> SEQ ID NO 16
<211> LENGTH: 48
<212> TYPE: DNA
<213> ORGANISM: Artificial Sequence
<220> FEATURE:
<223> OTHER INFORMATION: Oligonucleotide

<400> SEQUENCE: 16
gcctgtggtt ttacgggata tcaccgcttc tgcgttggat tctgaacc            48

<210> SEQ ID NO 17
<211> LENGTH: 105
<212> TYPE: DNA
<213> ORGANISM: Artificial Sequence
<220> FEATURE:
<223> OTHER INFORMATION: Oligonucleotide

<400> SEQUENCE: 17
gttaactacg gatgtacatt atggaactga cgactcgcac tttacctgcg cggaaacata     60
ttgcgctggt ggcacacgat caggcctggt gatgatggcg ggatc                   105

<210> SEQ ID NO 18
<211> LENGTH: 120
<212> TYPE: DNA
<213> ORGANISM: Artificial Sequence
<220> FEATURE:
<223> OTHER INFORMATION: Oligonucleotide

<400> SEQUENCE: 18
gggaaattaa gttaccggta gtgcctgttg catacagtac gtgttgttcc agtaacggtt     60
gatgccgttc cacccagctc atcagcatct gtttgcattc agaagaactc gtcaagaagg   120

<210> SEQ ID NO 19
<211> LENGTH: 100
<212> TYPE: DNA
<213> ORGANISM: Artificial Sequence
<220> FEATURE:
<223> OTHER INFORMATION: Oligonucleotide

<400> SEQUENCE: 19
tccagtcgcc gcatttcaac gacgcggtcg atattctgat ccccgattat cagcgttatc     60
tcgcggaccg tctgaagtaa tgtaggctgg agctgcttcg                          100

<210> SEQ ID NO 20
<211> LENGTH: 100
<212> TYPE: DNA
<213> ORGANISM: Artificial Sequence
<220> FEATURE:
<223> OTHER INFORMATION: Oligonucleotide

<400> SEQUENCE: 20
tgtggaaata ctgaaaaatc tggatgtgcc ggtggcgaga aaaccgtaag aaacaggtgg     60
cgtttgccac ctgtgcaata catatgaata tcctccttag                          100

<210> SEQ ID NO 21
<211> LENGTH: 61
<212> TYPE: DNA
<213> ORGANISM: Artificial Sequence
<220> FEATURE:
<223> OTHER INFORMATION: Oligonucleotide

<400> SEQUENCE: 21
atgcttgctg tcagaagatt aacaagatac acattcctta gtttatcatt atcaatactc     60
```

-continued

| g | 61 |

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide

<400> SEQUENCE: 22

| atcctcgaaa ctaagttctt ggt | 23 |

<210> SEQ ID NO 23
<211> LENGTH: 42
<212> TYPE: DNA
<213> ORGANISM: Artificial Sequence
<220> FEATURE:
<223> OTHER INFORMATION: Oligonucleotide

<400> SEQUENCE: 23

| aaacaccaga acttagtttc gaactagttt attcccactc tt | 42 |

<210> SEQ ID NO 24
<211> LENGTH: 62
<212> TYPE: DNA
<213> ORGANISM: Artificial Sequence
<220> FEATURE:
<223> OTHER INFORMATION: Oligonucleotide

<400> SEQUENCE: 24

| tgaaatataa ataacgttct taatactaac ataactataa actagtatgg accgcattat | 60 |
| tc | 62 |

<210> SEQ ID NO 25
<211> LENGTH: 66
<212> TYPE: DNA
<213> ORGANISM: Artificial Sequence
<220> FEATURE:
<223> OTHER INFORMATION: Oligonucleotide

<400> SEQUENCE: 25

| cctggatgta tttacccggt gattgaataa tgcggtccat actagtttat agttatgtta | 60 |
| gtatta | 66 |

<210> SEQ ID NO 26
<211> LENGTH: 60
<212> TYPE: DNA
<213> ORGANISM: Artificial Sequence
<220> FEATURE:
<223> OTHER INFORMATION: Oligonucleotide

<400> SEQUENCE: 26

| gaggcaagct aaacagatct ctagacctag gtacccgccg gcaaattaaa gccttcgagc | 60 |

<210> SEQ ID NO 27
<211> LENGTH: 62
<212> TYPE: DNA
<213> ORGANISM: Artificial Sequence
<220> FEATURE:
<223> OTHER INFORMATION: Oligonucleotide

<400> SEQUENCE: 27

| gcttgagaag gttttgggac gctcgaaggc tttaatttgc taggtctaga gatctgttta | 60 |

<210> SEQ ID NO 28
<211> LENGTH: 64
<212> TYPE: DNA
<213> ORGANISM: Artificial Sequence
<220> FEATURE:
<223> OTHER INFORMATION: Oligonucleotide

<400> SEQUENCE: 28
ctattcgtca tcgatgtcta gctcttcaat catctccggt ccactagtgg atctgatatc    60
acct                                                                 64

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide

<400> SEQUENCE: 29
atgcttgctg tcagaagatt                                                20

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide

<400> SEQUENCE: 30
tagtatggac cgcattattc                                                20

<210> SEQ ID NO 31
<211> LENGTH: 60
<212> TYPE: DNA
<213> ORGANISM: Artificial Sequence
<220> FEATURE:
<223> OTHER INFORMATION: Oligonucleotide

<400> SEQUENCE: 31
atgtctgccc ctaagaagat cgtcgttttg ccaggtgacc agctggagct catagcttca    60

<210> SEQ ID NO 32
<211> LENGTH: 60
<212> TYPE: DNA
<213> ORGANISM: Artificial Sequence
<220> FEATURE:
<223> OTHER INFORMATION: Oligonucleotide

<400> SEQUENCE: 32
tgcgggttgg ggtgtgcaga ttaaagttgt tcatactagt ggatccacta gttctagaaa    60

<210> SEQ ID NO 33
<211> LENGTH: 60
<212> TYPE: DNA
<213> ORGANISM: Artificial Sequence
<220> FEATURE:
<223> OTHER INFORMATION: Oligonucleotide

<400> SEQUENCE: 33
catagcaatc taatctaagt tttctagaac tagtggatcc actagtatga acaactttaa    60

<210> SEQ ID NO 34
<211> LENGTH: 60

```
<212> TYPE: DNA
<213> ORGANISM: Artificial Sequence
<220> FEATURE:
<223> OTHER INFORMATION: Oligonucleotide

<400> SEQUENCE: 34
tgaaatataa ataacgttct taatactaac ataactataa actagtttag cgggcggctt      60

<210> SEQ ID NO 35
<211> LENGTH: 60
<212> TYPE: DNA
<213> ORGANISM: Artificial Sequence
<220> FEATURE:
<223> OTHER INFORMATION: Oligonucleotide

<400> SEQUENCE: 35
tgtcagccgc cgtatatacg aagccgcccg ctaaactagt ttatagttat gttagtatta      60

<210> SEQ ID NO 36
<211> LENGTH: 60
<212> TYPE: DNA
<213> ORGANISM: Artificial Sequence
<220> FEATURE:
<223> OTHER INFORMATION: Oligonucleotide

<400> SEQUENCE: 36
ctccatgtcg ctggccgggt gacccggcgg ggacgaggca gcaaattaaa gccttcgagc      60

<210> SEQ ID NO 37
<211> LENGTH: 60
<212> TYPE: DNA
<213> ORGANISM: Artificial Sequence
<220> FEATURE:
<223> OTHER INFORMATION: Oligonucleotide

<400> SEQUENCE: 37
gcttgagaag gttttgggac gctcgaaggc tttaatttgc tgcctcgtcc ccgccgggtc      60

<210> SEQ ID NO 38
<211> LENGTH: 60
<212> TYPE: DNA
<213> ORGANISM: Artificial Sequence
<220> FEATURE:
<223> OTHER INFORMATION: Oligonucleotide

<400> SEQUENCE: 38
ttaagcaagg attttcttaa cttcttcggc gacagcatca cagtatagcg accagcattc      60

<210> SEQ ID NO 39
<211> LENGTH: 21
<212> TYPE: DNA
<213> ORGANISM: Artificial Sequence
<220> FEATURE:
<223> OTHER INFORMATION: Oligonucleotide

<400> SEQUENCE: 39
atgtctgccc ctaagaagat c                                               21

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide

<400> SEQUENCE: 40
```

```
actagtttag cgggcggctt                                              20
```

<210> SEQ ID NO 41
<211> LENGTH: 60
<212> TYPE: DNA
<213> ORGANISM: Artificial Sequence
<220> FEATURE:
<223> OTHER INFORMATION: Oligonucleotide

<400> SEQUENCE: 41

```
atgtcgaaag ctacatataa ggaacgtgct gctactcatc gccagatctg tttagcttgc   60
```

<210> SEQ ID NO 42
<211> LENGTH: 40
<212> TYPE: DNA
<213> ORGANISM: Artificial Sequence
<220> FEATURE:
<223> OTHER INFORMATION: Oligonucleotide

<400> SEQUENCE: 42

```
gtgcgagtcg tcagttccat aatacgcaaa ccgcctctcc                        40
```

<210> SEQ ID NO 43
<211> LENGTH: 40
<212> TYPE: DNA
<213> ORGANISM: Artificial Sequence
<220> FEATURE:
<223> OTHER INFORMATION: Oligonucleotide

<400> SEQUENCE: 43

```
ggagaggcgg tttgcgtatt atggaactga cgactcgcac                        40
```

<210> SEQ ID NO 44
<211> LENGTH: 60
<212> TYPE: DNA
<213> ORGANISM: Artificial Sequence
<220> FEATURE:
<223> OTHER INFORMATION: Oligonucleotide

<400> SEQUENCE: 44

```
ttagttttgc tggccgcatc ttctcaaata tgcttccctt tacttcagac ggtccgcgag   60
```

<210> SEQ ID NO 45
<211> LENGTH: 18
<212> TYPE: DNA
<213> ORGANISM: Artificial Sequence
<220> FEATURE:
<223> OTHER INFORMATION: Oligonucleotide

<400> SEQUENCE: 45

```
ggaactgacg actcgcac                                                18
```

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide

<400> SEQUENCE: 46

```
ttagtttcta gagttgatga                                              20
```

<210> SEQ ID NO 47
<211> LENGTH: 350
<212> TYPE: PRT
<213> ORGANISM: Picrophilus torridus

<400> SEQUENCE: 47

| Met | Asn | Phe | Asn | Lys | Ile | Lys | Ser | Met | His | Phe | Pro | Ser | Asp | Val | Tyr |
|---|---|---|---|---|---|---|---|---|---|---|---|---|---|---|---|
| 1 | | | | 5 | | | | | 10 | | | | | 15 | |

Ile Gly His Asp Ala Ile Leu Asn Ile Gly Ser Val Val Ser Lys Phe
             20               25              30

Leu Lys Ser Gly Glu Val Leu Leu Ile Thr Gly Glu Asn Thr Tyr Asn
     35                 40                45

Ile Ala Gly Lys Lys Val Leu Ser Asn Leu Asn Asp Phe Asp Val Asn
50                55                60

Val Ile Ile Ala Ser Arg Ala Thr Arg Asp Ser Ile Lys Ser Ile Glu
65             70             75          80

Glu Ser Leu Lys Asn Arg Arg Ser Gly Ile Val Leu Gly Val Gly Gly
             85             90             95

Gly Ser Lys Ile Asp Ile Ala Lys Lys Ile Ala Tyr Asp Leu Gly Ile
         100           105           110

Pro Phe Ile Ser Val Pro Thr Thr Pro Ser His Asp Gly Ile Ala Ser
     115               120              125

Pro Arg Ala Ser Ile Tyr Asp Gly Lys Ser Val Tyr Ser Glu Glu Ala
   130               135              140

Thr Met Pro Ser Ala Ile Val Ala Asp Thr Ser Ile Met Val Leu Ala
145              150             155         160

Pro Tyr Arg Tyr Val Ala Ala Gly Ala Ala Asp Val Ile Ser Asn Ile
             165           170           175

Thr Ala Val Leu Asp Trp Lys Leu Ala Asn Arg Leu Lys Gly Glu Glu
         180               185           190

Phe Ser Ser Thr Ala Ala Val Met Ser Glu Tyr Ala Gly Arg Glu Leu
     195               200              205

Ile Glu Arg Ser Ser Met Ile Gln Pro Gly Leu Glu Glu Ser Ile Trp
   210               215              220

Leu Val Thr Lys Gln Ile Leu Ala Ser Gly Ala Ala Met Ala Ile Ala
225              230             235         240

Gly Ser Ser Arg Pro Ala Ser Gly Ser Glu His Leu Phe Ser His Ala
             245           250           255

Ile Glu Ile Leu Gly Pro Gly Ser Ser Ile His Gly Glu Gln Cys Ala
         260           265           270

Met Gly Ser Leu Ile Ser Met Tyr Leu His Gly Gly Asp Trp Glu Leu
     275               280              285

Leu Lys Asn Thr Tyr Arg Lys Ile Gly Leu Asn Thr Arg Ala Glu Ser
   290               295              300

Tyr Gly Ile Gly Arg Glu Val Ala Ile Lys Ala Leu Ser Ile Ala His
305              310             315         320

Arg Ile Arg Pro Ser Arg Tyr Thr Ile Leu Gly Glu Ser Asp Leu Ser
             325           330           335

Tyr Asn Val Ala Glu Arg Ile Leu Ser Ile Thr Gly Ile Ile
         340               345           350

<210> SEQ ID NO 48
<211> LENGTH: 352
<212> TYPE: PRT
<213> ORGANISM: Thermoplasma volcanium

<400> SEQUENCE: 48

Met Glu Phe Gln Lys Tyr Arg Thr Met His Phe Pro Arg Asp Val Tyr
1              5                10             15

```
Ile Gly His Asp Val Leu Asn Arg Val Leu Asp Val Asp Gln Asn
            20                  25                  30

Ser Arg Thr Arg Asp Val Ile Ile Val Thr Gly Asn Thr Thr Tyr Glu
        35                  40                  45

Leu Ala Gly Lys Lys Ile Val Glu Ile Leu Ala Ser Ser Pro Tyr Glu
50                  55                  60

Val His Leu Ser Phe Ala Gly Glu Ala Asn Tyr Glu Asn Leu Lys Lys
65                  70                  75                  80

Ile Glu Glu Glu Thr Asn Asp Val Asn Ala Gly Ile Ile Gly Val
                85                  90                  95

Gly Gly Gly Thr Lys Ile Asp Leu Ala Lys Lys Leu Ala Tyr Asp Lys
            100                 105                 110

Asn Leu Pro Phe Ile Ser Ile Pro Thr Ser Pro Ser His Asp Gly Ile
        115                 120                 125

Ala Ser Pro Arg Ala Ser Leu Arg Arg Asn Gly Ile Ser Tyr Ser Glu
130                 135                 140

Glu Gly Ala Met Pro Ile Gly Val Ile Ala Asp Thr Ser Val Met Ile
145                 150                 155                 160

Lys Ala Pro Tyr Arg Tyr Leu Ala Ala Gly Ala Ala Asp Val Ile Ser
                165                 170                 175

Asn Ile Ser Ala Val Lys Asp Trp Lys Leu Ala His Arg Leu Arg Gly
            180                 185                 190

Glu Glu Phe Ser Ser Ser Ala Ala Met Ser Glu Tyr Ser Ala Gln
        195                 200                 205

Glu Val Ile Ser Gln Val Gly Glu Ile Arg Lys Tyr Asp Glu Ser Ser
210                 215                 220

Val Trp Leu Val Thr Lys Asn Ile Leu Ala Ser Gly Thr Ala Met Ala
225                 230                 235                 240

Ile Ala Gly Asn Ser Arg Pro Gly Ser Gly Ser Glu His Leu Phe Ala
                245                 250                 255

His Ala Leu Glu Ala Ala Gly Val Asn Asn Met Leu His Gly Glu Met
            260                 265                 270

Cys Ala Met Gly Thr Ile Val Ser Leu Tyr Leu His Asp Asp Asn Trp
        275                 280                 285

Gln Lys Ile Arg Asp Val Phe Glu Ser Leu Gly Val Ser Val Lys Ala
290                 295                 300

Arg Asp Tyr Gly Leu Lys Glu Val Val Ile Glu Ala Leu Arg Arg
305                 310                 315                 320

Ala His Ala Ile Arg Pro Glu Arg Tyr Thr Ile Leu Gly Glu Ser Asp
                325                 330                 335

Met Ser Tyr Asp Ala Ala Val Lys Ala Leu Glu Leu Thr Gly Ile Ile
            340                 345                 350

<210> SEQ ID NO 49
<211> LENGTH: 352
<212> TYPE: PRT
<213> ORGANISM: Thermoplasma acidophilum

<400> SEQUENCE: 49

Met Glu Phe Gln Lys Phe Arg Thr Met His Phe Pro Arg Asp Val Tyr
1               5                   10                  15

Ile Gly His Asp Val Leu Glu His Ile Val Asp Val Val Gly Glu Asn
            20                  25                  30

Ser Arg Asn Lys Asn Ala Ile Ile Val Ser Gly Asp Leu Thr Tyr Glu
```

```
            35                  40                  45
Leu Ala Gly Arg Lys Val His Asp Leu Leu Ser Thr Tyr Gly Tyr Glu
 50                  55                  60

Val His Val Phe Leu Ala Gly Asn Ala Asn Tyr Asp Thr Leu Glu Arg
 65                  70                  75                  80

Ile Glu Tyr Glu Ser Leu Asp Ile Gln Ala Gly Ile Val Ile Gly Val
                 85                  90                  95

Gly Gly Gly Ala Lys Ile Asp Leu Ala Lys Lys Leu Ala Phe Asp Arg
            100                 105                 110

Lys Leu Pro Phe Val Ser Val Pro Thr Ala Pro Ser His Asp Gly Ile
            115                 120                 125

Ala Ser Pro Arg Ala Ser Leu Arg Arg Asn Gly Ile Ser Tyr Ser Glu
130                 135                 140

Glu Gly Ala Met Pro Ile Gly Val Ile Ala Asp Thr Ala Ile Met Ile
145                 150                 155                 160

Lys Ala Pro Tyr Arg Tyr Leu Ala Ala Gly Ala Ala Asp Val Ile Ser
                165                 170                 175

Asn Leu Ser Ala Val Lys Asp Trp Lys Leu Ala His Arg Leu Lys Gly
            180                 185                 190

Glu Glu Phe Ser Ser Ser Ala Ala Met Ser Glu Tyr Ser Ala Gln
            195                 200                 205

Glu Val Leu Ser Gln Ile Asn Glu Ile Lys Lys Tyr Glu Glu Ser Ser
210                 215                 220

Val Trp Leu Val Thr Lys Asn Ile Leu Ala Ser Gly Thr Ala Met Ala
225                 230                 235                 240

Ile Ala Gly Asn Ser Arg Pro Gly Ser Gly Ser Glu His Leu Phe Ala
                245                 250                 255

His Ala Leu Glu Ala Ala Gly Val Glu Asn Met Leu His Gly Glu Met
            260                 265                 270

Cys Ala Met Gly Thr Val Ile Ser Met Tyr Leu His Asp Glu Asn Trp
            275                 280                 285

Gln Gln Ile Lys Glu Ala Phe Asp Asn Leu Gly Ile Ser Ile Arg Ser
290                 295                 300

Arg Asp Tyr Gly Ile Glu Asp Glu Ile Val Ile Asn Ala Leu Arg Thr
305                 310                 315                 320

Ala His Ala Ile Arg Pro Glu Arg Tyr Thr Ile Leu Gly Glu Ser Asp
                325                 330                 335

Met Ser Tyr Asp Ala Ala Val Lys Ala Leu Glu Leu Thr Gly Ile Ile
            340                 345                 350

<210> SEQ ID NO 50
<211> LENGTH: 342
<212> TYPE: PRT
<213> ORGANISM: Pyrobaculum aerophilum

<400> SEQUENCE: 50

Met Lys Gln Leu Glu Ser Phe Gln Ile Pro Arg Ile Val Ile Phe Gly
 1               5                  10                  15

Pro Gly Ala Ile Leu Lys Thr Pro Leu Val Val Ser Glu Leu Lys Ala
            20                  25                  30

Gly Arg Ile Leu Val Ile Ser Gly Lys Ser Ala Thr Thr Ala Tyr Ala
            35                  40                  45

Asn Gln Val Ala Gln Leu Leu Ser Asn Tyr Ser Val Asp Val Val Arg
 50                  55                  60
```

Tyr Asn Glu Val Asp Leu Ser Lys Ser Ser Tyr Asp Leu Val Ile Gly
 65                  70                  75                  80

Val Gly Gly Arg Pro Ile Asp Met Ala Lys Val Tyr Ser Cys Val
             85                  90                  95

His Lys Lys Pro Leu Val Val Ile Pro Thr Ala Ala Ser His Asp Gly
             100                 105                 110

Ile Ala Ser Pro Tyr Val Ser Tyr Thr Leu Ser Gln Lys Leu Gln Thr
             115                 120                 125

Tyr Gly Lys Ile Val Ala Ser Pro Val Ala Ile Ile Ala Asp Thr Ser
             130                 135                 140

Val Ile Leu Ser Ala Pro Ser Arg Leu Leu Lys Ala Gly Ile Gly Asp
145                 150                 155                 160

Leu Leu Gly Lys Ile Ile Ala Val Arg Asp Trp Gln Leu Ala His Arg
                 165                 170                 175

Leu Lys Gly Glu Glu Tyr Ser Glu Tyr Ala Ala His Leu Ala Val Thr
                 180                 185                 190

Ser Tyr Lys Ile Ala Ala Thr Asn Ala Arg Arg Ile Arg Asn Phe Thr
             195                 200                 205

Arg Glu Glu Asp Val Arg Val Leu Val Lys Ala Leu Ile Gly Cys Gly
             210                 215                 220

Val Ala Met Gly Ile Ala Gly Ser Ser Arg Pro Cys Ser Gly Ser Glu
225                 230                 235                 240

His Leu Phe Ala His Ala Ile Glu Leu Arg Leu Gln Glu Glu Ser Ser
                 245                 250                 255

Glu Ala Val His Gly Glu Leu Val Ala Leu Gly Thr Ile Ile Met Ala
             260                 265                 270

Tyr Leu His Gly Ile Asn Trp Arg Arg Ile Lys Lys Ile Ala Glu Ile
             275                 280                 285

Val Gly Leu Pro Thr Thr Leu Lys Gln Ala Gly Ile Asp Ala Asp Met
             290                 295                 300

Ala Val Glu Ala Leu Thr Thr Ala His Ala Leu Arg Pro Asp Arg Tyr
305                 310                 315                 320

Thr Ile Leu Gly Asn Gly Leu Ser Arg Glu Ala Ala Arg Arg Ala Leu
                 325                 330                 335

Glu Asp Thr Glu Leu Ile
             340

<210> SEQ ID NO 51
<211> LENGTH: 335
<212> TYPE: PRT
<213> ORGANISM: Methanocaldococcus jannaschii

<400> SEQUENCE: 51

Met Ile Ile Val Thr Pro Arg Tyr Thr Ile Ile Glu Asp Gly Ala Ile
 1               5                  10                  15

Asn Lys Ile Glu Glu Ile Leu Lys Lys Leu Asn Leu Lys Asn Pro Leu
             20                  25                  30

Val Ile Thr Gly Lys Asn Thr Lys Lys Tyr Cys Arg Phe Phe Tyr Asp
             35                  40                  45

Ile Val Tyr Tyr Asp Glu Ile Leu Asn Asn Leu Glu Ile Glu Leu Lys
         50                  55                  60

Lys Tyr Thr Ala Tyr Asp Cys Val Ile Gly Ile Gly Gly Gly Arg Ser
 65                  70                  75                  80

Ile Asp Thr Gly Lys Tyr Leu Ala Tyr Lys Leu Gly Ile Pro Phe Ile
             85                  90                  95

```
Ser Val Pro Thr Thr Ala Ser Asn Asp Gly Ile Ala Ser Pro Ile Val
            100                 105                 110

Ser Ile Arg Gln Pro Ser Phe Met Val Asp Ala Pro Ile Ala Ile Ile
            115                 120                 125

Ala Asp Thr Glu Ile Ile Lys Lys Ser Pro Arg Arg Leu Leu Ser Ala
130                 135                 140

Gly Met Gly Asp Ile Val Ser Asn Ile Thr Ala Val Leu Asp Trp Lys
145                 150                 155                 160

Leu Ala Tyr Lys Glu Lys Gly Glu Lys Tyr Ser Glu Ser Ser Ala Ile
                165                 170                 175

Phe Ser Lys Thr Ile Ala Lys Glu Leu Ile Ser Tyr Val Leu Asn Ser
            180                 185                 190

Asp Leu Ser Glu Tyr His Asn Lys Leu Val Lys Ala Leu Val Gly Ser
                195                 200                 205

Gly Ile Ala Ile Ala Ile Ala Asn Ser Ser Arg Pro Ala Ser Gly Ser
210                 215                 220

Glu His Leu Phe Ser His Ala Leu Asp Lys Leu Lys Glu Glu Tyr Asn
225                 230                 235                 240

Leu Asn Ile Asn Ser Leu His Gly Glu Gln Cys Gly Ile Gly Thr Ile
                245                 250                 255

Met Met Ser Tyr Leu His Glu Lys Glu Asn Lys Lys Leu Ser Gly Leu
            260                 265                 270

His Glu Lys Ile Lys Met Ser Leu Lys Lys Val Asp Ala Pro Thr Thr
            275                 280                 285

Ala Lys Glu Leu Gly Phe Asp Glu Asp Ile Ile Ile Glu Ala Leu Thr
290                 295                 300

Met Ala His Lys Ile Arg Asn Arg Trp Thr Ile Leu Arg Asp Gly Leu
305                 310                 315                 320

Ser Arg Glu Glu Ala Arg Lys Leu Ala Glu Glu Thr Gly Val Ile
                325                 330                 335

<210> SEQ ID NO 52
<211> LENGTH: 352
<212> TYPE: PRT
<213> ORGANISM: Aeropyrum pernix

<400> SEQUENCE: 52

Met Tyr Thr Ser Phe His Arg Ile Asp Leu Pro Arg Thr Ile Val Val
1               5                   10                  15

Gly Gly Gly Val Leu Asp Lys Ala Gly Gly Tyr Val Ser Gly Val Ala
            20                  25                  30

Gln Arg Gly Ser Tyr Val Leu Val Ser Gly Pro Thr Val Ser Ser
            35                  40                  45

Lys Tyr Phe Glu Arg Leu Arg Ala Ser Leu Glu Ala Glu Gly Leu Thr
50                  55                  60

Val Gly Leu Lys Ile Ile Arg Asp Ala Thr Val Glu Thr Ala Glu Glu
65                  70                  75                  80

Val Ala Arg Glu Ala Leu Glu Ser Arg Ile Glu Val Val Ala Gly Leu
                85                  90                  95

Gly Gly Gly Lys Ser Ile Asp Val Ala Lys Tyr Ala Ser Lys Arg Ala
            100                 105                 110

Gly Ser Val Phe Val Ser Ile Pro Thr Val Ala Ser His Asp Gly Ile
            115                 120                 125

Thr Ser Pro Phe Ser Ser Leu Lys Gly Phe Asp Lys Pro Ile Ser Arg
```

Pro Ala Lys Ala Pro Glu Ala Ile Ile Ile Asp Val Asp Val Ile Ala
145                 150                 155                 160

Glu Ala Pro Arg Arg Tyr Asn Ile Ala Gly Phe Gly Asp Leu Ile Gly
                165                 170                 175

Lys Tyr Thr Ala Val Leu Asp Trp Arg Leu Ala His Lys Leu Arg Leu
            180                 185                 190

Glu Tyr Tyr Gly Glu Tyr Ala Ala Ser Leu Ala Leu Leu Ser Ala Lys
        195                 200                 205

His Val Ser Gln Tyr Ala Glu Glu Ile Ala Leu Gly Thr Arg Glu Gly
    210                 215                 220

Tyr Arg Val Leu Leu Glu Ala Leu Val Ser Ser Gly Val Ser Met Cys
225                 230                 235                 240

Ile Ala Gly Ser Thr Arg Pro Ala Ser Gly Ser Glu His Leu Phe Ala
                245                 250                 255

His Ala Leu His Ile Val Ala Arg Asn Lys Pro Leu His Gly Glu Ala
            260                 265                 270

Val Gly Val Gly Thr Ile Met Met Ala Tyr Leu His Gly Lys Asn Trp
        275                 280                 285

Arg Arg Ile Arg Gly Leu Leu Lys Thr Val Gly Ala Pro Thr Asn Ala
    290                 295                 300

Lys Glu Leu Gly Val Glu Asp Asp Glu Val Val Glu Ala Leu Thr Ile
305                 310                 315                 320

Ala Ala Arg Ile Arg Pro Glu Arg Tyr Thr Ile Leu Gly Glu Lys Gly
                325                 330                 335

Leu Thr Arg Glu Ala Ala Glu Ala Leu Ala Arg Lys Thr Gly Val Ile
            340                 345                 350

<210> SEQ ID NO 53
<211> LENGTH: 352
<212> TYPE: PRT
<213> ORGANISM: Halobacterium salinarum

<400> SEQUENCE: 53

Met Phe Glu Lys Ser Thr Trp Ile Arg Leu Pro Arg Asn Val Val Val
1               5                   10                  15

Gly His Gly Val Leu Asp Asp Ala Val Glu Val Val Arg Asp Thr His
            20                  25                  30

Leu Thr Gly Arg Pro Leu Val Val Thr Ser Pro Thr Pro Lys Thr Val
        35                  40                  45

Ala Ala Glu Asn Val Val Ala Gln Phe Glu Ala Val Gly Asp Asp Pro
    50                  55                  60

Ala Val Val Val Glu Glu Ala Thr Phe Asn Ser Val Glu Arg Val
65                  70                  75                  80

Leu Gly Glu Ala Glu Ala Val Asp Pro Gly Tyr Leu Val Gly Val Gly
                85                  90                  95

Gly Gly Lys Ala Ile Asp Ile Ala Lys Leu Ala Ser Asp His Leu Asn
            100                 105                 110

Val Gly Phe Val Ser Val Pro Thr Ala Ala Ser His Asp Gly Ile Val
        115                 120                 125

Ser Gly Arg Gly Ser Val Pro Glu Gly Asp Thr Arg His Ser Val Ser
    130                 135                 140

Ala Ala Pro Pro Leu Ala Val Ile Ala Asp Thr Gly Val Ile Ala Asp
145                 150                 155                 160

Ala Pro Trp Glu Leu Thr Thr Ala Gly Cys Ala Asp Ile Ile Ser Asn
            165                 170                 175

Tyr Thr Ala Val Lys Asp Trp Arg Leu Ala Asn Arg Leu Gln His Val
        180                 185                 190

Pro Tyr Ser Glu Tyr Ala Gly Ala Leu Ser Gln Met Thr Ala Glu Met
        195                 200                 205

Leu Val Asp Asn Ala Ala Asn Ile Lys Pro Glu Leu Glu Glu Ser Ala
        210                 215                 220

Trp Val Val Lys Ala Leu Val Ser Ser Gly Val Ala Met Ser Ile
225                 230                 235                 240

Ala Asp Ser Ser Arg Pro Ala Ser Gly Ser Glu His Leu Phe Ser His
            245                 250                 255

Gln Leu Asp Arg Ile Ala Pro Gly Lys Ala Leu His Gly His Gln Val
        260                 265                 270

Gly Val Gly Ser Ile Leu Ala Glu Tyr Leu His Ser Gly Gln Glu Gly
        275                 280                 285

Gln Trp Met Ala Val Arg Asp Ala Leu Ala Ser Leu Asp Ala Pro Thr
        290                 295                 300

Thr Ala Asp Glu Leu Gly Val Ala Asp Glu Val Leu Ala Ala Leu
305                 310                 315                 320

Thr Ser Ala His Glu Ile Arg Asp Arg Tyr Thr Ile Leu Gly Gly Gly
            325                 330                 335

Ile Ser Glu Val Ala Ala Arg Glu Ala Ala Ser Arg Thr Gly Val Ile
        340                 345                 350

<210> SEQ ID NO 54
<211> LENGTH: 351
<212> TYPE: PRT
<213> ORGANISM: Sulfolobus solfataricus

<400> SEQUENCE: 54

Met Asn Val Lys Glu His Val Ile Ser Leu Pro Arg Arg Val Phe Val
1               5                   10                  15

Gly His Asp Ile Val Tyr Asp Ile Ser Ile Tyr Phe Ser Gln Leu Gly
            20                  25                  30

Val Thr Pro Pro Phe Leu Ile Val Thr Gly Thr Lys Tyr Thr Lys Lys
        35                  40                  45

Ile Ala Asp Lys Val Ile Glu Asn Leu Pro Lys Asp Ala Lys Tyr Glu
    50                  55                  60

Val Val Glu Ile Asp Ser Ala Thr Leu Asp Asp Val Tyr Met Val Glu
65                  70                  75                  80

Glu Val Ile Lys Arg Ile Ser Pro Ser Leu Leu Gly Ile Gly Gly
            85                  90                  95

Gly Lys Val Ile Asp Val Thr Lys Tyr Ala Ala Phe Arg Asn Ser Leu
        100                 105                 110

Glu Phe Val Ser Ile Pro Thr Ser Pro Ser His Asp Gly Ile Thr Ser
        115                 120                 125

Pro Phe Ala Ser Ile Lys Gly Leu Gln Lys Pro Val Ser Val Lys Ala
    130                 135                 140

Lys Glu Pro Leu Ala Ile Ala Asp Ile Glu Ile Leu Ser Leu Ser
145                 150                 155                 160

Pro Arg Arg Leu Ile Asn Ala Gly Ile Gly Asp Thr Ile Gly Lys Ile
            165                 170                 175

Ile Ala Val Arg Asp Trp Lys Leu Ala Ala Lys Leu Arg Gly Glu Tyr
        180                 185                 190

Tyr Gly Asp Tyr Thr Ala Ser Leu Ala Leu Met Ser Ala Lys His Ala
            195                 200                 205

Phe Gln Cys Thr Lys Ile Ile Asn Lys Asp Ile Lys Tyr Gly Val Arg
    210                 215                 220

Met Leu Met Glu Ala Leu Ile Ser Ser Gly Val Ala Met Gly Met Ala
225                 230                 235                 240

Gly Ser Thr Arg Pro Ala Ser Gly Ser Glu His Leu Phe Ala His Ala
                245                 250                 255

Val Glu Leu Ile His Pro Glu Gly Ile Leu His Gly Glu Leu Val Gly
            260                 265                 270

Leu Gly Thr Ile Ile Met Ala Tyr Leu His Gly Ile Asn Trp Lys Ile
        275                 280                 285

Ile Arg Asn Arg Leu Lys Lys Ile Gly Phe Pro Val Lys Ala Lys Asp
    290                 295                 300

Leu Gly Leu Ser Asp Glu Val Ile Lys Ala Leu Thr Ile Ala His
305                 310                 315                 320

Thr Ile Arg Pro Glu Arg Tyr Thr Ile Leu Gly Asp Arg Gly Leu Thr
                325                 330                 335

Trp Ser Ser Ala Glu Lys Ile Ala Arg Val Thr Lys Ile Ile Asp
            340                 345                 350

<210> SEQ ID NO 55
<211> LENGTH: 351
<212> TYPE: PRT
<213> ORGANISM: Sulfolobus acidocaldarius

<400> SEQUENCE: 55

Met Glu Ile Lys Glu His Ile Ile Asn Leu Pro Lys His Ile Tyr Thr
1               5                   10                  15

Gly Tyr Gly Ile Leu Asp Asn Phe Arg Asn Tyr Leu Gln Thr Leu Asn
            20                  25                  30

Leu Pro Gln Pro Phe Leu Val Ile Thr Gly Pro Val Ile His Gln Glu
        35                  40                  45

Ile Phe Ser Lys Arg Ile Glu Glu His Ile Lys Asp Phe Lys Tyr Glu
    50                  55                  60

Val Val Ile Val Asn Lys Ser Asp Leu Ser Glu Ala Glu Lys Val Glu
65                  70                  75                  80

Asp Ile Ala Arg Gln Lys Gly Ile Lys Thr Ile Leu Gly Val Gly Gly
                85                  90                  95

Gly Thr Val Ile Asp Ile Ala Lys Phe Thr Ala Tyr Lys Ile Asp Arg
            100                 105                 110

Glu Phe Ile Ser Ile Pro Thr Ser Pro Ser His Asp Gly Ile Thr Ser
        115                 120                 125

Pro Phe Ala Ala Ile Lys Gly Leu Gly Lys Pro Ile Ser Ile Lys Ala
    130                 135                 140

Lys Glu Pro Leu Ala Ile Ile Ser Asp Val Glu Ile Leu Ala Ser Ala
145                 150                 155                 160

Pro Arg Arg Leu Ile Asn Ala Gly Ile Gly Asp Thr Leu Gly Lys Ile
                165                 170                 175

Thr Ala Val Arg Asp Trp Arg Leu Ala His Lys Leu Arg Gly Glu Tyr
            180                 185                 190

Tyr Gly Asp Tyr Thr Ala Ser Leu Ala Leu Met Ser Ala Arg His Ala
        195                 200                 205

Leu Ser Cys Thr Lys Ile Ile Asn Lys Asp Ile Arg Ala Gly Val Arg

```
            210                 215                 220
Val Leu Thr Glu Ala Leu Ile Ser Ser Gly Val Ala Met Gly Met Ala
225                 230                 235                 240

Gly Ser Thr Arg Pro Ala Ser Gly Ser Glu His Leu Phe Ala His Ala
                245                 250                 255

Ile Glu Leu Leu Tyr Pro Asn Leu Gly Leu His Gly Glu Leu Val Ala
                260                 265                 270

Leu Gly Thr Ile Met Met Ala Tyr Ile His Gly Ile Asn Trp Arg Arg
                275                 280                 285

Ile Arg Arg Ala Met Lys Lys Ile Gly Leu Pro Val Thr Ser Lys Gln
            290                 295                 300

Ile Gly Ile Pro Asp Glu Gly Ile Ile Lys Ala Leu Thr Ile Ala His
305                 310                 315                 320

Ser Ile Arg Pro Glu Arg Tyr Thr Ile Leu Gly Asp Arg Gly Leu Thr
                325                 330                 335

Trp Glu Ser Ala Glu Lys Ile Ala Arg Glu Thr Gly Val Ile Ser
                340                 345                 350

<210> SEQ ID NO 56
<211> LENGTH: 350
<212> TYPE: PRT
<213> ORGANISM: Sulfolobus tokodaii

<400> SEQUENCE: 56

Met Glu Leu Lys Glu His Ile Ile Asp Leu Pro Lys Lys Val Tyr Ile
1               5                   10                  15

Gly Tyr Asp Ile Ile Asp Asn Ile Lys Glu Tyr Ile Leu Ser Leu Asn
            20                  25                  30

Leu Ser Gly Pro Phe Leu Ile Val Thr Gly Pro Leu Val Arg Lys Ile
        35                  40                  45

Ile Thr Asp Lys Ile Ile Glu Asn Phe Lys Asp Glu Ser Val Glu Val
    50                  55                  60

Val Glu Val Lys Ile Ala Ser Ile Asp Glu Val Asn Lys Val Glu Glu
65                  70                  75                  80

Met Ala Lys Gly Ser Arg Ile Asn Thr Ile Ile Gly Val Gly Gly Gly
                85                  90                  95

Asn Ile Ile Asp Val Ala Lys Tyr Val Ala Tyr Arg Ile Gly Lys Glu
            100                 105                 110

Phe Val Ser Leu Pro Thr Ala Pro Ser His Asp Gly Ile Thr Ser Pro
        115                 120                 125

Phe Ala Ser Ile Lys Gly Leu Gly Lys Pro Thr Ser Val Lys Ala Lys
    130                 135                 140

Gly Pro Ile Ala Ile Ala Asp Ile Asn Val Leu Ala Ser Ala Pro
145                 150                 155                 160

Arg Arg Leu Ile Asn Ala Gly Ile Gly Asp Thr Ile Gly Lys Ile Thr
                165                 170                 175

Ala Val Arg Asp Trp Gln Leu Ala Ala Lys Leu Arg Gly Glu Tyr Tyr
            180                 185                 190

Gly Asp Tyr Thr Ala Ser Leu Ala Leu Met Ser Ala Lys His Ala Leu
        195                 200                 205

Ser Cys Ala Lys Ile Leu Asp Lys Asp Val Arg Ala Gly Val Arg Val
    210                 215                 220

Leu Thr Glu Ala Leu Ile Ser Ser Gly Val Ala Met Gly Met Ala Gly
225                 230                 235                 240
```

```
Ser Thr Arg Pro Ala Ser Gly Ser Glu His Leu Phe Ala His Ala Ile
            245                 250                 255

Glu Ile Leu Tyr Pro Asp Lys Ala Leu His Gly Glu Leu Val Ala Leu
        260                 265                 270

Gly Thr Ile Leu Met Ala Tyr Ile His Gly Ile Asn Trp Lys Lys Ile
        275                 280                 285

Lys Lys Ala Met Lys Lys Val Gly Leu Pro Thr Lys Ala Lys Gln Leu
        290                 295                 300

Gly Ile Pro Asp Glu Ile Ile Lys Ala Leu Thr Ile Ala His Thr
305                 310                 315                 320

Ile Arg Pro Glu Arg Tyr Thr Ile Leu Gly Asp Arg Gly Leu Thr Trp
                325                 330                 335

Glu Ala Ala Glu Lys Ile Ala Lys Glu Thr Gly Ile Ile Asp
        340                 345                 350

<210> SEQ ID NO 57
<211> LENGTH: 356
<212> TYPE: PRT
<213> ORGANISM: Methanosarcina mazei

<400> SEQUENCE: 57

Met Lys Leu Thr Ile Asn Lys Asn Ser Ala Lys Trp Met Gln Leu Pro
1               5                   10                  15

Arg Asp Val Leu Val Gly His Gly Val Leu Glu Glu Val Gly Asp Val
            20                  25                  30

Cys Arg Asp Leu Lys Leu Lys Gly Asn Ala Leu Ile Val Thr Gly Ser
        35                  40                  45

Thr Thr Gln Asp Val Ala Gly Lys Arg Val Ser Arg Leu Leu Glu Asp
50                  55                  60

Ala Gly Asn Ser Thr Glu Thr Val Leu Thr Cys Arg Ala Thr Met Glu
65                  70                  75                  80

Glu Val Asp Lys Leu Met Glu Lys Ala Leu Asn Thr Glu Ala Thr Phe
                85                  90                  95

Leu Leu Gly Val Gly Ser Gly Arg Ser Ile Asp Leu Ala Lys Leu Ala
            100                 105                 110

Ser Thr Arg Leu Glu Ile Pro Phe Ile Ser Val Pro Thr Ala Ala Ser
        115                 120                 125

His Asp Gly Ile Ala Ser Ser Arg Ala Ser Val Ile Asp Asn Gly Lys
    130                 135                 140

Asn Ala Ser Ile Gln Ala Gln Ala Pro Leu Ala Val Ile Ala Asp Thr
145                 150                 155                 160

Glu Ile Ile Ser Ala Ala Pro Tyr Arg Phe Leu Ala Ala Gly Cys Gly
                165                 170                 175

Asp Ile Ile Ser Asn Tyr Thr Ala Val Leu Asp Trp Glu Leu Ala Ser
            180                 185                 190

Arg Leu Arg Asn Glu Tyr Phe Gly Glu Tyr Ala Ala Ala Leu Ser Arg
        195                 200                 205

Met Ala Ala Arg Val Val Ile Glu Asn Ala Asp Ser Ile Lys Pro Asp
    210                 215                 220

His Glu Thr Ser Ala Arg Leu Val Val Lys Ala Leu Val Ser Asn Gly
225                 230                 235                 240

Val Ala Met Ser Ile Ala Gly Ser Ser Arg Pro Ala Ser Gly Ser Glu
                245                 250                 255

His Met Phe Ser His Ala Leu Asp Arg Ile Ala Pro Lys Ala Ala Leu
            260                 265                 270
```

```
His Gly Glu Gln Cys Gly Val Gly Thr Ile Met Met Met Tyr Leu His
        275                 280                 285

Gly Gly Asn Trp Gln Glu Ile Arg Asp Ala Leu Lys Lys Ile Gly Ala
    290                 295                 300

Pro Thr Asn Ala Glu Glu Leu Gly Ile Glu Asp Lys Tyr Ile Ile Glu
305                 310                 315                 320

Ala Leu Leu Gln Ala His Ser Ile Arg Pro Asp Arg Tyr Thr Ile Leu
                325                 330                 335

Gly Asn Gly Leu Thr Leu Ser Ala Ala Glu Lys Val Ala Arg Ile Thr
            340                 345                 350

Lys Val Ile Asn
        355

<210> SEQ ID NO 58
<211> LENGTH: 356
<212> TYPE: PRT
<213> ORGANISM: Methanosarcina acetivorans

<400> SEQUENCE: 58

Met Lys Leu Thr Ile Asn Lys Asn Ser Ala Lys Trp Met Gln Leu Pro
1               5                   10                  15

Arg Asp Val Leu Val Gly His Gly Val Leu Glu Glu Ile Gly Asp Val
            20                  25                  30

Cys Arg Asp Leu Lys Leu Lys Gly Asn Ala Leu Ile Val Thr Gly Asn
        35                  40                  45

Thr Thr Arg Asp Val Ala Gly Lys Arg Val Ser Thr Leu Leu Glu Asn
    50                  55                  60

Ala Gly Ser Ser Thr Glu Met Val Leu Thr Cys Arg Ala Thr Met Glu
65                  70                  75                  80

Glu Val Asp Lys Ile Met Gln Lys Ala Ser Glu Thr Gly Ala Thr Phe
                85                  90                  95

Leu Leu Gly Ile Gly Ser Gly Arg Ser Ile Asp Leu Ala Lys Leu Ala
            100                 105                 110

Ser Thr Arg Leu Glu Ile Pro Phe Ile Ser Val Pro Thr Ala Ala Ser
        115                 120                 125

His Asp Gly Ile Ala Ser Ser Arg Ala Ser Ile Ile Asp Asn Gly Lys
    130                 135                 140

Asn Ala Ser Val Gln Ala Gln Ala Pro Ile Ala Val Val Ala Asp Thr
145                 150                 155                 160

Glu Ile Ile Ser Ala Ala Pro Phe Arg Phe Leu Val Ala Gly Cys Gly
                165                 170                 175

Asp Ile Ile Ser Asn Tyr Thr Ala Val Leu Asp Trp Glu Leu Ala Ser
            180                 185                 190

Arg Leu Arg Asn Glu Tyr Phe Gly Glu Tyr Ala Ala Ala Leu Ser Arg
        195                 200                 205

Met Ala Ala Arg Val Val Ile Glu Asn Ala Asp Ser Ile Lys Pro Glu
    210                 215                 220

His Glu Thr Ser Ala Arg Leu Val Val Lys Ala Leu Val Ser Asn Gly
225                 230                 235                 240

Val Ala Met Ser Ile Ala Gly Ser Ser Arg Pro Ala Ser Gly Ser Glu
                245                 250                 255

His Met Phe Ser His Ala Leu Asp Arg Ile Ala Pro Lys Pro Ala Leu
            260                 265                 270

His Gly Glu Gln Cys Gly Val Gly Thr Ile Met Met Met Tyr Leu His
```

```
            275                 280                 285
Gly Gly Asn Trp Gln Glu Ile Arg Asp Ala Leu Lys Lys Ile Gly Ala
        290                 295                 300

Pro Thr Asn Ala Glu Glu Leu Gly Ile Glu Asp Arg Tyr Ile Val Glu
305                 310                 315                 320

Ala Leu Leu His Ala His Ser Ile Arg Pro Asp Arg Tyr Thr Ile Leu
                325                 330                 335

Gly Asn Gly Leu Thr Pro Ser Ala Ala Glu Lys Val Ala Arg Ile Thr
            340                 345                 350

Lys Val Ile Ser
            355

<210> SEQ ID NO 59
<211> LENGTH: 353
<212> TYPE: PRT
<213> ORGANISM: Methanopyrus kandleri

<400> SEQUENCE: 59

Met Ser Val Pro Lys Lys Arg Met Gln Leu Pro Arg Glu Val Val Val
1               5                   10                  15

Gly Ser Asn Val Leu Pro Glu Val Pro Lys Leu Leu Arg Ser Val Gly
            20                  25                  30

Val Pro Asp Gly Val Val Ala Val Phe Ser Gly Arg Thr Thr Met Lys
        35                  40                  45

Ile Ala Gly Asn Glu Val Ala Asp His Leu Glu Glu Ala Gly Tyr Gln
    50                  55                  60

Thr Ser Pro Val Ile Val Lys Gly Ser Thr Gly Asp Asp Val Lys Lys
65                  70                  75                  80

Ala Leu Glu Ala Leu Asp Glu Ile Asp Ala Asp Val Val Ala Ala Val
                85                  90                  95

Gly Gly Gly Lys Val Ile Asp Val Ala Lys Val Ala Ser Tyr Arg Arg
            100                 105                 110

Gly Ile Pro Phe Ile Ser Val Pro Thr Ser Ala Ser His Asp Gly Ile
        115                 120                 125

Ala Ser Pro Phe Ala Ser Ile Arg Arg Glu Gly Arg Pro Tyr Ser Glu
    130                 135                 140

Pro Ala Gln Ala Pro Leu Ala Ile Leu Ala Asp Ile Glu Val Ile Arg
145                 150                 155                 160

Glu Ala Pro Glu Arg Leu Ile Arg Ala Gly Val Gly Asp Val Val Ser
                165                 170                 175

Asn Val Thr Ala Val Lys Asp Trp Arg Leu Ala His Arg Leu Arg Asn
            180                 185                 190

Glu Pro Tyr Ser Glu Tyr Ala Ser Ser Leu Ser Leu Met Ala Ala Arg
        195                 200                 205

Ile Val Met Lys Asn Ala Lys Pro Ile Gly Lys Leu Leu Pro Glu Gly
    210                 215                 220

Ile Lys Lys Leu Val Gln Ala Leu Ile Ser Gly Gly Val Ala Met Ser
225                 230                 235                 240

Ile Ala Gly Ser Ser Arg Pro Cys Ser Gly Ser Glu His Leu Phe Ser
                245                 250                 255

His Ala Leu Asp Val Ile Ala Glu Arg Pro Ala Leu His Gly Glu Gln
            260                 265                 270

Cys Gly Val Gly Thr Ile Ile Met Glu Tyr Leu His Gly Gly Asn Trp
        275                 280                 285
```

```
Arg Glu Ile Arg Glu Thr Leu Glu Thr Ala Gly Ala Pro Thr Thr Ala
    290                 295                 300

Glu Asp Leu Gly Val Ser Asp Glu Glu Ile Ile Glu Ala Leu Cys Arg
305                 310                 315                 320

Ala His Lys Ile Arg Pro Asp Arg Tyr Thr Ile Leu Gly Asp Lys Gly
                325                 330                 335

Leu Thr Arg Glu Ala Ala Glu Arg Ala Ala Glu Glu Thr Gly Val Ile
            340                 345                 350

Gln

<210> SEQ ID NO 60
<211> LENGTH: 351
<212> TYPE: PRT
<213> ORGANISM: Thermococcus kodakaraensis

<400> SEQUENCE: 60

Met Glu Arg Arg Ile His Leu Met Gln Leu Pro Arg Glu Val Leu Leu
1               5                   10                  15

Gly Glu Asn Leu Thr Gly Glu Val Val Ser Val Ala Lys Arg Ile Gly
            20                  25                  30

Leu Thr Gly Lys Ala Leu Val Ile Tyr Gly Pro Lys Thr Lys Glu Ile
        35                  40                  45

Ala Gly Arg Asp Val Glu Asp Ala Ile Lys Ser Ala Tyr Glu Val Ser
    50                  55                  60

Ser Leu Thr Ile Arg Lys Gly Ala Thr Met Glu Glu Val Glu Arg Thr
65                  70                  75                  80

Ile Glu Lys Ile Lys Asp Glu Gly Ile Gly Trp Val Ile Ala Val Gly
                85                  90                  95

Gly Gly Ser Ile Ile Asp Val Ala Lys Leu Ser Ser Phe Lys Thr Gly
            100                 105                 110

Val Pro Phe Ile Ser Phe Pro Thr Thr Ala Ser His Asp Gly Ile Ala
        115                 120                 125

Ser Ala Asn Ala Ser Ile Lys Asp Leu Gly Ser Lys Thr Ser Val Lys
    130                 135                 140

Ala Val Pro Pro Val Ala Val Ile Ala Asp Val Lys Val Ile Lys Thr
145                 150                 155                 160

Ala Pro Tyr Arg Tyr Leu Ala Ala Gly Val Gly Asp Thr Ile Ser Asn
                165                 170                 175

Leu Thr Ala Val Arg Asp Trp Gln Leu Ala His Arg Ile Lys Gly Glu
            180                 185                 190

Tyr Tyr Ser Glu Tyr Ala Ala Ser Leu Ser Leu Met Ser Ala Lys Met
        195                 200                 205

Val Met Arg Asn Ala Asp Ile Ile Arg Leu Gly Asn Glu Glu Ser Val
    210                 215                 220

Arg Lys Val Ile Lys Ala Leu Ile Ser Thr Gly Val Ala Met Ser Ile
225                 230                 235                 240

Ala Gly Ser Ser Arg Pro Ala Ser Gly Ala Glu His Leu Phe Ser His
                245                 250                 255

Ala Leu Asp Met Leu Asp Lys Pro Ala Leu His Gly Glu Gln Thr
            260                 265                 270

Gly Leu Gly Thr Ile Ile Met Ala Tyr Leu His Gly Met Lys Trp Glu
        275                 280                 285

Arg Val Arg Glu Thr Leu Lys Arg Val Gly Ala Pro Thr Asn Ala Tyr
    290                 295                 300
```

-continued

```
Glu Leu Gly Ile Asp Pro Glu Val Ile Ile Glu Ala Leu Thr Ile Ala
305                 310                 315                 320

His Thr Ile Arg Pro Glu Arg Tyr Thr Ile Leu Gly Lys Asp Gly Leu
            325                 330                 335

Thr Arg Glu Ala Ala Glu Lys Ala Ala Lys Ile Thr Gly Val Ile
        340                 345                 350

<210> SEQ ID NO 61
<211> LENGTH: 346
<212> TYPE: PRT
<213> ORGANISM: Pyrococcus furiosus

<400> SEQUENCE: 61

Met His Ile Met Glu Phe Pro Arg Glu Val Ile Leu Gly Lys Asn Val
1               5                   10                  15

Ile Ser Glu Thr Val Asn Val Ala Lys Arg Leu Ser Phe Ser Ser Pro
            20                  25                  30

Val Leu Val Val Tyr Gly Pro Lys Thr Lys Glu Ile Ala Gly Lys Asp
        35                  40                  45

Val Glu Arg Val Leu Lys Glu Glu Phe Asp Val His Ser Val Ile Val
    50                  55                  60

Lys Glu Ala Thr Ile Asn Glu Val Lys Val Glu Gly Ile Ile Arg
65                  70                  75                  80

Asp Asn Lys Val Lys Trp Ala Ile Ala Val Gly Gly Gly Thr Ile Ile
                85                  90                  95

Asp Val Thr Lys Leu Ala Ser Tyr Arg Ala Gly Ile Pro Phe Val Ser
            100                 105                 110

Phe Pro Thr Thr Ala Ser His Asp Gly Ile Ala Ser Ala Asn Ala Ser
        115                 120                 125

Ile Lys Gly Leu Gly Thr Lys Thr Ser Ile Lys Ala Arg Pro Pro Val
    130                 135                 140

Ala Val Ile Ala Asp Ile Arg Ile Ile Lys Ser Ala Pro Arg Arg Tyr
145                 150                 155                 160

Leu Ala Ala Gly Val Gly Asp Val Ile Ser Asn Ile Thr Ala Val Arg
                165                 170                 175

Asp Trp Lys Leu Ala His Lys Ile Lys Gly Glu Tyr Phe Ser Glu Tyr
            180                 185                 190

Ala Ala Ala Leu Ser Leu Met Ser Ala Lys Met Val Met Arg Asp Ala
        195                 200                 205

Glu Ile Ile Arg Ile Gly Asp Asp Glu Gly Val Arg Lys Val Val Lys
    210                 215                 220

Ala Leu Ile Ser Ser Gly Val Ala Met Ser Ile Ala Gly Ser Ser Arg
225                 230                 235                 240

Pro Ala Ser Gly Ala Glu His Leu Phe Ser His Ala Leu Asp Leu Leu
                245                 250                 255

Leu Glu Lys Pro Ala Leu His Gly Glu Gln Thr Gly Ile Gly Thr Ile
            260                 265                 270

Ile Met Ala Tyr Leu His Gly Ile Asn Trp Arg Lys Ile Lys Glu Thr
        275                 280                 285

Leu Gln Lys Val Gly Ala Pro Thr Thr Ala Tyr Glu Leu Gly Val Asp
    290                 295                 300

Pro Glu Ile Ile Ile Glu Ala Leu Thr Ile Ala His Thr Ile Arg Pro
305                 310                 315                 320

Glu Arg Tyr Thr Ile Leu Gly Arg Asp Gly Leu Thr Arg Glu Ala Ala
                325                 330                 335
```

Glu Arg Ala Ala Lys Ile Thr Gly Val Ile
            340             345

<210> SEQ ID NO 62
<211> LENGTH: 346
<212> TYPE: PRT
<213> ORGANISM: Pyrococcus horikoshii

<400> SEQUENCE: 62

Met His Leu Met Glu Phe Pro Arg Glu Val Ile Leu Gly Lys Asn Leu
1               5                   10                  15

Ile Gln Glu Ile Asn Asn Val Ile Lys Arg Leu Lys Leu Gly Ser Pro
            20                  25                  30

Gly Leu Val Val Tyr Gly Pro Ile Thr Lys Lys Ile Ala Gly Ser Asn
        35                  40                  45

Val Glu Lys Ile Val Lys Glu Glu Phe Glu Val Tyr Ser Ile Thr Val
    50                  55                  60

Lys Glu Ala His Ile Asn Glu Val Glu Arg Val Ile Ser Lys Ile Arg
65                  70                  75                  80

Asp Lys Gly Ile Lys Trp Ala Ile Ala Val Gly Gly Ser Ile Ile
                85                  90                  95

Asp Val Thr Lys Leu Ala Ser Phe Lys Met Gly Ile Pro Phe Ile Ser
            100                 105                 110

Phe Pro Thr Thr Ala Ser His Asp Gly Ile Ala Ser Ala Asn Ala Ser
        115                 120                 125

Ile Lys Gly Leu Asn Val Lys Thr Ser Ile Lys Ala Lys Pro Pro Ile
    130                 135                 140

Ala Val Ile Ala Asp Ile Asp Val Ile Lys Thr Ala Pro Lys Arg Tyr
145                 150                 155                 160

Leu Ala Ala Gly Val Gly Asp Ile Val Ser Asn Ile Thr Ala Val Arg
                165                 170                 175

Asp Trp Lys Leu Ala His Lys Leu Lys Gly Tyr Phe Ser Glu Tyr
            180                 185                 190

Ala Ala Ser Leu Ser Leu Met Ser Ala Lys Met Val Ile Arg Asp Ala
        195                 200                 205

Glu Ile Ile Arg Leu Gly Gln Asp Glu Gly Ile Arg Lys Val Val Lys
    210                 215                 220

Ala Leu Ile Ser Ser Gly Val Ala Met Ser Ile Ala Gly Ser Ser Arg
225                 230                 235                 240

Pro Ala Ser Gly Ala Glu His Leu Phe Ser His Ala Leu Asp Met Leu
                245                 250                 255

Leu Asp Lys Pro Ala Leu His Gly Glu Gln Thr Gly Ile Gly Thr Ile
            260                 265                 270

Ile Met Ala Tyr Leu His Gly Ile Asn Trp Lys Lys Ile Arg Asp Thr
        275                 280                 285

Leu Lys Ile Val Gly Ala Pro Thr Thr Ala Tyr Glu Leu Gly Ile Asp
    290                 295                 300

Pro Glu Ile Ile Ile Glu Ala Leu Thr Ile Ala His Thr Ile Arg Pro
305                 310                 315                 320

Glu Arg Tyr Thr Ile Leu Gly Lys Gly Ile Thr Arg Glu Ala Ala
                325                 330                 335

Glu Lys Ala Ala Lys Ile Thr Gly Val Ile
            340                 345

<210> SEQ ID NO 63
<211> LENGTH: 346
<212> TYPE: PRT
<213> ORGANISM: Pyrococcus abyssi

<400> SEQUENCE: 63

Met His Leu Met Glu Phe Pro Arg Glu Val Ile Leu Gly Lys Asn Leu
1               5                   10                  15

Val Pro Glu Val Asn Asn Val Ile Lys Arg Leu Lys Leu Glu Ser Pro
            20                  25                  30

Gly Leu Val Val Tyr Gly Pro Val Thr Lys Lys Ile Ala Gly Glu Ser
        35                  40                  45

Val Lys Lys Ala Ile Arg Asp Glu Phe Asp Val Tyr Ser Ile Thr Val
50                  55                  60

Lys Lys Ala His Ile Gly Glu Val Glu Lys Val Glu Ala Lys Ile Arg
65                  70                  75                  80

Asp Tyr Asn Ile Lys Trp Ala Ile Ala Val Gly Gly Ser Ile Ile
                85                  90                  95

Asp Val Thr Lys Leu Ala Ser Tyr Arg Ser Gly Ile Pro Phe Ile Ser
            100                 105                 110

Phe Pro Thr Thr Ala Ser His Asp Gly Ile Ala Ser Ala Asn Ala Ser
            115                 120                 125

Ile Arg Gly Ile Glu Ala Lys Thr Ser Ile Lys Ala Arg Pro Pro Ile
130                 135                 140

Ala Val Ile Ala Asp Ile Glu Val Ile Lys Thr Ala Pro Arg Arg Tyr
145                 150                 155                 160

Leu Ala Ala Gly Val Gly Asp Val Ile Ser Asn Ile Thr Ala Val Arg
                165                 170                 175

Asp Trp Lys Leu Ala His Lys Leu Lys Gly Glu Tyr Phe Ser Glu Tyr
            180                 185                 190

Ala Ala Ala Leu Ser Leu Met Ser Ala Lys Met Val Ile Arg Asp Ala
            195                 200                 205

Glu Ile Ile Arg Leu Gly Asn Asp Glu Gly Val Arg Lys Val Ile Lys
210                 215                 220

Ala Leu Ile Ser Ser Gly Val Ala Met Ser Ile Ala Gly Ser Ser Arg
225                 230                 235                 240

Pro Ala Ser Gly Ala Glu His Leu Phe Ser His Ala Leu Asp Leu Leu
                245                 250                 255

Leu Asp Lys Pro Ala Leu His Gly Glu Gln Thr Gly Ile Gly Thr Ile
            260                 265                 270

Ile Met Ala Tyr Leu His Gly Ile Asn Trp Arg Lys Ile Lys Glu Thr
            275                 280                 285

Leu Lys Thr Val Gly Ala Pro Thr Ser Ala Tyr Glu Leu Gly Ile Asp
        290                 295                 300

Pro Glu Ile Ile Glu Ala Leu Thr Ile Ala His Lys Ile Arg Pro
305                 310                 315                 320

Glu Arg Tyr Thr Ile Leu Gly Lys Glu Gly Leu Thr Arg Glu Ala Ala
                325                 330                 335

Glu Lys Ala Ala Lys Ile Thr Gly Val Ile
            340                 345

<210> SEQ ID NO 64
<211> LENGTH: 370
<212> TYPE: PRT
<213> ORGANISM: Geobacillus stearothermophilus

```
<400> SEQUENCE: 64

Met Ala Ala Glu Arg Val Phe Ile Ser Pro Ala Lys Tyr Val Gln Gly
1               5                   10                  15

Lys Asn Val Ile Thr Lys Ile Ala Asn Tyr Leu Glu Gly Ile Gly Asn
            20                  25                  30

Lys Thr Val Val Ile Ala Asp Glu Ile Val Trp Lys Ile Ala Gly His
        35                  40                  45

Thr Ile Val Asn Glu Leu Lys Lys Gly Asn Ile Ala Ala Glu Glu Val
    50                  55                  60

Val Phe Ser Gly Glu Ala Ser Arg Asn Glu Val Glu Arg Ile Ala Asn
65                  70                  75                  80

Ile Ala Arg Lys Ala Glu Ala Ala Ile Val Ile Gly Val Gly Gly Gly
                85                  90                  95

Lys Thr Leu Asp Thr Ala Lys Ala Val Ala Asp Glu Leu Asp Ala Tyr
            100                 105                 110

Ile Val Ile Val Pro Thr Ala Ala Ser Thr Asp Ala Pro Thr Ser Ala
        115                 120                 125

Leu Ser Val Ile Tyr Ser Asp Asp Gly Val Phe Glu Ser Tyr Arg Phe
    130                 135                 140

Tyr Lys Lys Asn Pro Asp Leu Val Leu Val Asp Thr Lys Ile Ile Ala
145                 150                 155                 160

Asn Ala Pro Pro Arg Leu Leu Ala Ser Gly Ile Ala Asp Ala Leu Ala
                165                 170                 175

Thr Trp Val Glu Ala Arg Ser Val Ile Lys Ser Gly Lys Thr Met
            180                 185                 190

Ala Gly Gly Ile Pro Thr Ile Ala Ala Glu Ile Ala Glu Lys Cys
        195                 200                 205

Glu Gln Thr Leu Phe Lys Tyr Gly Lys Leu Ala Tyr Glu Ser Val Lys
    210                 215                 220

Ala Lys Val Val Thr Pro Ala Leu Glu Ala Val Glu Ala Asn Thr
225                 230                 235                 240

Leu Leu Ser Gly Leu Gly Phe Glu Ser Gly Gly Leu Ala Ala His
            245                 250                 255

Ala Ile His Asn Gly Phe Thr Ala Leu Glu Gly Glu Ile His His Leu
        260                 265                 270

Thr His Gly Glu Lys Val Ala Phe Gly Thr Leu Val Gln Leu Ala Leu
    275                 280                 285

Glu Glu His Ser Gln Gln Glu Ile Glu Arg Tyr Ile Glu Leu Tyr Leu
290                 295                 300

Ser Leu Asp Leu Pro Val Thr Leu Glu Asp Ile Lys Leu Lys Asp Ala
305                 310                 315                 320

Ser Arg Glu Asp Ile Leu Lys Val Ala Lys Ala Thr Ala Glu Gly
            325                 330                 335

Glu Thr Ile His Asn Ala Phe Asn Val Thr Ala Asp Asp Val Ala Asp
        340                 345                 350

Ala Ile Phe Ala Ala Asp Gln Tyr Ala Lys Ala Tyr Lys Glu Lys His
    355                 360                 365

Arg Lys
    370

<210> SEQ ID NO 65
<211> LENGTH: 365
<212> TYPE: PRT
<213> ORGANISM: Citrobacter freundii
```

<400> SEQUENCE: 65

Met Leu Lys Val Ile Gln Ser Pro Ala Lys Tyr Leu Gln Gly Pro Asp
1               5                   10                  15

Ala Ser Thr Leu Phe Gly Gln Tyr Ala Lys Asn Leu Ala Asp Ser Phe
            20                  25                  30

Phe Val Ile Ala Asp Asp Phe Val Met Lys Leu Ala Gly Glu Lys Val
        35                  40                  45

Leu Asn Gly Leu His Ser His Asp Ile Ser Cys His Ala Glu Arg Phe
    50                  55                  60

Asn Gly Glu Cys Ser His Ile Glu Ile Asn Arg Leu Ile Ala Ile Leu
65                  70                  75                  80

Lys Gln His Gly Cys Arg Gly Val Val Gly Ile Gly Gly Lys Thr
                85                  90                  95

Leu Asp Thr Ala Lys Ala Ile Gly Tyr Tyr Gln Lys Leu Pro Val Val
            100                 105                 110

Val Ile Pro Thr Ile Ala Ser Thr Asp Ala Pro Thr Ser Ala Leu Ser
        115                 120                 125

Val Ile Tyr Thr Glu Ala Gly Glu Phe Glu Tyr Leu Ile Tyr Pro
130                 135                 140

Lys Asn Pro Asp Met Val Val Met Asp Thr Ala Ile Ile Ala Lys Ala
145                 150                 155                 160

Pro Val Arg Leu Leu Val Ala Gly Met Gly Asp Ala Leu Ser Thr Trp
                165                 170                 175

Phe Glu Ala Lys Ala Cys Tyr Asp Ala Arg Ala Thr Ser Met Ala Gly
            180                 185                 190

Gly Gln Ser Thr Val Ala Ala Leu Ser Leu Ala Arg Leu Cys Tyr Asp
        195                 200                 205

Thr Leu Leu Ala Glu Gly Glu Lys Ala Arg Phe Ala Ala Gln Ala Gly
210                 215                 220

Val Val Thr Asp Ala Leu Glu Arg Ile Val Glu Ala Asn Thr Tyr Leu
225                 230                 235                 240

Ser Gly Ile Gly Phe Glu Ser Ser Gly Leu Ala Gly Ala His Ala Ile
                245                 250                 255

His Asn Gly Phe Thr Ile Leu Glu Glu Cys His His Leu Tyr His Gly
            260                 265                 270

Glu Lys Val Ala Phe Gly Thr Leu Ala Gln Leu Val Leu Gln Asn Ser
        275                 280                 285

Pro Met Glu Glu Ile Glu Thr Val Leu Asn Phe Cys Gln Lys Val Gly
    290                 295                 300

Leu Pro Val Thr Leu Ala Glu Met Gly Val Lys Asp Asp Ile Asp Gly
305                 310                 315                 320

Lys Ile Met Ala Val Ala Lys Ala Thr Cys Ala Glu Gly Glu Thr Ile
                325                 330                 335

His Asn Met Pro Phe Ser Val Thr Pro Glu Ser Val His Ala Ala Ile
            340                 345                 350

Leu Thr Ala Asp Leu Leu Gly Gln Gln Trp Leu Ala Arg
        355                 360                 365

<210> SEQ ID NO 66
<211> LENGTH: 367
<212> TYPE: PRT
<213> ORGANISM: Escherichia coli O6:H1

<400> SEQUENCE: 66

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Lys Thr
                85                  90                  95

Leu Asp Thr Ala Lys Ala Leu Ala His Phe Met Gly Val Pro Val Ala
                100                 105                 110

Ile Ala Pro Thr Ile Ala Ser Thr Asp Ala Pro Cys Ser Ala Leu Ser
            115                 120                 125

Val Ile Tyr Thr Asp Glu Gly Glu Phe Asp Arg Tyr Leu Leu Leu Pro
        130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
                180                 185                 190

Gly Lys Cys Thr Gln Ala Ala Leu Ala Leu Ala Glu Leu Cys Tyr Asn
                195                 200                 205

Thr Leu Leu Glu Glu Gly Glu Lys Ala Met Leu Ala Ala Glu Gln His
            210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr His Gly
                260                 265                 270

Glu Lys Val Ala Phe Gly Thr Leu Thr Gln Leu Val Leu Glu Asn Ala
                275                 280                 285

Pro Val Glu Glu Ile Glu Thr Val Ala Ala Leu Ser His Ala Val Gly
                290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
                340                 345                 350

Leu Val Ala Asp Gln Tyr Gly Gln Arg Phe Leu Gln Glu Trp Glu
                355                 360                 365

<210> SEQ ID NO 67
<211> LENGTH: 365
<212> TYPE: PRT
<213> ORGANISM: Pseudomonas putida

<400> SEQUENCE: 67

Met Asp Arg Ala Ile Gln Ser Pro Gly Lys Tyr Val Gln Gly Ala Asp

```
            1               5                   10                  15
        Ala Leu Gln Arg Leu Gly Asp Tyr Leu Lys Pro Leu Ala Asp Ser Trp
                        20                  25                  30
        Leu Val Ile Ala Asp Lys Phe Val Leu Gly Phe Ala Glu Asp Thr Ile
                        35                  40                  45
        Arg Gln Ser Leu Ser Lys Ala Gly Leu Ala Met Asp Ile Val Ala Phe
                        50                  55                  60
        Asn Gly Glu Cys Ser Gln Gly Glu Val Asp Arg Leu Cys Gln Leu Ala
         65                     70                  75                  80
        Thr Gln Asn Gly Arg Ser Ala Ile Val Gly Ile Gly Gly Lys Thr
                            85                  90                  95
        Leu Asp Thr Ala Lys Ala Val Ala Phe Phe Gln Lys Val Pro Val Ala
                        100                 105                 110
        Val Ala Pro Thr Ile Ala Ser Thr Asp Ala Pro Cys Ser Ala Leu Ser
                        115                 120                 125
        Val Leu Tyr Thr Asp Glu Gly Glu Phe Asp Arg Tyr Leu Met Leu Pro
                        130                 135                 140
        Thr Asn Pro Ala Leu Val Val Asp Thr Ala Ile Val Ala Arg Ala
        145                 150                 155                 160
        Pro Ala Arg Leu Leu Ala Ala Gly Ile Gly Asp Ala Leu Ala Thr Trp
                            165                 170                 175
        Phe Glu Ala Arg Ala Ala Ser Arg Ser Ser Ala Ala Thr Met Ala Gly
                        180                 185                 190
        Gly Pro Ala Thr Gln Thr Ala Leu Asn Leu Ala Arg Phe Cys Tyr Asp
                        195                 200                 205
        Thr Leu Leu Glu Glu Gly Glu Lys Ala Met Leu Ala Val Gln Ala Gln
        210                 215                 220
        Val Val Thr Pro Ala Leu Glu Arg Ile Val Glu Ala Asn Thr Tyr Leu
        225                 230                 235                 240
        Ser Gly Val Gly Phe Glu Ser Gly Gly Val Ala Ala Ala His Ala Val
                            245                 250                 255
        His Asn Gly Leu Thr Ala Val Ala Glu Thr His His Phe Tyr His Gly
                        260                 265                 270
        Glu Lys Val Ala Phe Gly Val Leu Val Gln Leu Ala Leu Glu Asn Ala
                        275                 280                 285
        Ser Asn Ala Glu Met Gln Glu Val Met Ser Leu Cys His Ala Val Gly
                        290                 295                 300
        Leu Pro Ile Thr Leu Ala Gln Leu Asp Ile Thr Glu Asp Ile Pro Thr
        305                 310                 315                 320
        Lys Met Arg Ala Val Ala Glu Leu Ala Cys Ala Pro Gly Glu Thr Ile
                        325                 330                 335
        His Asn Met Pro Gly Gly Val Thr Val Glu Gln Val Tyr Gly Ala Leu
                        340                 345                 350
        Leu Val Ala Asp Gln Leu Gly Gln His Phe Leu Glu Phe
                        355                 360                 365

<210> SEQ ID NO 68
<211> LENGTH: 362
<212> TYPE: PRT
<213> ORGANISM: Escherichia coli (strain K12)

<400> SEQUENCE: 68

Met Pro His Asn Pro Ile Arg Val Val Val Gly Pro Ala Asn Tyr Phe
  1               5                  10                  15
```

Ser His Pro Gly Ser Phe Asn His Leu His Asp Phe Phe Thr Asp Glu
            20                  25                  30

Gln Leu Ser Arg Ala Val Trp Ile Tyr Gly Lys Arg Ala Ile Ala Ala
        35                  40                  45

Ala Gln Thr Lys Leu Pro Pro Ala Phe Gly Leu Pro Gly Ala Lys His
    50                  55                  60

Ile Leu Phe Arg Gly His Cys Ser Glu Ser Asp Val Gln Gln Leu Ala
65                  70                  75                  80

Ala Glu Ser Gly Asp Asp Arg Ser Val Val Ile Gly Val Gly Gly Gly
                85                  90                  95

Ala Leu Leu Asp Thr Ala Lys Ala Leu Ala Arg Arg Leu Gly Leu Pro
            100                 105                 110

Phe Val Ala Val Pro Thr Ile Ala Ala Thr Cys Ala Ala Trp Thr Pro
        115                 120                 125

Leu Ser Val Trp Tyr Asn Asp Ala Gly Gln Ala Leu His Tyr Glu Ile
    130                 135                 140

Phe Asp Asp Ala Asn Phe Met Val Leu Val Glu Pro Glu Ile Ile Leu
145                 150                 155                 160

Asn Ala Pro Gln Gln Tyr Leu Leu Ala Gly Ile Gly Asp Thr Leu Ala
                165                 170                 175

Lys Trp Tyr Glu Ala Val Val Leu Ala Pro Gln Pro Glu Thr Leu Pro
            180                 185                 190

Leu Thr Val Arg Leu Gly Ile Asn Asn Ala Gln Ala Ile Arg Asp Val
        195                 200                 205

Leu Leu Asn Ser Ser Glu Gln Ala Leu Ser Asp Gln Gln Asn Gln Gln
210                 215                 220

Leu Thr Gln Ser Phe Cys Asp Val Val Asp Ala Ile Ile Ala Gly Gly
225                 230                 235                 240

Gly Met Val Gly Gly Leu Gly Asp Arg Phe Thr Arg Val Ala Ala Ala
                245                 250                 255

His Ala Val His Asn Gly Leu Thr Val Leu Pro Gln Thr Glu Lys Phe
            260                 265                 270

Leu His Gly Thr Lys Val Ala Tyr Gly Ile Leu Val Gln Ser Ala Leu
        275                 280                 285

Leu Gly Gln Asp Asp Val Leu Ala Gln Leu Thr Gly Ala Tyr Gln Arg
    290                 295                 300

Phe His Leu Pro Thr Thr Leu Ala Glu Leu Glu Val Asp Ile Asn Asn
305                 310                 315                 320

Gln Ala Glu Ile Asp Lys Val Ile Ala His Thr Leu Arg Pro Val Glu
                325                 330                 335

Ser Ile His Tyr Leu Pro Val Thr Leu Thr Pro Asp Thr Leu Arg Ala
            340                 345                 350

Ala Phe Lys Lys Val Glu Ser Phe Lys Ala
        355                 360

<210> SEQ ID NO 69
<211> LENGTH: 385
<212> TYPE: PRT
<213> ORGANISM: Synechocystis sp.

<400> SEQUENCE: 69

Met Ala Pro Ser Ile Ser Pro Val Thr Gln Pro Leu Val Ser Met Ala
1               5                   10                  15

Ile Ala Pro Thr Val Val Ile Arg Ser Ala Leu Ala Lys Ala Gly Glu
            20                  25                  30

His Leu Gln Lys Leu Gly Ser Lys Gly Leu Val Val Thr Gly Ser His
          35                  40                  45

Ser Ala Glu Leu Gly Glu Lys Ser Leu Gln Thr Leu Gln Lys Asn Tyr
 50                  55                  60

Gly Leu Thr Leu Pro Leu Ala Ser Tyr Leu Pro Asp Cys Ala Glu Ser
 65                  70                  75                  80

Ser Leu Glu Gln Leu Arg Arg Val His Gln Glu Gln Pro Asp Phe
                 85                  90                  95

Ile Leu Gly Ile Gly Gly Lys Ala Leu Asp Thr Ala Lys Leu Leu
            100                 105                 110

Ala His Gln Thr Gln Leu Ala Ile Ala Thr Val Pro Thr Ser Ala Ala
            115                 120                 125

Thr Cys Ala Gly Trp Thr Ala Leu Ala Asn Val Tyr Ser Glu Thr Gly
            130                 135                 140

Ala Phe Arg Tyr Asp Val Ala Leu Asp Arg Cys Pro Asp Leu Leu Ile
145                 150                 155                 160

Val Asp Tyr Glu Leu Ile Gln Arg Ala Glu Pro Arg Leu Leu Val Ala
                165                 170                 175

Gly Ile Gly Asp Ala Ile Ala Lys Trp Tyr Glu Ala Ser Val Ser Ser
                180                 185                 190

Gly Gln Ser Ser Asp Thr Phe Thr Val Ala Ala Val Gln Gln Ala Arg
            195                 200                 205

Ile Leu Arg Asp Ile Leu Phe Gln Lys Ser Ala Glu Ala Leu Ala Gln
            210                 215                 220

Pro Gly Ser Glu Thr Trp Arg Glu Val Val Asp Ala Ser Leu Leu Met
225                 230                 235                 240

Ala Gly Val Ile Gly Gly Leu Gly Gly Ala Asn Cys Arg Thr Val Ala
                245                 250                 255

Ala His Ala Val His Asn Gly Leu Thr Gln Leu Pro Gln Ala His His
            260                 265                 270

Ala Leu His Gly Glu Lys Val Ala Tyr Gly Ile Leu Val Gln Leu Arg
            275                 280                 285

Leu Glu Glu Leu Val Ser Gly Asn Gln Leu Ala Ala Thr Ala Arg Arg
            290                 295                 300

Gln Leu Leu Ser Phe Tyr Asp Glu Ile Gly Leu Pro Lys Thr Leu Gln
305                 310                 315                 320

Asp Leu Gly Leu Gly Arg Ile Ser Leu Glu Glu Leu Arg Gln Thr Ala
                325                 330                 335

Glu Phe Thr Cys Leu Pro Asn Ser Asp Ile His Arg Leu Pro Phe Thr
                340                 345                 350

Val Thr Pro Glu Thr Leu Met Ala Ala Met Val Ser Thr Leu Val Glu
            355                 360                 365

Glu Gln Gly Thr Arg Gln Leu Phe Ala Gln Ile Gln Asp Asn Ser Gly
            370                 375                 380

Leu
385

MUTANT GLYCEROL DEHYDROGENASE (GLYDH) FOR THE PRODUCTION OF A BIOCHEMICAL BY FERMENTATION

CROSS REFERENCE TO RELATED APPLICATIONS

This application is a §371 National Stage Application of PCT/EP2010/061129, filed Jul. 30, 2010, which claims priority to European Application No. 09166812.9, filed Jul. 30, 2009 and U.S. Provisional Application No. 61/229,775, filed Jul. 30, 2009.

REFERENCE TO THE SEQUENCE LISTING SUBMITTED ELECTRONICALLY

The official copy of the sequence listing is submitted electronically via EFS-Web as an ASCII-formatted sequence listing with a file named "360241 D27716 ST25 amended sequence listing.txt" created on Oct. 6, 2014, and having a size of 85 kilobytes. The sequence listing contained in this ASCII-formatted document is part of the specification and is herein incorporated by reference in its entirety.

BACKGROUND OF THE INVENTION

1. Field of the Invention

The present invention concerns a method for the production of 1,2-propanediol, comprising culturing a microorganism modified for an improved production of 1,2-propanediol in an appropriate culture medium and recovery of the 1,2-propanediol which may be further purified wherein the microorganism expresses a glycerol dehydrogenase (GlyDH) enzyme, the inhibition of which activity by NAD+ and/or its substrate and/or its product is reduced.

The present invention also relates to a mutant glycerol dehydrogenase(GlyDH) comprising at least one amino acid residue in the protein sequence of the parent enzyme replaced by a different amino acid residue at the same position wherein
   the mutant enzyme has retained more than 50% of the glycerol dehydrogenase activity of the parent enzyme and
   the glycerol dehydrogenase activity of the mutant GlyDH is less inhibited by NAD+ and/or by its substrate as compared to the parent enzyme and/or by its product as compared to the parent enzyme.

2. Description of Related Art

Glycerol dehydrogenase (GlyDH) was first isolated and partially purified from *E. coli* by Asnis and Broadie (1953) as a relatively heat-stable enzyme. This enzyme catalysed the oxidation of glycerol into dihydroxyacetone in a 1:1 molar ratio with the help of nicotinamide co-factor according to the following reversible equation:

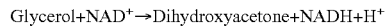

Glycerol+NAD$^+$→Dihydroxyacetone+NADH+H$^+$

GlyDH was then purified to homogeneity both from *E. coli* (Tang et al, 1979, Kelley and Dekker, 1984) and from other organisms (Lin and Magasanik, 1960, McGregor et al, 1974), especially *Aerobacter aerogenes* (later renamed *Klebsiella pneumoniae*). The properties of GlyDH from both organisms were similar: the pH optimum for the oxidation reduction was in the alkaline region (9 to 10) whereas the pH for the reduction reaction was about 6; the enzyme was inhibited by zinc ion and chelating agents. In addition, this enzyme was shown to be activated by monovalent cations, especially ammonium ion.

The range of substrate was later extended for commercially available GlyDH from *Enterobacter aerogenes* and *Cellulomonas* sp. (Lee and Whitesides, 1985) as well as for *E. coli* GlyDH (Subedi et al, 2007): GlyDH was active in the reduction of several aldehydes and ketones including in addition of dihydroxyacetone: glyceraldehyde, glycolaldehyde, hydroxyacetone (acetol), methylglyoxal and lactaldehyde. For the oxidation reaction, in addition to glycerol, the enzyme was active on several chiral 1,2-diols including 1,2-ethanediol, 1,2-propanediol, 1,2-butanediol and derivatives (chloro-, amino-), but also on 2,3-butanediol. The enzyme was shown to be stereo-specific for (R) diols. Based on affinity data (affinity constant Km), the best substrates for reduction reaction are, in this order, hydroxyacetone, dihydroxyacetone, methylglyoxal and glycolaldehyde (Nishise et al, 1984, Lee and Whitesides, 1985, Subedi et al, 2007). For the oxidation reduction, the best substrates are 1,2-propanediol, 1,2-butanediol, glycerol, 2,3-butanediol and 1,2-ethanediol (Nishise et al, 1984, Kelley and Dekker, 1984, Lee and Whitesides, 1985).

GlyDH from *Bacillus stearothermophilus* was purified (Spencer et al, 1989) and later crystallised for determination of the tri-dimensional structure (Ruzheinikov et al, 2001). This enzyme was shown to contain 1 mole of zinc located in the active site per mole of enzyme subunit whereas the GlyDH from Enterobacteria seem to be Fe-dependent enzymes. The other properties of the enzyme concerning catalysis were similar to those of the previously described GlyDH. The enzyme was a multimer composed of 8 identical subunits as was already postulated for GlyDH from *Cellulomonas* (Nishise et al, 1984) and *E. coli* (Kelley and Dekker, 1984).

Product inhibition studies with glycerol as substrate were carried out in order to understand the mechanism of the enzymatic reaction catalysed by GlyDH (McGregor et al, 1974, Nishise et al, 1984):
   NADH was shown to be a competitive inhibitor against NAD+
   NADH was shown to be a non-competitive inhibitor against glycerol
   Dihydroxyacetone was shown to be a non-competitive inhibitor against both substrates, NAD+ and glycerol.

Such an inhibition pattern was only compatible with an ordered Bi Bi mechanism in which NAD+ was bound first to the enzyme, then glycerol was bound and dihydroxyacetone was released first and NADH was released last. The same inhibition pattern is applicable for the reduction reaction with the substrates dihydroxyacetone and NADH. In addition, substrate inhibition was shown by Nishise et al (1984) with hydroxyacetone or dihydroxyacetone.

The gene coding for GlyDH was only identified recently, in *Bacillus stearothermophilus* (Mallinder et al, 1991) and in *E. coli* (gldA gene, Truninger and Boos, 1994). Several GlyDH mutants have been obtained and characterized but none was shown to have alternative properties regarding inhibition.

Two metabolic pathways for assimilation of glycerol have been identified in microorganisms:
   The first one is a respiratory pathway active in the presence of electron acceptor and involving a glycerol transporter, a glycerol kinase and two respiratory glycerol-3-phosphate dehydrogenase. Glycerol-3-phosphate is the intermediate in the pathway which ended in dihydroxyacetone phosphate DHAP that can enter the central metabolism.
   The second pathway can be active under strict anaerobic conditions in the absence of electron acceptors and involves as first step GlyDH converting glycerol into DHA (dihydroxyacetone). DHA is then phosphorylated to generate DHAP.

The main function of GlyDH was then associated with glycerol utilization. However, as mentioned before, glycerol is not the best substrate for this enzyme and GlyDH was utilized later for production of 1,2-propanediol by fermentation in recombinant organisms (Altaras and Cameron, 1999, WO 98/37204). By deleting the gldA gene in *E. coli*, a strain that was not able to produce 1,2-propanediol but accumulated hydroxyacetone instead was obtained (WO 2008/116851). This highlighted the role of GlyDH as the only enzyme active in *E. coli* in the conversion of hydroxyacetone into 1,2-propanediol.

GlyDHs have been used in bioconversion processes to obtain optically active diols from their carbonyl precursors, particularly halopropanediol derivatives from halohydroxyacetone derivatives (e.g. (R) or (S)-3-chloro-1,2-propanediol, useful as pharmaceutical intermediates) in WO03/01853, WO2005/123921, JP2003/061668 and JP2005/013028. GlyDHs from *Cellulomonas* sp., *Serratia marcescens, Aeropyrum pernix* and mutant GlyDHs from *Aeropyrum pernix* have been used. However, bioconversion processes where complex precursors are used to produce complex molecules in one enzymatic step (using isolated enzymes or microorganisms) are clearly distinct from fermentation processes where a carbon source is converted to a structurally non-related product using the whole metabolic equipment (i.e. many enzymes arranged in metabolic pathways) of the microorganism.

Production of 1,2-propanediol can result from the catabolism of different substrates (glucose, fructose, sucrose, glycerol) through the central metabolism of different microorganisms. The biosynthetic pathway to 1,2-propanediol starts from the glycolysis intermediate dihydroxyacetone phosphate. This metabolic intermediate can be converted to methylglyoxal by methylglyoxal synthase (Cooper, 1984, Tötemeyer et al, 1998). Methylglyoxal is an extremely toxic electrophile that can react with nucleophilic centres of macromolecules such as DNA, RNA and proteins. It can inhibit bacterial growth and cause cell death at very low concentrations (0.3 to 0.7 mM). For this reason, the existing routes for detoxification of methylglyoxal have been investigated (Ferguson et al, 1998). Three pathways have been identified in bacteria and specifically in *E. coli*:

The first one is the gluthatione dependent glyoxalase I-II system which converts methylglyoxal into D-lactate in two steps.

The second one is the glutathione independent glyoxalase III enzyme which catalyses the conversion of methylglyoxal into D-lactate (Misra et al, 1995).

The third system encompasses the degradation of methylglyoxal by methylglyoxal reductases.

This last system is relevant for the production of 1,2-propanediol. Methylglyoxal is a C3 ketoaldehyde, bearing an aldehyde at C1 and a ketone at C2. Theses two positions can be reduced to alcohol, yielding respectively acetol (or hydroxyacetone), a non-chiral molecule and lactaldehyde, a chiral molecule which can exist in L- or D-form. These 3 molecules, acetol, L-lactaldehyde and D-lactaldehyde can be subsequently reduced at the other position to yield chiral 1,2-propanediol (Cameron et al, 1998, Bennett and San, 2001).

1,2-propanediol or propylene glycol, a C3 dialcohol, is a widely-used chemical. It is a component of unsaturated polyester resins, liquid detergents, coolants, anti-freeze and de-icing fluids for aircraft. Propylene glycol has been increasingly used since 1993-1994 as a replacement for ethylene derivatives, which are recognised as being more toxic than propylene derivatives.

1,2-propanediol is currently produced by chemical means using a propylene oxide hydration process that consumes large amounts of water. Propylene oxide can be produced by either of two processes, one using epichlorhydrin, and the other hydroperoxide. Both routes use highly toxic substances. In addition, the hydroperoxide route generates by-products such as tert-butanol and 1-phenyl ethanol. For the production of propylene to be profitable, a use must be found for these by-products. The chemical route generally produces racemic 1,2-propanediol, whereas each of the two stereoisomers (R)1,2-propanediol and (S)1,2-propanediol are of interest for certain applications (e.g. chiral starting materials for specialty chemicals and pharmaceutical products).

The disadvantages of the chemical processes for the production of 1,2-propanediol make biological synthesis an attractive alternative. MGS (methylglyoxal synthase) is the mandatory first step from central metabolism for the production of this compound by fermentation. Processes for the production of 1,2-propanediol using different microorganisms, *Clostridium sphenoides* (DE3336051), *Klebsiella pneumoniae* (WO 2004/087936), recombinant yeast (WO 99/28481) or recombinant E. coli (WO 98/37204) have been disclosed. Alternative approaches for the production of 1,2-propanediol were also proposed by the applicant (WO 2005/073364, WO 2008/116852, WO 2008/116848).

During their investigations on 1,2-propanediol production, the inventors have identified new mutant GlyDHs that are less inhibited by the two products of the reaction, NAD+ and 1,2-propanediol and also less inhibited by the substrate hydroxyacetone than the wild type GlyDH, while keeping most of their specific activity for the conversion of hydroxyacetone into 1,2-propanediol. Use of GlyDH enzymes with such modified properties in a microorganism producing 1,2-propanediol is a key element in the design of more efficient processes for the production of 1,2-propanediol by fermentation and biomass conversion.

SUMMARY

The present invention concerns a method for the production of 1,2-propanediol, comprising culturing a microorganism modified for an improved production of 1,2-propanediol in an appropriate culture medium and recovery of the 1,2-propanediol which may be further purified wherein the microorganism expresses a glycerol dehydrogenase (GlyDH) enzyme with reduced inhibition of its activity by NAD+ and/or its substrate and/or its product.

The present invention concerns a mutant glycerol dehydrogenase (GlyDH) comprising at least one amino acid residue in the protein sequence of the parent enzyme replaced by a different amino acid residue at the same position wherein the mutant enzyme has retained more than 50% of the glycerol dehydrogenase activity of the parent enzyme and the glycerol dehydrogenase activity of the mutant GlyDH is less inhibited by NAD+ and/or by its substrate and/or by its product as compared to the parent enzyme.

The invention also concerns a DNA sequence comprising a sequence coding for the mutant GlyDH of the invention and a microorganism expressing such GlyDH, the inhibition of which activity by NAD+ and/or its substrate and/or its product is reduced, particularly a microorganism comprising a gene coding for the mutant GlyDH of the invention.

BRIEF DESCRIPTION OF THE DRAWINGS

FIGS. 1-3 depict embodiments of the present invention as described herein.

DETAILED DESCRIPTION OF A PREFERRED EMBODIMENT

In the present application, terms are employed with their usual meaning, except when precised otherwise.

Microorganisms

A "microorganism" means all kind of unicellular organisms, including procaryotic organisms like bacteria, and eucaryotic organisms like yeasts. Preferentially, the microorganism is selected among the group consisting of bacteria, yeasts and fungi, more preferentially selected among Enterobacteriaceae, Bacillaceae, Streptomycetaceae, Clostridiaceae and Corynebacteriaceae. More preferentially, the microorganism is a species of *Escherichia, Klebsiella, Pantoea, Salmonella, Bacillus, Streptomyces, Clostridium* or *Corynebacterium*. Even more preferentially, the microorganism is selected among the group consisting of *Escherichia coli, Klebsiella pneumoniae, Thermoanaerobacterium thermosaccharolyticum, Clostridium sphenoides* or *Saccharomyces cerevisiae*.

As used herein, the term "modified microorganism" or "modified" or "recombinant" refer to a host cell that has a modification of its genome, e.g., as by addition of nucleic acid not naturally occurring in the organism or by a modification of nucleic acid naturally occurring in the host cell.

A "microorganism modified for an improved production of 1,2-propanediol" is a microorganism in which pathways to favour the production of the desired biochemical by conversion of a simple source of carbon have been modified. The microorganism modified for such improved production produces more of the desired biochemical than a native, unmodified microorganism.

Figure 2:
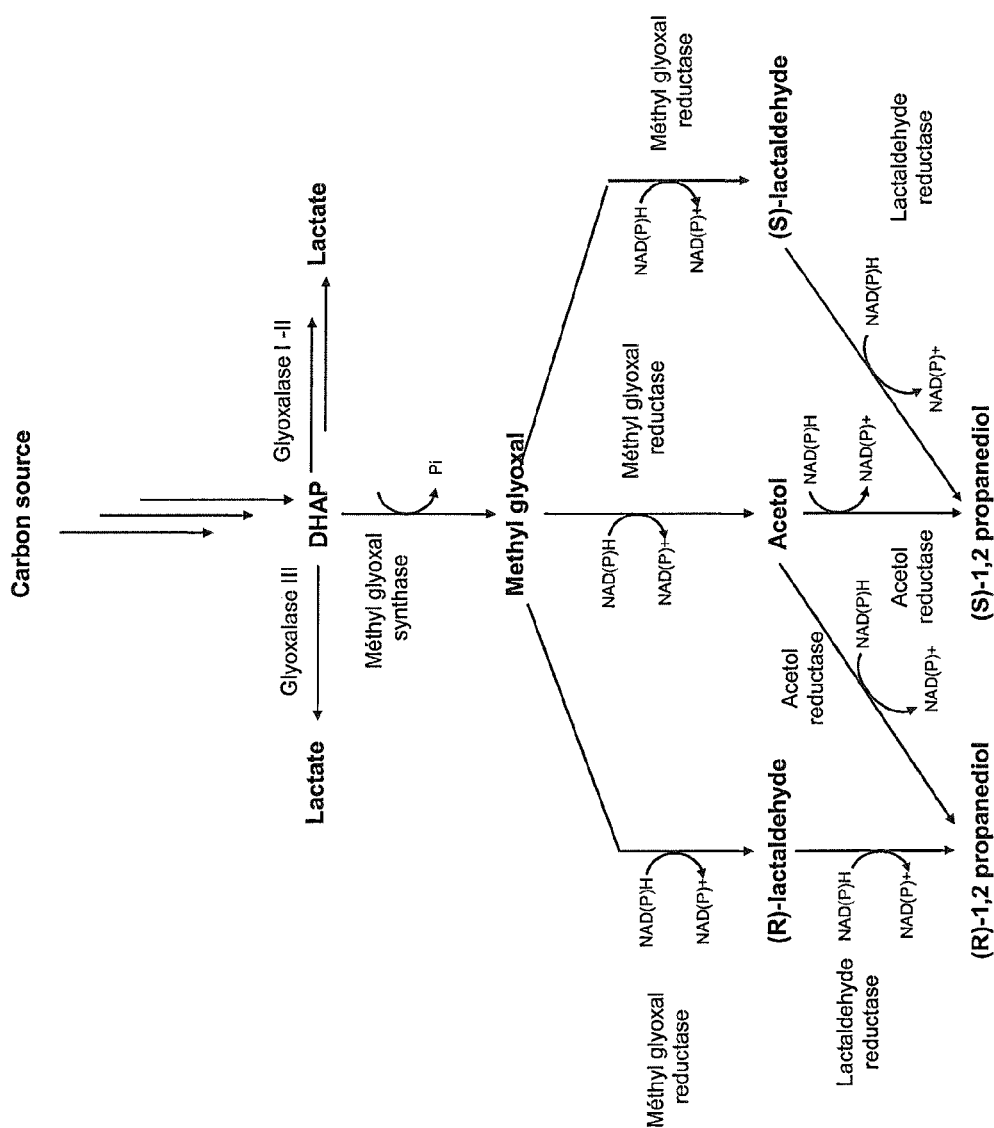

The preferred biosynthetic pathways for the production of 1,2-propanediol with the microorganism of the invention are represented on FIG. 2. The person skilled in the art shall identify the enzymatic activities related to the pathway to be promoted and the other enzymatic activities to be attenuated.

Microorganisms modified for the improved production of 1,2-propanediol by conversion of methyl glyoxal are also disclosed in Cameron et al, 1998, Bennett and San, 2001, Ko et al, 2005 and WO 99/28481, WO 98/37204, WO 2005/073364, WO 2008/116852, WO 2008/116848, PCT/EP2009/053093 which content is incorporated herein by reference.

In the case of yeasts, the following modifications of the host organism are preferred:
attenuation of expression of at least one of the following genes: TPI1, NDE1, NDE2, GUT2, GPD1, GPD2, PDC1, PDC2, PDC5, PDC6, GLO1
enhancement of expression of GRE3 gene.

In the microorganisms of the invention, the DNA sequence coding for a mutant GlyDH of the invention may be introduced in a vector for the expression and translation of the mutant GlyDH. It can also be integrated in the chromosome of the said microorganism.

Integration of the DNA sequence can be done either entirely, or simply by introducing in the native gene of the microorganism, the mutation in the coding sequence by replacing the nucleotide(s) coding for the amino acid to be changed by the nucleotide(s) coding for the amino acid of the mutated protein.

Total, partial or specific nucleotides replacement in a gene of a microorganism is well known in the art of genetic engineering, including Sambrook J et al., Molecular cloning: a laboratory manual, Cold Spring Harbour Press, New York (2001), Ausubel F M et al., Current protocols in molecular biology, John Wiley and sons, New York (1999), Adams A et al., Methods in yeast genetics, Cold Spring Harbour Press, New York (1997).

The microorganism of the invention may additionally comprise a gene coding for an YqhD enzyme which catalytic efficiency toward NADPH is increased.

An YqhD enzyme "which catalytic efficiency toward NADPH is increased" means that the catalytic efficiency towards NADPH of the YqhD enzyme expressed in the microorganism is higher than the catalytic efficiency towards NADPH of the native YqhD enzyme of the same microorganism. The catalytic efficiency is defined as the ratio between the catalytic constant (Kcat) and the Michaelis constant (Km). Increase of catalytic efficiency of YqhD enzyme means that the Kcat of the enzyme is increased or that the Km of the enzyme is decreased. In a preferred embodiment the Kcat of the YqhD enzyme is increased and the Km of the YqhD enzyme is decreased.

Preferably, the catalytic efficiency towards NADPH of the YqhD enzyme is higher than the efficiency of the native YqhD enzyme of *E. coli*.

Such enzyme has preferably an enzymatic activity of at least 50% of the activity of the YqhD of *E. coli*, more preferably at least 60% of the activity of the YqhD of *E. coli*.

Particularly, the YqhD enzyme is a mutant YqhDS enzyme wherein
the mutant enzyme has retained more than 50% of the YqhD activity of the parent enzyme and
the catalytic efficiency toward NADPH of the mutant YqhD is increased as compared with the catalytic efficiency toward NADPH of the parent enzyme.

Preferably the mutant YqhD comprises at least a mutation selected among the group consisting of G149E, G149S and A286T, and combinations thereof. The aminoacids positions are given by reference to the YqhD sequence of *E. coli*. The person skilled in the art shall find the corresponding aminoacids in sequences from other organisms by standard techniques of sequence alignment.

The microorganism of the invention may also comprise, additionally, a gene coding for a methylglyoxal synthase (MGS) enzyme which activity is not inhibited by orthophosphate.

"Not inhibited by orthophosphate" or "lacking inhibition by orthophosphate" means that no inhibition by orthophosphate is identified in an activity assay, when activity of the enzyme is studied in presence of orthophosphate.

In addition, kinetics of the MGS enzyme of the invention follows Michaelis-Menten kinetics regardless of the presence or absence of orthophosphate. Kinetics of the native enzyme follow a Michaelis-Menten model only in the absence of orthophosphate. The presence of orthophosphate makes the kinetic profile (specific activity over substrate concentration) of the native enzyme to become sigmoidal, which denotes the allosteric inhibition by orthophosphate.

Such enzyme has preferably a methylglyoxal synthase activity of at least 50% of the activity of the methylglyoxal synthase of *E. coli*.

Particularly, the MGS enzyme is a mutant MGS enzyme wherein
- the mutant enzyme has retained more than 50% of the activity of the parent enzyme and
- the methylglyoxal synthase activity of the mutant MGS is not inhibited by orthophosphate as compared to the parent enzyme.

Preferably the mutant MGS comprises at least a mutation selected among the group consisting of H21Q, A95V and V116L, and combinations thereof. The aminoacids positions are given by reference to the MgsA sequence of *E. coli*. The person skilled in the art shall find the corresponding aminoacids in sequences from other organisms by standard techniques of sequence alignment.

Glycerol Dehydrogenase (GlyDH) Enzyme

The invention concerns a glycerol dehydrogenase (GlyDH) the inhibition of which activity by NAD+ and/or its substrate and/or its product is reduced, a microorganism comprising the same and a method for the production of a desired biochemical by fermentation of said microorganism on a culture medium comprising a simple source of carbon.

"The inhibition of which activity by NAD+ and/or its substrate and/or its product is reduced" means that the inhibition of the activity of the GlyDH enzyme expressed in the microorganism is less inhibited than the activity of the native GlyDH enzyme of the same microorganism. The inhibition of the activity of the GlyDH enzyme can be defined by the Inhibition Concentration 50 (IC50) or the Inhibition Constant (Ki) or any other techniques known by the skilled person. The reduced inhibition of the activity of the GlyDH enzyme means that the IC50 or the Ki of the GlyDH enzyme of the invention is higher than the IC50 or the Ki of the native GlyDH enzyme. The skilled person knows the relation between IC50 and Ki and their meaning on the activity of enzyme among the classic Michaelis-Menten kinetics.

Preferably, the activity of the GlyDH enzyme is less inhibited than the native GlyDH enzyme of *E. coli*.

In a preferred embodiment, the enzyme activity is less inhibited for at least two members of the group consisting of NAD+, the enzyme's substrate and the enzyme's product. More preferably the enzyme activity is less inhibited by the three of NAD+, its substrate and its product.

The enzyme "substrate" is dihydroxyacetone, hydroxyacetone, methylglyoxal, lactaldehyde, glyceraldehyde, glycolaldehyde and derivatives thereof.

The enzyme "product" is the molecule obtained from the selected substrate by reduction of the carbonyl function.

For the production of 1,2-propanediol, the substrate is hydroxyacetone and the product is 1,2-propanediol.

Such enzyme has preferably a glycerol dehydrogenase activity of at least 50% of the activity of the glycerol dehydrogenase of *E. coli*.

Such an activity assay is well known in the art and can be carried out as disclosed in Example 2.

The enzymes may be obtained by various ways known to the person skilled in the art.

A first approach consists in screening native enzymes of various organisms for their reduced inhibition by NAD+ and/or their substrate and/or their product.

A second approach consists in inducing mutation(s) in enzymes of known organisms and selecting the enzymes for their lower of inhibition by NAD+ and/or the enzyme's substrate and/or the enzyme's product. Mutations may be induced by methods known in the art such as subjecting the microorganism to mutagenic agents. Another method to induce mutations is to growth the microorganism under selection pressure, with high levels of NAD+ and/or the enzyme's substrate and/or the enzyme's product and identify the microorganism growing under such conditions and select the enzymes obtained for their reduced inhibition by NAD+ and/or its substrate and/or its product.

Other methods are also known in the art to obtain mutations by shuffling DNA from various origins and select the proteins encoded by the shuffled DNA so obtained based on their glycerol dehydrogenase activity and their lower inhibition by NAD+ and/or the enzyme's substrate and/or the enzyme's product.

In a particular embodiment of the invention, the inventors obtained several mutants GlyDH retaining their glycerol dehydrogenase activity and having a lower inhibition by NAD+ and/or the enzyme's substrate and/or the enzyme's product by selecting strains modified for an improved production of 1,2-propanediol cultured under selection pressure as disclosed in WO 2005/073364 and as shown in Example 1.

The invention concerns particularly mutant glycerol dehydrogenase (GlyDH) comprising at least one amino acid residue in the protein sequence of the parent enzyme replaced by a different amino acid residue at the same position wherein
- the mutant enzyme has retained more than 50% of the activity of the parent enzyme and
- the glycerol dehydrogenase activity of the mutant GlyDH is less inhibited by NAD+ and/or by its substrate as compared to the parent enzyme and/or by its product as compared to the parent enzyme.

"Mutant" means that a mutation was introduced in a protein sequence by a person. According to the invention, a mutant enzyme is an enzyme comprising at least one amino acid difference with a parent enzyme. In the mutant enzyme of the invention, any change in amino acids may be introduced, either by directed mutagenesis or random mutagenesis, but also chimerical enzymes can be constructed, comprising parts of a second enzyme replacing corresponding parts of the parent enzyme.

The "parent enzyme" is the enzyme prior mutation. The parent enzyme may be of any origin, natural, isolated from another organism or synthetic. The method for determining that the mutated GlyDH has retained "more than 50%" is well known in the art and disclosed in Example 2.

Indeed, the skilled person shall choose the level of desired activity according to the final use of mutant GlyDH. Indeed, when a high activity is necessary, the skilled person will choose a mutant having more that 80% of activity, compared to the non mutated parent enzyme, more preferably more than 90% of activity. In other cases, selecting a mutant GlyDH with an activity around and above 50% compared to the parent enzyme may prevent additional modifications in a microorganism, like modifying the promoter to lower the level of expression of the enzyme.

According to the invention, "less inhibited by NAD+ and/or by its substrate and/or by its product as compared to the parent enzyme" means that:
- the value of the inhibition constant (Ki) for NAD+ of the native GlyDH enzyme is lower than the Ki of the mutant GlyDH, and/or
- the value of the inhibition constant (Ki) for its substrate of the native GlyDH enzyme is lower than the Ki of the mutant GlyDH, and/or
- the residual specific activity of the native GlyDH enzyme in the presence of 100 mM 1,2-propanediol (product) is lower than the residual specific activity of the mutant GlyDH.

According to the invention, "reduced inhibition of its activity by NAD+ and/or its substrate and/or its product" means that:

the value of the inhibition constant (Ki) for NAD+ is preferably higher than 0.85 mM, more preferably higher than 6.5 mM, and/or the value of the inhibition constant (Ki) for the substrate (e.g. hydroxyacetone) is preferably higher than 40 mM, more preferably higher than 100 mM, and/or the residual specific activity of the enzyme in the presence of 100 mM 1,2-propanediol (product) is preferably higher than 50% of the specific activity of native GlyDH enzyme of *E. coli*, more preferably higher than 65%.

Methods used to calculate the kinetic parameters of the enzymes are given in Examples 2 and 3 but can also be found e.g. in Segel, I H, Enzyme Kinetics, John Wiley & Sons (1993).

In a preferred embodiment, the mutant GlyDH of the invention comprises at least one amino acid residue of an identified region in the native parent GlyDH replaced by a different amino acid residue at the same position.

The inventors have identified mutants GlyDH comprising at least one amino acid residue of one of the following Conserved Regions in the native parent GlyDH which has been replaced by a different amino acid residue at the same position:

-Pro-Thr-Xa1-Xa2-Xa3-Xa4-Xa5-Xa6-Xa7-Xa8-Xa9- (CR1)

wherein
Xa1 represents Ala, Ile, Ser, Thr and Val,
Xa2 represents Ala and Pro, preferably Ala,
Xa3 represents Ala and Ser, preferably Ala,
Xa4 represents Asn, His and Thr, preferably His,
Xa5 represents Asp and Cys, preferably Asp,
Xa6 represents Ala and Gly, preferably Gly,
Xa7 represents Ala, Gly, Ile and Pro, preferably Ile,
Xa8 represents Ala, Cys, Thr, Trp and Val, preferably Ala, and
Xa9 represents Ser and Thr, preferably Ser,
and -X10-X11-X12-X13-X14-X15-X16-X17-X18-X19-X20-Gly- X21-X22-Asp- (CR2)

wherein
X10 represents Ile, Leu, Met and Val, preferably Ile,
X11 represents Ala, Arg, Gln, Ile, Leu, Lys, Ser and Val, preferably Ala,
X12 represents Ala, Asn, Asp, Arg, Glu, Gly, Leu, Lys, Ser and Thr,
X13 represents Ala and Serl, preferably Ala,
X14 represents Glu and Pro, preferably Pro,
X15 represents Ala, Arg, Gln, Glu, Lys, Phe, Pro, Ser, Trp, Tyr and Val,
X16 represents Arg, Gln, and Glu, preferably Arg,
X17 represents Leu, Phe and Tyr, preferably Leu,
X18 represents Asn, Ile, Leu, Thr and Val, preferably Leu,
X19 represents Ala, Arg, Asn, Ile, Leu, Lys, Ser, Thr and Val, preferably Ala,
X20 represents Ala and Ser, preferably Ala,
X21 represents Ala, Cys, Ile, Phe, Met and Val, preferably Ile, and
X22 represents Ala and Gly, preferably Gly.

These conserved regions can be identified in different GlyDH enzymes by simple sequence alignment using standard sequence alignment tools such as ClustalW2, Kalign, MAFFT, MUSCLE or T-coffee, all available on the website http://www.ebi.ac.uk/. A sequence alignment of several GlyDH of different species is given in FIG. 1A-C.

Amino acids numbers in the present application are given by reference to the proteins of *E. coli*.

It can be found in FIG. 1A-C that CR1 correspond to amino acids 115 to 125 of *E. coli* GlyDH and CR2 correspond to amino acids 157 to 171 of *E. coli* GlyDH.

According to the invention, the mutant GlyDH can have at least one mutation in one of CR1 or CR2, and at can have at least two mutations in CR1 and CR2.

"At least" in such context means that the mutated enzyme may have other mutations, but nor related to the identified Conserved Regions CR1, CR2 and CR3. These other non identified mutations have no substantial impact on the mutated enzyme of the invention, provided that:

the mutant enzyme has retained more than 50% of the glycerol dehydrogenase activity of the parent enzyme and the glycerol dehydrogenase activity of the mutant GlyDH is less inhibited by NAD+ and/or by its substrate and/or by its product as compared to the parent enzyme.

In preferred embodiments, the amino acid residue in the conserved regions CR1 and CR2 in the native parent GlyDH replaced by a different amino acid residue at the same position in the mutant GlyDH is selected among the group consisting of amino acid Xa4 in CR1 and amino acid X13 in CR2 and combinations thereof.

Xa4 correspond to amino acid 120 in the GlyDH sequence of *E. coli*. X13 corresponds to amino acid 160 in the GlyDH sequence of *E. coli*.

Particularly, the mutated GlyDH of the invention comprises at least one of the mutations selected among the group consisting in T120N, A160T and combinations thereof, the amino acid positions being given by reference to the GldA sequence of *E. coli*.

More preferably, the mutated GlyDH of the invention comprises at least one of the following amino acid sequences in conserved regions CR1 and CR2
CR1: Pro Thr Ile Ala Ser Asn Asp Ala Pro Cys Ser
CR2: Val Ala Gly Thr Pro Ala Arg Leu Leu Ala Ala Gly Ile Gly Asp the amino acid residue marked in bold and underlined corresponding to the amino acid in the mutant GlyDH different from the amino acid in the parent GlyDH.

Particularly, the mutant GlyDH of the invention has at least 25% sequence identity compared to the GlyDH sequence of *E. coli*, provided that it comprises at least one of the following mutations in CR1 and/or CR2:
CR1: Pro Thr Ile Ala Ser Asn Asp Ala Pro Cys Ser
CR2: Val Ala Gly Thr Pro Ala Arg Leu Leu Ala Ala Gly Ile Gly Asp Sequence identity is defined after sequence alignment of the GlyDH sequence of *E. coli* with the protein sequence to be compared using CLUSTALW2 available on the EBI website (see above) with default parameters. The sequence identity is then calculated with the sequence alignment by the ratio of the number of identical amino acids at the same position with the total number of amino acids in the reference sequence (*E. coli*).

Preferably, the mutant GlyDH has at least 40% sequence identity.

In most preferred embodiments, the mutant GlyDH of the invention comprises the sequence selected among the group consisting of GlyDH identified in SEQ ID NO 1 and SEQ ID NO 2.

DNA, Vectors, Genes

The present invention also concerns a DNA sequence comprising a sequence coding for the mutant GlyDH of the invention. The sequence coding for the mutant GlyDH of the invention is not a limiting factor by itself. The skilled person can easily obtain the sequence of a native GlyDH from a microorganism and introduce in the coding sequence the mutation(s) to be introduced in the protein by changing one or more appropriate nucleotide.

The skilled person can also perform a mutagenesis in the sequence of a microorganism, and isolate the mutated DNA sequence by standard methods.

Mutations can be introduced by site-directed mutagenesis by usual methods like Polymerase Chain Reaction (PCR, see Sambrook J et al., Molecular cloning: a laboratory manual, Cold Spring Harbour Press, New York (2001), Ausubel F M et al., Current protocols in molecular biology, John Wiley and sons, New York (1999), Adams A et al., Methods in yeast genetics, Cold Spring Harbour Press, New York (1997)), or by random mutagenesis techniques, such as use of mutagenic agents (Ultra-Violet rays or chemical agents like nitrosoguanidine (NTG) or ethylmethanesulfonate (EMS)) or use of PCR techniques (DNA shuffling or error-prone PCR).

The person skilled in the art can also prepare synthetic genes with preferred codons selected for an improved expression in a specific organism. Codons usages by various organisms are well known in the art and several companies are proposing the manufacture of synthetic genes with codon optimization.

The sequence of the invention can be isolated, consisting in the coding sequence as defined above, or within a gene comprising regulatory elements upstream and downstream the coding sequence for its expression in a specific organism.

The sequence can also be present in a vector, for its replication (replication vector) or for the expression and translation of the mutated protein of the invention in a microorganism (expression vector). Such vectors are known in the art and not a limiting factor for the definition of the invention.

Said genes and vectors are also part of the invention.

Preferably, the DNA sequence of the invention is in a microorganism with regulatory elements allowing expression and translation of the mutated GlyDH of the invention.

Production of 1,2-propanediol

The invention also concerns a method for the production of 1,2-propanediol by fermentation comprising culturing a microorganism of the invention, modified for an improved production of 1,2-propanediol and recovery of the 1,2-propanediol.

In a particular embodiment, the recovered 1,2-propanediol is purified.

Methods for the purification of 1,2-propanediol are known in the art and described in U.S. Pat. No. 5,076,896 and WO 2007/074066, incorporated herein by reference.

Advantageously, the production is done by fermentation in a batch, fed-batch or continuous process, according to processes known to the person skilled in the art of microorganisms fermentation.

Culture Medium and Carbon Source

In the production method of the invention, the microorganism is cultured on an appropriate culture medium.

An "appropriate culture medium" means a medium of known molecular composition adapted to the growth of the micro-organism. In particular, said medium contains at least a source of phosphorus and a source of nitrogen. Said appropriate medium is for example a mineral culture medium of known set composition adapted to the bacteria used, containing at least one carbon source. Said appropriate medium may also designate any liquid comprising a source of nitrogen and/or a source of phosphorus, said liquid being added and/or mixed to the source of sucrose. In particular, the mineral growth medium for Enterobacteriaceae can thus be of identical or similar composition to M9 medium (Anderson, 1946), M63 medium (Miller, 1992) or a medium such as defined by Schaefer et al. (1999).

The carbon source 'glucose' can be replaced in this medium by any other carbon source, in particular by sucrose or any sucrose-containing carbon source such as sugarcane juice or sugar beet juice.

A "carbon source" or "carbon substrate" means any carbon source capable of being metabolized by a microorganism wherein the substrate contains at least one carbon atom.

Preferably, the carbon source is selected among the group consisting of glucose, sucrose, mono- or oligosaccharides, starch or its derivatives or glycerol and mixtures thereof.

Indeed the microorganisms used in the method of the present invention can be modified to be able to grow on specific carbon sources when the non modified microorganism cannot grow on the same source of carbon, or grow at to low rates. These modifications may be necessary when the source of carbon is a byproduct of biomass degradation such as by-products of sugarcane including; filter cake from clarification of raw juice and different kind of molasses.

FIG. 1A-C represents the alignment of 23 protein sequences of GlyDH or homologous enzymes of various sources. The sequences EGSA PICTO (SEQ ID NO: 47); EGSA THEVO (SEQ ID NO: 48); EGSA THEAC (SEQ ID NO: 49); EGSA PYRAE (SEQ ID NO: 50); EGSA METJA (SEQ ID NO: 51); EGSA AERPE (SEQ ID NO: 52); EGSA HALSA (SEQ ID NO: 53); EGSA SULSO (SEQ ID NO: 54); EGSA SULAC (SEQ ID NO: 55); EGSA SULTO (SEQ ID NO: 56); EGSA METMA (SEQ ID NO: 57); EGSA METAC (SEQ ID NO: 58); EGSA METKA (SEQ ID NO: 59); EGSA PYRKO (SEQ ID NO: 60); EGSA PYRFU (SEQ ID NO: 61); EGSA PYRHO (SEQ ID NO: 62); EGSA PYRAB (SEQ ID NO: 63); GLDA BACST (SEQ ID NO: 64); GLDA CITFR (SEQ ID NO: 65); GLDA ECOL6 (SEQ ID NO: 66); GLDA PSEPU (SEQ ID NO: 67); YBDH ECOLI (SEQ ID NO: 68); and Y1167 SYNY3 (SEQ ID NO: 69) were obtained from the UniProt Knowledge Base (The UniProt consortium (2008)) and the alignment made using MUSCLE with default parameters.

FIG. 2 represents the metabolic pathways for the production of lactic acid, acetol and 1,2-propanediol in the microorganisms of the invention.

Figure 3:
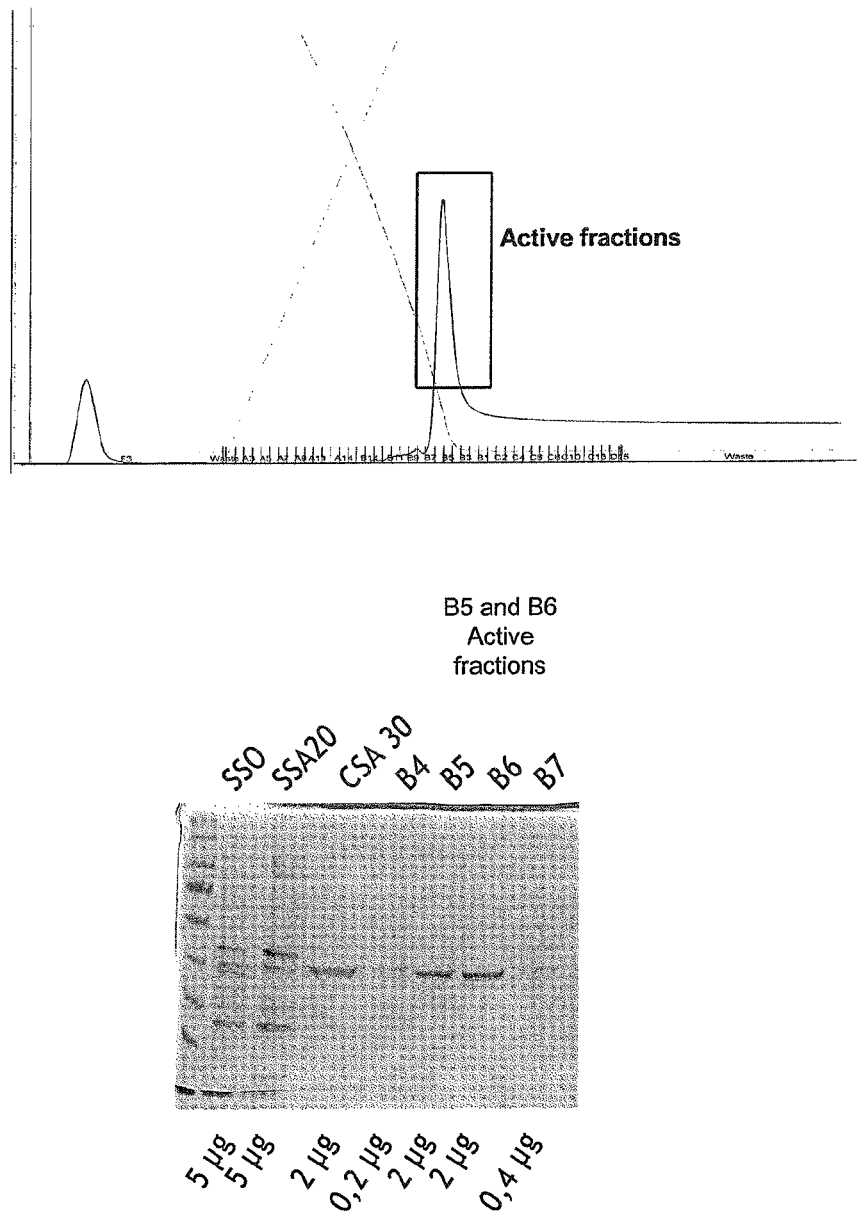

FIG. 3 represents a chromatographic profile and purity control on sodium dodecylsulfate polyacrylamide gel electrophoresis: glycerol dehydrogenase was collected in two fractions. Legend: SSO: sonication supernatant; SSA: 20% ammonium sulphate supernatant; CSA: 30% ammonium sulphate resuspended precipitate.

EXAMPLES

Example 1

**Evolution of 2 Modified Strains of *E. coli* MG1655 in Chemostat Culture and Identification of 2 Mutant GlyDH Enzymes in the Evolved Clones**

The construction of the strains *E. coli* MG1655 lpd* ΔtpiA, ΔpflAB, ΔadhE, ΔldhA::Cm, ΔgloA, ΔaldA, ΔaldB, Δedd (strain 1) and *E. coli* MG1655 lpd* ΔtpiA, ΔpflAB, ΔadhE, ΔldhA, ΔgloA, ΔaldA, ΔaldB, Δedd, ΔarcA, Δndh::Km (strain 2) were previously described in patent application WO 2008/116852.

To evolve them toward improved 1,2 propanediol production, the 2 strains were cultivated in continuous culture, either under anaerobic conditions, or under microaerobic conditions (1% oxygen) in the culture medium MPG (given in patent application WO 2008/116852) with 0.42 or 0.84 g/l sodium nitrate, with excess glucose (from 20 g/l initially with addition if the glucose becomes exhausted). The temperature was set at 37° C., the pH was regulated at 6.5 by addition of base and the dilution rate of the chemostat was set between 0.04 h$^{-1}$ and 0.08 h$^{-1}$. The evolution of the strain in the chemostats was followed by the increase of the biomass concentration coupled with the increase of the concentrations of the product, 1,2-propanediol and the co-product acetate, over several weeks. This denoted the improvement of the performances of the strains. When the cultures reached a steady state with no further increase of the concentrations under these conditions, the evolution was done.

The characteristics of the strains before and after evolution were assessed. Single colonies representing individual clones were isolated on Petri dishes. These clones were assessed using the initial strain as control in an Erlenmeyer flask assay, using the same medium MPG used in the chemostat culture, but buffered with MOPS. Among these clones, several presented better 1,2-propanediol specific production rates as compared to the control. The results obtained on the best clone for each condition of evolution are reported in Table 1 and 2 below.

TABLE 1

Comparison of the best evolved clone obtained after 66 days of evolution under anaerobic conditions with the initial strain

| Strain *E. coli* MG1655 lpd* ΔtpiA ΔpflAB ΔadhE ΔldhA::Cm ΔgloA Δald, ΔaldB Δedd (Strain 1) | Initial strain before evolution (performances measured after 2 days of culture) | Best evolved clone (performances measured after 2 days of culture) |
|---|---|---|
| Glucose specific consumption rate (g glucose/g biomass/h) | 0.12 | 0.21 (+75%) |
| 1,2-propanediol specific production rate (g 1,2-propanediol/g biomass/h) | 0.02 | 0.07 (+250%) |
| 1,2-propanediol + hydroxyacetone specific production rate (g 1,2-propanediol + hydroxyacetone/g biomass/h) | 0.04 | 0.08 (+100%) |

TABLE 2

Comparison of the best evolved clone obtained after 132 days of evolution under microaerobic conditions with the initial strain

| Strain *E. coli* MG1655 lpd* ΔtpiA ΔpflAB ΔadhE ΔldhA::Cm ΔgloA Δald, ΔaldB, Δedd, ΔarcA Δndh (Strain 2) | Initial strain before evolution (performances measured after 2 days of culture) | Best evolved clone (performances measured after 2 days of culture) |
|---|---|---|
| Glucose specific consumption rate (g glucose/g biomass/h) | 0.15 | 0.28 (+87%) |
| 1,2-propanediol specific production rate (g 1,2-propanediol/g biomass/h) | 0.00 | 0.10 |
| 1,2-propanediol + hydroxyacetone specific production rate (g 1,2-propanediol + hydroxyacetone/g biomass/h) | 0.04 | 0.10 (+150%) |

Specific genes involved in the terminal 1,2-propanediol biosynthetic pathway were sequenced in the 2 best evolved clones of strain 1 and strain 2. For each clone, one mutated gldA gene was identified resulting in expression of mutated GlyDH protein: GldA*(A160T) for evolved clone of strain 1 and GldA*(T120N) for evolved clone of strain 2.

Example 2

Production, Purification and Characterization of Native GlyDH and 2 Mutant GDH (A160T & T120N) on 3 Substrates (Methylglyoxal, Hydroxyacetone & Glycolaldehyde)

1. Construction of the Strains for Production of GlyDH Proteins 1.1. Construction of the Plasmid for the Overexpression of gldA:pETTOPO-gldA The plasmid was built to obtain the overexpression of the native protein (without His-tag). The gene gldA (sequence 4135955-4137058) encoding for the GlyDH enzyme was PCR amplified from genomic DNA of *E. coli* MG1655 using the following oligonucleotides:

pETTOPO gldA F (consisting of 24 pb): cacc atggaccgcattattcaatc(SEQIDNO3), with
  a region (underlined letters) homologous to the sequence (4137058-4137039) of the gene gldA.
  a region (bold) for directional cloning of the fragment in the plasmid pET101. and pETTOPO-N gldA R (consisting of 25 pb) ttattcccactcttgcaggaaacgc(SEQIDNO4)

with a region (underlined letters) homologous to the sequence (4135955-4135979) of the gene gldA.

The fragment amplified was directly cloned into the pET101 from the "Champion pET Directional TOPO Expression Kits" (Invitrogen®). The plasmid built was named pET-TOPO-gldA.

1.2. Construction of the Plasmids for the Overexpression of gldA*

The two mutants GlyDH bear the mutations A160T or T120N. The plasmids for the overexpression of the two mutant proteins were built by site-directed mutagenesis using Quickchange site-directed mutagenesis kit from Stratagene® on pETTOPO-gldA with oligonucleotides described in table 3.

TABLE 3

Oligonucleotides used for the directed mutagenesis of gldA

| mutant | Names of oligos | Sequence of the oligonucleotide | Modification to create mutation | Homologous to the sequence |
|---|---|---|---|---|
| A160T | gldA*A160Tm utDirF | gacaccaaaatcgtcgctggcAcacct gcacgtctgCtagcggcg (SEQ ID NO 5) | Red capital letter: A instead of G to create A 160T mutation Green capital letter: C instead of T to create NheI restriction site without change in protein sequence | 4136602 to 4136558 |
| | gldA*A160Tm utDirR | cgccgctaGcagacgtgcaggtgTgc cagcgacgattttggtgtc (SEQ ID NO 6) | Red capital letter: T instead of C to create A 160T mutation Green capital letter: G instead of A to create NheI restriction site without change in protein sequence | |
| T120N | gldA*(T120N) MD F | gcgatcgcaccgactatcgcctctaAc gatgcaccCtgcagcgcattg (SEQ ID NO 7) | Red capital letter: A instead of C to create T120N mutation Green capital letter: C instead of G to create PstI restriction site without change in protein sequence | 4136725 to 4136678 |
| | gldA*(T120N) MD R | caatgcgctgcaGggtgcatcgTtaga ggcgatagtcggtgcgatcgc (SEQ ID NO 8) | Red capital letter: T instead of G to create T120N mutation Green capital letter: G instead of C to create PstI restriction site without change in protein sequence | |

The two plasmids obtained were named pETTOPO-gldA* (A160T) and pETTOPO-gldA*(T120N).

1.3. Construction of BL21 Star (DE3) ΔgldA::Cm

To avoid the mix between the mutant proteins expressed by plasmid and the wild-type one expressed by chromosome, the strain used to do the overexpression was deleted of the gldA gene.

1.3.1. Construction of the Strain MG1655 ΔgldA::Cm

The gene gldA, coding for GlyDH enzyme, was inactivated in strain *E. coli* MG1655 by inserting a Chloramphenicol resistance cassette and deleting most of the gene concerned using the technique described in Protocol 1.

Protocol 1: Introduction of a PCR product for recombination and selection of the recombinants (FRT system).

The oligonucleotides chosen and given in Table 4 for replacement of a gene or an intergenic region were used to amplify either the chloramphenicol resistance cassette from the plasmid pKD3 or the kanamycin resistance cassette from the plasmid pKD4 (Datsenko, K. A. & Wanner, B. L. (2000)). The PCR product obtained was then introduced by electroporation into the recipient strain bearing the plasmid pKD46 in which the system λ Red (γ, β, exo) expressed greatly favours homologous recombination. The antibiotic-resistant transformants were then selected and the insertion of the resistance cassette was checked by PCR analysis with the appropriate oligonucleotides given in Table 5.

If they are other modifications in the strain, they were checked with the oligonucleotides given in Table 5.

The resulting strain was named *E. coli* MG1655 ΔgldA:: Cm.

TABLE 4

Oligonucleotides used for replacement of a chromosomal region by recombination with a PCR product

| Region name | Names of oligos | Homology with chromosomal region |
|---|---|---|
| gldA | DgldA F | 4137058 to 4136979 |
| | DgldA R | 4135955 to 4136034 |

TABLE 4-continued

Oligonucleotides used for replacement of a chromosomal region by recombination with a PCR product

| Region name | Names of oligos | Homology with chromosomal region |
|---|---|---|
| edd-eda | DedaR | 1930144 to 1930223 |
| | DeddF | 1932501 to 1932582 |
| aldA | DaldAR | 1487615 to 1487695 |
| | DaldAF | 1486256 to 1486336 |
| aldB | DaldBR | 3754534 to 3754455 |
| | DaldBF | 3752996 to 3753075 |
| arcA | DarcAF | 4637868 to 4637791 |
| | DarcAR | 4637167 to 4637245 |
| Ndh | DndhF | 1165071 to 1165149 |
| | DndhR | 1166607 to 1166528 |
| Ptrc01-gapA | Ptrc-gapAF | 1860800-1860762 |
| | Ptrc-gapAR | 1860478-1860536 |
| gloA | DgloA F | 1725861 to 1725940 |
| | DgloA R | 1726268 to 1726189 |

TABLE 5

Oligonucleotides used for checking the insertion of resistance cassette or the loss of resistance cassette

| Region name | Names of oligos | Homology with chromosomal region |
|---|---|---|
| gldA gene | talC F | 4137144 to 4137121 |
| | yijF R | 4135136 to 4135159 |
| edd-eda genes | edaR | 1929754 to 1929777 |
| | eddF | 1932996 to 1932968 |
| aldA gene | aldAF | 1485877 to 1485901 |
| | aldAR | 1487714 to 1487689 |
| aldB gene | aldBF | 3752056 to 3752095 |
| | aldBR | 3754644 to 3754674 |
| arcA gene | arcAF | 4638292 to 4638273 |
| | arcAR | 4636854 to 4636874 |
| ndh gene | ndhF | 1164722 to 164742 |
| | ndhR | 1167197 to 1167177 |
| Ptrc01-gapA | yeaAF | 1860259 to 1860287 |
| | gapAR | 1861068 to 1861040 |

TABLE 5-continued

Oligonucleotides used for checking the insertion of resistance cassette or the loss of resistance cassette

| Region name | Names of oligos | Homology with chromosomal region |
|---|---|---|
| gloA gene | gloAF2 | 1725641 to 1725660 |
|  | gloAR2 | 1726450 to 1726431 |
| mgsA::Km | helDF | 1025242 to 1025260 |
|  | mgsA R3 | 1026734 to 1026715 |

1.3.2. Construction of the Strain BL21 Star (DE3) ΔgldA::Cm

The deletion of the gene gldA by replacement of the gene by a chloramphenicol resistance cassette in the strain E. coli BL21 star (DE3) was performed by the technique of transduction with phage P1 (Protocol 2).

Protocol 2: Transduction with phage P1 for deletion of a gene

The deletion of the chosen gene by replacement of the gene by a resistance cassette (kanamycin or chloramphenicol) in the recipient E. coli strain was performed by the technique of transduction with phage P1. The protocol was in two steps, (i) the preparation of the phage lysate on the strain MG1655 with a single gene deleted and (ii) the transduction of the recipient strain by this phage lysate.

Preparation of the Phage Lysate

Seeding with 100 µl of an overnight culture of the strain MG1655 with a single gene deleted of 10 ml of LB+Cm 30 µg/ml+glucose 0.2%+CaCl$_2$ 5 mM.

Incubation for 30 min at 37° C. with shaking.

Addition of 100 µl of phage lysate P1 prepared on the wild type strain MG1655 (approx. 1×10$^9$ phage/ml).

Shaking at 37° C. for 3 hours until all cells were lysed.

Addition of 200 µl of chloroform, and vortexing.

Centrifugation for 10 min at 4500 g to eliminate cell debris.

Transfer of supernatant in a sterile tube and addition of 200 µl of chloroform.

Storage of the lysate at 4° C.

Transduction

Centrifugation for 10 min at 1500 g of 5 ml of an overnight culture of the E. coli recipient strain in LB medium.

Suspension of the cell pellet in 2.5 ml of MgSO$_4$ 10 mM, CaCl$_2$ 5 mM.

Control tubes: 100 µl cells

100 µl phages P1 of the strain MG1655 with a single gene deleted.

Tube test: 100 µl of cells+100 µl phages P1 of strain MG1655 with a single gene deleted.

Incubation for 30 min at 30° C. without shaking.

Addition of 100 µl sodium citrate 1 M in each tube, and vortexing.

Addition of 1 ml of LB.

Incubation for 1 hour at 37° C. with shaking

Plating on dishes LB+Cm 30 µg/ml after centrifugation of tubes for 3 min at 7000 rpm.

Incubation at 37° C. overnight.

The antibiotic-resistant transformants were then selected and the insertion of the deletion was checked by a PCR analysis with the appropriate oligonucleotides given in Table 5.

The strain obtained was named E. coli BL21 star (DE3) ΔgldA::Cm.

1.4. Introduction of Plasmids in the Strain E. coli BL21 Star (DE3) ΔgldA::Cm

The plasmids pETTOPO-gldA, pETTOPO-gldA* (A160T), pETTOPO-gldA*(T120N) were introduced by electroporation in the strain E. coli BL21 star (DE3) ΔgldA::Cm and the following strains were obtained:

BL21 star (DE3) ΔgldA::Cm pETTOPO-gldA

BL21 star (DE3) ΔgldA::Cm pETTOPO-gldA*(A160T)

BL21 star (DE3) ΔgldA::Cm pETTOPO-gldA*(T120N)

2. Production of GlyDH Proteins

The three strains BL21 star (DE3) ΔgldA::Cm pETTOPO-gldA, BL21 star (DE3) ΔgldA::Cm pETTOPO-gldA*(A160T) and BL21 star (DE3) ΔgldA::Cm pETTOPO-gldA*(T120N) were cultivated at 37° C. under aerobic conditions in 2 l baffled Erlenmeyer flasks with 500 ml LB medium with 2.5 g/l glucose. The flasks were agitated at 200 rpm on an orbital shaker. When the optical density measured at 550 nm reached 0.5 units, the flasks were incubated at 25° C. When the optical density reached 1.2 units, the production of GlyDH proteins was induced by adding 500 µM IPTG in the cultures. The biomass was harvested by centrifugation when the cultures reached an optical density above 3.5 units. The supernatant was discarded and the pellet was stored at −20° C. before use.

3. Activity Assay for GlyDH

Glycerol dehydrogenase activity of the native and evolved proteins was assayed by measuring the initial rate of NADH oxidation of with a spectrophotometer (Hewlett Packard, 8453) at a wavelength of 340 nm and a constant temperature of 30° C. The oxidation reaction was carried out in quartz cuvette cells filled with 1 ml of the mixture: 100 mM MES buffer pH 6.5 with 30 mM of ammonium sulphate, 0.1 mM of iron sulphate, 0.1 mM of NADH and around 0.5 µg of purified proteins. Assays were initiated by the addition of one of these substrates: hydroxyacetone, glycolaldehyde or methyl glyoxal. In all reactions, non enzymatic rates were subtracted from the observed initial reaction rates. Enzyme activities are reported as µmoles of substrate/min/mg of cell protein and represents averages for at least three purified enzyme preparations.

4. Purification of the GlyDH Enzymes

The purification process designed to purify the glycerol dehydrogenase overexpressed in E. coli is composed of two steps. At each step, glycerol dehydrogenase activity was evaluated using 0.4 mM hydroxyacetone as a substrate as described in 1.2 to determine yield and purification factor. Cell pellets were resuspended in 3 ml of 50 mM HEPES buffer pH 7.5 containing protease inhibitor cocktail (Roche) and homogenized by sonication (at 0° C., under aerobic conditions, in four cycles of 30 s with 2 minutes intervals between each cycle). Cells debris were eliminated by centrifugation (5 min 12000 g) and nucleic acids in cell homogenate were precipitated by a streptomycin sulphate treatment (13.3 mg/ml final concentration, 15 minutes, 0° C.). The streptomycin sulphate treated cell homogenate was harvested by centrifugation (5 min 12000 g), and contaminant proteins of the supernatant were eliminated by ammonium sulphate precipitation at a saturated concentration of 20%, at 4° C., with stirring over one hour. The precipitate was then removed by centrifugation (20 min, 8600 g, 4° C.) and discarded. A further portion of ammonium sulphate at a saturated concentration of 30% was added to the supernatant as previously and then centrifuged 30 minutes at 8600 g 4° C. collecting the precipitate. The precipitate was dissolved in 3 ml of 50 mM Hepes Buffer pH 7.5 with 1M ammonium sulphate before loading 2.5 ml sample onto a hydrophobic interaction chromatography column (Hitrap phenyl sepharose, GEhealthcare) connected to an AKTA purifier system and equilibrated with 50 mM Hepes Buffer pH 7.5 containing 1M ammonium sulphate. After washing with 20 ml of the same buffer, proteins were eluted with a 20 ml linear gradient of 50 mM Hepes Buffer pH 7.5 from 1 M to 0 M of ammonium sulphate. Active glycerol dehydrogenase proteins were eluted in two fractions which were pooled before specific activities and kinetics parameters determination or storage at −80° C. The protein concentration and purity were respectively determined with the Bradford reagent and with sodium dodecylsulfate polyacrylamide gel electrophoresis (FIG. 3).

The SDS-Page analysis revealed the presence of a single band for the purified fractions B5 and B6 stained with Coomassie Blue corresponding to the molecular mass of GldA (39 KDa).

5. Characterization of the GlyDH Enzymes

The native GlyDH and both evolved enzymes were purified as described previously and their NADH oxidation activities were measured with three substrates: hydroxyacetone, glycoaldehyde and methyl glyoxal (Table 6). For the native purified enzyme, the highest specific activity was obtained for glycolaldehyde followed by methyl glyoxal and hydroxyacetone. Similar results were observed on both evolved enzymes.

TABLE 6

Comparison of specific activity of the three enzymes on three different substrates

| Enzymes | Specific activity (U/mg) | | |
|---|---|---|---|
| | Hydroxyacetone | Methyl glyoxal | Glycolaldehyde |
| GlyDH | 36.3 +/− 0.88 | 57.77 +/− 3.81 | 148.89 +/− 19.36 |
| GlyDH*(A160T) | 40.5 +/− 0.85 | 58.27 +/− 2.42 | 167.33 +/− 6.03 |
| GlyDH*(T120N) | 80.41 +/− 1.63 | 61.01 +/− 4.00 | 212.17 +/− 21.04 |

Moreover, a higher specific activity of both evolved enzymes compared to the native enzyme was detected on the three substrates. The most active enzyme was the GlyDH* (T120N).

The Km and kcat values were determined by measuring initial velocities over a range of substrate concentrations of hydroxyacetone (0.1 to 15 mM), glycolaldehyde (1 to 40 mM) methyl glyoxal (1 to 20 mM). The kinetic parameters were determined with Sigma Plot (Systat Software Inc, San Jose Calif.) by fitting to the Michaelis Menten equation using a non linear regression.

The kinetics parameters for the three substrates of the three enzymes were determined as shown in Table 7.

TABLE 7

Comparison of the kinetics parameters of GlyDH, GlyDH*(A160T) and GlyDH*(T120N)

| | Substrates | | | | | |
|---|---|---|---|---|---|---|
| | Hydroxyacetone | | Methyl glyoxal | | Glycoaldehyde | |
| | Km (mM) | Kcat/Km $mM^{-1}/s^{-1}$ | Km (mM) | Kcat/Km $mM^{-1}/s^{-1}$ | Km (mM) | Kcat/Km $mM^{-1}/s^{-1}$ |
| GlyDH | 0.07 +/− 0.02 | 378 | 2.49 +/− 0.58 | 15 | 1.69 +/0.79 | 57 |
| GlyDH *(A160T) | 0.15 +/− 0.02 | 189 | 3.77 +/0.46 | 9.9 | 5.53 +/0.65 | 19 |
| GlyDH *(T120N) | 0.43 +/− 0.04 | 121 | 6.54 +/− 1.19 | 6.0 | 23.5 +/− 4.11 | 6 |

For the GlyDH native enzyme, the Km for glycolaldehyde and methyl glyoxal were respectively 1.7 mM and 2.5 mM relative to 0.07 for hydroxyacetone with a Kcat/Km for hydroxyacetone 20 fold higher for hydroxyacetone than that of methyl glyoxal and 7 fold higher for hydroxyacetone than that of glycolaldehyde. These kinetics parameters are in the same range than the one previously published (Subedi K P et al. 2007, FEMS Microb.Lett.: 279, 180-187). In addition, no significant differences of the kinetics between both evolved enzymes GlyDH A160T, GlyDH T120N and native enzyme were observed. These results on the three GlyDH enzymes for their affinity and specificity towards three substrates hydroxyacetone, methyl glyoxal and glycolaldehyde at physiologic pH (6.5) strongly suggested that enzymes serve primarily as hydroxyacetone converting enzymes.

Example 3

Inhibition Studies on Native GlyDH and 2 Mutant GlyDH (A160T & T120N)

1. Construction of the Strains for Production of GlyDH Enzymes 1.1. Construction of the Plasmid pME101-VB01-gldA 1.1.1. Construction of the Plasmid pME101-VB01

The plasmid pME101VB01 is derived from plasmid pME101 and harbors a multiple cloning site containing recognition site sequences specific for the rare restriction endonucleases NheI, SnaBI, PacI, BglII, AvrII, SacII and AgeI following by the adc transcription terminator of *Clostridium acetobutylicum* ATCC824.

For the expression from a low copy vector the plasmid pME101 was constructed as follows. The plasmid pCL1920 (Lerner & Inouye, 1990, NAR 18, 15 p 4631—GenBank AX085428) was PCR amplified using the oligonucleotides PME101F and PME101R and the BstZ17I-XmnI fragment from the vector pTrc99A (Amersham Pharmacia Biotech, Piscataway, N.J.) harboring the lacI gene and the trc promoter was inserted into the amplified vector.

```
PME101F (SEQ ID NO 9):    ccgacagtaagacgggtaagcctg

PME101R (SEQ ID NO 10):   agcttagtaaagccctcgctag
```

A synthetic double-stranded nucleic acid linker comprising the multicloning site and adc transcriptional terminator was used to generate pME101VB01. Two 100 bases oligonucleotides that complement flanked by NcoI or HindIII digested restriction sites were annealed. The 100-base pair product was subcloned into NcoI/HindIII digested plasmid pME101 to generate pME101VB01.

```
pME101VB01 1,
consisting of 100 bases (SEQ ID NO 11):
catgggctagctacgtattaattaaagatctcctagggagctcaccggt TAAAAATAAGAGTTACCTTAAATGGTAACTCTTATTTTTTAggcgcgc
ca pME101VB01 2,
consisting of 100 bases (SEQ ID NO 12):
agcttggcgcgccTAAAAAAATAAGAGTTACCATTTAAGGTAACTCTTA TTTTTAaccggtgagctccctaggagatctttaattaatacgtagctag
cc
``` with:
- a region (underlined lower-case letters) corresponding to the multicloning site
- a region (upper-case letters) corresponding to the adc transcription terminator (sequence 179847 to 179814) of *Clostridium acetobutylicum* ATCC 824 pSOL1 (NC_001988).

1.1.2. Construction of the Plasmid pME101-VB01-gldA

The gene gldA was PCR amplified from genomic DNA of *E. coli* MG1655 using the following oligonucleotides,

```
gldA F, consisting of 28 pb
                        (SEQ ID NO 13)
gacctaggctctaaaggagcaattatgg
```

With:
- a region (underlined letter) homologous to the sequence (4137074 to 4137055) in front of the gene gldA
- a restriction site avrII (bold face letters)

```
gldA R, consisting of 26 pb
                        (SEQ ID NO 14)
cgagctcttattcccactcttgcagg
``` with,
- a region (underlined letter) homologous to the sequence (4135955 to 4135973) the gene gldA
- a restriction SacI (bold face letters)

The PCR amplified fragment was cut with the restriction enzymes avrII and SacI and cloned into the avrII/SacI sites of the vector pME101VB01. The resulted plasmid was named pME101VB01-gldA.

1.2. Construction of the Plasmid pME101-VB01-gldA* (A160T)

1.2.1. Construction of pSCB-gldA*(A160T)

The gene gldA, PCR amplified from genomic DNA of *E. coli* MG1655 using the oligonucleotides gldA F and gldA R was cloned in pSCB (Strataclone®). The resulted plasmid was named pSCB-gldA.

A directed mutagenesis was performed on this plasmid with the following oligonucleotides: gldA*A160TmutDirF and gldA*A160TmutDirR given in Table 3. The resulted plasmid was named pSCB-gldA*(A160T).

1.2.2. Construction of the Plasmid pME101-VB01-gldA* (A160T)

The pSCB-gldA*(A160T) was cut with the restriction enzymes avrII and SacI and the fragment containing gldA* (A160T) was cloned into the avrII/SacI sites of the vector pME101VB01. The resulted plasmid was named pME101VB01-gldA*(A160T).

1.3. Construction of the Plasmid pME101-VB01-gldA* (T120N)

1.3.1. Construction of pSCB-gldA*(T120N)

A directed mutagenesis was performed on the plasmid pSCB-gldA with the following oligonucleotides: gldA* (T120N) MD F and gldA*(T120N) MD R (given in Table 3).

The resulted plasmid was named pSCB-gldA*(T120N).

1.3.2. Construction of the pME101VB01-gldA*(T120N)

The pSCB-gldA*(T120N) was cut with the restriction enzymes avrII and SacI and the fragment containing gldA*(T120N) was cloned into the avrII/SacI sites of the vector pME101VB01. The resulted plasmid was named pME101VB01-gldA*(T120N).

1.4. Introduction of the Plasmids in the Strain *E. coli* MG1655

The plasmids pME101-VB01-gldA, pME101-VB01-gldA*(A160T), pME101VB01-gldA*(T120N) were introduced by electroporation in the strain *E. coli* MG1655 and the strain obtained were named, respectively:

*E. coli* MG1655 pME101-VB01-gldA,
*E. coli* MG1655 pME101-VB01-gldA*(A160T),
*E. coli* MG1655 pME101-VB01-gldA*(T120N).

2. Production of Crude Protein Extracts Enriched in GlyDH Proteins

The 3 strains *E. coli* MG1655 pME101-VB01-gldA, *E. coli* MG1655 pME101-VB01-gldA*(A160T) and *E. coli* MG1655 pME101-VB01-gldA*(T120N) were cultivated in minimal medium with 10 g/l glucose as carbon source in 500 ml baffled Erlenmeyer flasks with 50 ml culture medium. The culture was carried out on a rotary shaker at 200 rpm. The temperature of the culture was maintained at 37° C. and the pH of the medium was buffered with MOPS (initial pH 6.8). Expression of the gene on the pME101-VB01 plasmid was induced by adding 100 µM IPTG at the beginning of the culture. The cultures were stopped at mid-exponential phase. The biomass was harvested by centrifugation, the supernatant was discarded and the pellet was stored at −20° C. before use.

Between 55-65 mg of *E. coli* biomass were resuspended in 9 ml of 100 mM Potassium phosphate pH 7, 0.1 mM DTT, 0.1 mM pyridoxal 5'-phosphate (PLP) and a protease inhibitor cocktail. Cells were sonicated on ice (Branson sonifier, 70 W) during four cycles of 30 sec with 30 sec intervals. After sonication, cells debris were removed by centrifugation at 12000 g for 30 min at 4° C. The crude extracts were desalted using an Econo-Pac 10 DG column (BioRad).

3. Activity Assay for GlyDH

Glycerol dehydrogenase activity was assayed by measuring the initial rate of NADH oxidation with a spectrophotometer at a wavelength of 340 nm and at a constant temperature of 30° C. The reaction mixture using hydroxyacetone as substrate was carried out in 100 mM Mes pH6.5, 0.1 mM FeSO4, 30 mM ammonium sulphate, 0.2 mM NADH, 3-6 ng of crude extracts in a final volume of 1 ml. The reaction mixture was incubated for 5 min at 30° C. and then the reaction was initiated by the addition of the substrate hydroxyacetone at a final concentration of 0.4 mM. Control assay (blank), lacking the substrate was run in parallel and the value measured for the control was subtracted to the value measured for the assay to take into account non-specific oxidation of NADH.

One unit of enzyme activity was defined as the amount of enzyme that consumed 1 µmol substrate per minute under the conditions of the assay. Specific enzyme activity was expressed as units per mg of protein.

4. Characterization of the Inhibition of the GlyDH Enzymes by NAD+

The NAD+ inhibition constant for the three crude extracts over-expressing the GlyDH proteins were determined in the conditions described for the activity assay. Enzyme kinetics with regards to NADH were realised with increasing concentration of NADH between 0.025 and 0.4 mM. Four concentrations of the inhibitor NAD+ were used (0.6-1.2-2.5-4 mM) and the kinetics were recorded for each condition of inhibition. The NAD+ inhibition constant (Ki) of each protein was determined with the module enzyme kinetic from the software Sigma Plot (Systat Software Inc, San Jose Calif.). A model of competitive inhibition was fitted by the software as described in the literature for the inhibition of NAD+ toward NADH for GlyDH enzymes (Nihise et al, 1984). The kinetic parameters calculated for these three proteins were summarized in Table 8.

TABLE 8

Kinetic parameters of GlyDH enzymes toward NADH and inhibition by NAD+

|  | GlyDH | GlyDH*(A160T) | GlyDH*(T120N) |
|---|---|---|---|
| Km (µM) | 43 ± 17 | 86 ± 0.1 | 31 ± 6 |
| Specific activity (nmol/min/mg) | 1240 ± 77 | 1140 ± 42 | 2023 ± 56 |
| kcat (s-1) | 0.8 ± 0.05 | 0.7 ± 0.03 | 1.3 ± 0.04 |
| kcat/Km (M-1s-1) | 1.85E+04 ± 8.6E+03 | 8.5E+03 ± 1.5E+03 | 4.23E+04 ± 9.2E+03 |
| Ki NAD+ (mM) | 0.43 ± 0.19 | 14.79 ± 9.9 | 1.26 ± 0.34 |

The native GlyDH enzyme was highly inhibited by the cofactor NAD+ (Ki=0.43 mM) in contrast to the two mutants. For the protein GlyDH*(A160T), the determination of a precise inhibition constant was difficult with the inhibitor concentrations used. At these NAD+ concentrations, almost no inhibition occurred. For the protein GlyDH*(T120N), the Ki is 3 times higher than that of the native enzyme, which means that the sensitivity to NAD+ of the protein GlyDH*(T120N) is also less important than that of the native enzyme.

Specific activity of native GlyDH enzyme was maintained or even increased in mutant GlyDH.

5. Characterization of the Inhibition of the GlyDH Enzymes by their Substrate

To evaluate the inhibition by the substrate hydroxyacetone, enzyme kinetics were realised on crude extracts. The crude extracts were incubated for 5 min at 30° C. with all compounds of the assay and with different concentration of hydroxyacetone (0.4-2-4-8-16-24-40-70-100 mM) and the reaction was initiated by the addition of the cofactor NADH at a final concentration of 0.2 mM. The hydroxyacetone inhibition constant (Ki) of each protein was determined graphically using a Dixon plot, in which the reciprocal velocity is plotted against the inhibitor concentration (in this case the substrate, hydroxyacetone concentration). The linear part of the curve for each enzyme was used for estimation of Ki, given by intersection of the line with the X axis. The Ki values for the three proteins were summarized in Table 9.

TABLE 9

Inhibition of GlyDH enzymes by hydroxyacetone

| | GlyDH | GlyDH*(A160T) | GlyDH*(T120N) |
|---|---|---|---|
| Ki Hydroxyacetone (mM) | 8.5 | 127 | 163 |

The native GlyDH enzyme was strongly inhibited by an excess of substrate as already described in the literature (Nihise et al, 1984) with a Ki of 11.6 mM, close to our value of 8.5 mM. The two mutants GlyDH*(A160T) and GlyDH*(T120N) are far less sensitive to hydroxyacetone inhibition, with Ki values increased by a factor of more than 10.

6. Characterization of the Inhibition of the GlyDH Enzymes by their Product

To evaluate the inhibition by the product 1,2-propanediol, enzyme kinetics were realised on crude extracts. The crude extracts were incubated for 5 min at 30° C. with all compounds of the assay and with different concentration of 1,2-propanediol (0.4-2-4-8-16-24-40-70-100 mM) and the reaction was initiated by the addition of the cofactor NADH at a final concentration of 0.2 mM. The substrate hydroxyacetone was used at saturation, 0.4 mM for gldA and 4 mM for gldA*(A160T) and gldA*(T120N).

The native GlyDH enzyme lost 50% of its maximum activity (measured at substrate saturation) in presence of 40 mM propanediol, in contrast the mutants GlyDH*(A160T) and GlyDH*(T120N) lost only between 13 and 15% of their maximum activity (measured at substrate saturation) in presence of 40 mM propanediol. At a concentration of 100 mM propanediol, the mutants GlyDH lost between 24 and 30% of their maximum activity, whereas the native GlyDH lost 65% of its maximum activity.

To summarize, the properties of the two mutants GlyDH were very similar. However, the mutants GlyDH are less inhibited by the co-factor NAD+, their substrate and their product than the native GlyDH enzyme.

Example 4

Construction of Two E. coli 1,2-propanediol Producer Strains Expressing Wildtype or Modified GlyDH and Assessment of 1,2-propanediol Production 1. Construction of the Modified Strain E. coli MG1655, mgsA*(H21Q)::Km, Δedd-eda, ΔgloA, ΔaldA, ΔaldB, ΔarcA, Δndh (pME101-VB01-yqhD*(G149E)-gldA)

1.1. Construction of a Modified Strain E. coli ΔgloA::Cm

The gene gloA was inactivated in strain E. coli MG1655 by inserting a chloramphenicol antibiotic cassette and deleting most of the gene concerned using the technique described in Protocol 1 with the oligonucleotides given in Table 4. The deletion was checked by a PCR analysis with the appropriate oligonucleotides given in Table 5. The resulting strain was named E. coli MG1655 ΔgloA::Cm.

1.2. Construction of a Modified Strain E. coli ΔgloA::Cm Δedd-eda::Km 1.2.1. Construction of a Modified Strain E. coli Δedd-eda::Km The genes edd-eda were inactivated in strain E. coli MG1655 by inserting a kanamycin antibiotic cassette and deleting most of the gene concerned using the technique described in Protocol 1 with the oligonucleotides given in Table 4. The deletion was checked by a PCR analysis with the appropriate oligonucleotides given in Table 5.

The resulting strain was named E. coli MG1655 Δedd-eda::Km.

1.2.2. Construction of a Modified Strain E. coli ΔgloA::Cm, Δedd-eda::Km.

The deletion of the genes edd-eda by replacement of the genes by a kanamycin resistance cassette in the strain E. coli Δedd-eda::Km was performed by the technique of transduction with phage P1 according to Protocol 2.

Protocol 2: Transduction with phage P1 for deletion of a gene

The deletion of the chosen gene by replacement of the gene by a resistance cassette (kanamycin or chloramphenicol) in the recipient E. coli strain was performed by the technique of transduction with phage P1. The protocol was in two steps, (i) the preparation of the phage lysate on the strain MG1655 with a single gene deleted and (ii) the transduction of the recipient strain by this phage lysate.

Preparation of the Phage Lysate

Seeding with 100 μl of an overnight culture of the strain MG1655 with a single gene deleted of 10 ml of LB+Cm 30 μg/ml+glucose 0.2%+CaCl$_2$ 5 mM.

Incubation for 30 min at 37° C. with shaking.

Addition of 100 μl of phage lysate P1 prepared on the wild type strain MG1655 (approx. 1×10$^9$ phage/ml).

Shaking at 37° C. for 3 hours until all cells were lysed.

Addition of 200 μl of chloroform, and vortexing.

Centrifugation for 10 min at 4500 g to eliminate cell debris.

Transfer of supernatant in a sterile tube and addition of 200 μl of chloroform.

Storage of the lysate at 4° C.

Transduction

Centrifugation for 10 min at 1500 g of 5 ml of an overnight culture of the E. coli recipient strain in LB medium.

Suspension of the cell pellet in 2.5 ml of MgSO$_4$ 10 mM, CaCl$_2$ 5 mM.

Control tubes: 100 μl cells

100 μl phages P1 of the strain MG1655 with a single gene deleted.

Tube test: 100 μl of cells+100 μl phages P1 of strain MG1655 with a single gene deleted.

Incubation for 30 min at 30° C. without shaking.

Addition of 100 μl sodium citrate 1 M in each tube, and vortexing.

Addition of 1 ml of LB.

Incubation for 1 hour at 37° C. with shaking

Plating on dishes LB+Cm 30 μg/ml after centrifugation of tubes for 3 min at 7000 rpm.

Incubation at 37° C. overnight.

The antibiotic-resistant transformants were then selected and the insertion of the deletion was checked by a PCR analysis with the appropriate oligonucleotides given in Table 5.

The deletion was checked by a PCR analysis with the appropriate oligonucleotides given in Table 5 as well as the other deletion already present in the strain.

The resulting strain was named E. coli ΔgloA:: Cm, Δedd-eda::Km.

1.3. Construction of a Modified Strain E. coli MG1655 Δedd-eda ΔgloA

The antibiotic resistance cassettes were eliminated in the strain E. coli Δedd-eda::Km, ΔgloA::Cm according to Protocol 3.

Protocol 3: Elimination of resistance cassettes (FRT system)

The chloramphenicol and/or kanamycin resistance cassettes were eliminated according to the following technique. The plasmid pCP20 carrying the FLP recombinase acting at the FRT sites of the chloramphenicol and/or kanamycin resistance cassettes was introduced into the strain by electroporation. After serial culture at 42° C., the loss of the antibiotic resistance cassettes was checked by PCR analysis with the oligonucleotides given in Table 5.

The presence of the modifications previously built in the strain was checked using the oligonucleotides given in Table 5.

The strain obtained was named E. coli MG1655 Δedd-eda ΔgloA.

1.4. Construction of the Modified Strain E. coli MG1655 Δedd-eda ΔgloA, ΔaldA::Cm 1.4.1. Construction of the Modified Strain E. coli MG1655 ΔaldA::Cm The gene aldA was inactivated in strain E. coli MG1655 by inserting a chloramphenicol antibiotic cassette and deleting most of the gene concerned using the technique described in Protocol 1 with the oligonucleotides given in Table 4. The deletion was checked by a PCR analysis with the appropriate oligonucleotides given in Table 5. The resulting strain was named E. coli MG1655 ΔaldA::Cm.

1.4.2. Construction of the Modified Strain E. coli MG1655 Δedd-eda ΔgloA, ΔaldA::Cm The deletion of the gene aldA by replacement of the gene by a chloramphenicol resistance cassette in the strain E. coli MG1655 Δedd-eda ΔgloA was performed by the technique of transduction with phage P1 (Protocol 2).

The deletion ΔaldA::Cm and the others modifications were checked using the oligonucleotides described in Table 5.

The resulting strain was named E. coli MG1655 Δedd-eda ΔgloA, ΔaldA::Cm 1.5. Construction of the Modified Strain E. coli MG1655 Δedd-eda, ΔgloA, ΔaldA::Cm, ΔaldB::Km 1.5.1. Construction of the Modified Strain E. coli MG1655 ΔaldB::Km The gene aldB was inactivated in strain E. coli MG1655 by inserting a Kanamycin antibiotic cassette and deleting most of the gene concerned using the technique described in Protocol 1 with the oligonucleotides given in Table 4. The deletion was checked by a PCR analysis with the appropriate oligonucleotides given in Table 5.

The resulting strain was named E. coli MG1655 ΔaldB::Km.

1.5.2. Construction of the Modified Strain E. coli MG1655 Δedd-eda ΔgloA, ΔaldA::Cm, ΔaldB::Km The deletion of the gene aldA by replacement of the gene by a Kanamycin resistance cassette in the strain E. coli MG1655 Δedd-eda ΔgloA ΔaldA::Cm, was performed by the technique of transduction with phage P1 (Protocol 2).

The deletion ΔaldB::Km and the others modifications were checked using the oligonucleotides described in Table 5.

The resulting strain was named E. coli MG1655 Δedd-eda ΔgloA, ΔaldA::Cm, ΔaldB::Km.

1.6. Construction of the Modified Strain E. coli MG1655 Δedd-eda ΔgloA, ΔaldA, ΔaldB The antibiotic resistance cassettes were eliminated in the strain E. coli MG1655 Δedd-eda ΔgloA, ΔaldA::Cm, ΔaldB::Km according to Protocol 3.

The loss of the antibiotic resistance cassettes was checked by PCR analysis with the oligonucleotides given in Table 5.

The presence of the modifications previously built in the strain was also checked using the oligonucleotides given in Table 5.

The strain obtained was named E. coli MG1655 Δedd-eda ΔgloA, ΔaldA, ΔaldB.

1.7. Construction of the Modified Strain E. coli MG1655 Δedd-eda ΔgloA, ΔaldA, ΔaldB, ΔarcA::Km 1.7.1. Construction of the Modified Strain E. coli MG1655 ΔarcA::Km The gene arcA was inactivated in strain E. coli MG1655 by inserting a Kanamycin antibiotic cassette and deleting most of the gene concerned using the technique described in Protocol 1 with the oligonucleotides given in Table 4. The deletion was checked by a PCR analysis with the appropriate oligonucleotides given in Table 5.

The resulting strain was named E. coli MG1655 ΔarcA::Km.

1.7.2. Construction of the Modified Strain E. coli MG1655 Δedd-eda ΔgloA, ΔaldA, ΔaldB, ΔarcA::Km The deletion of the gene arcA by replacement of the gene by a Kanamycin resistance cassette in the strain E. coli Δedd-eda ΔgloA, ΔaldA, ΔaldB, ΔarcA::Km, was performed by the technique of transduction with phage P1 (Protocol 2)

The deletion ΔarcA::Km and the others modifications were checked using the oligonucleotides described in Table 5.

The strain obtained was named E. coli MG1655 Δedd-eda ΔgloA, ΔaldA, ΔaldB, ΔarcA::Km.

1.8. Construction of the Modified Strain E. coli MG1655 Δedd-eda ΔgloA, ΔaldA, ΔaldB, ΔarcA::Km, Δndh::Cm 1.8.1. Construction of the Modified Strain E. coli MG1655 Δndh::Cm The genes ndh was inactivated in strain E. coli MG1655 by inserting a chloramphenicol resistance cassette and deleting most of the gene concerned using the technique described in Protocol 1 with the oligonucleotides given in Table 4. The deletion was checked by a PCR analysis with the appropriate oligonucleotides given in Table 5.

The resulting strain was named E. coli MG1655 Δndh::Cm.

1.8.2. Construction of the Modified Strain E. coli MG1655 Δedd-eda ΔgloA, ΔaldA, ΔaldB, ΔarcA::Km, Δndh::Cm The deletion of the gene ndh by replacement of the gene by a chloramphenicol resistance cassette in the strain E. coli Δedd-eda ΔgloA, ΔaldA, ΔaldB, ΔarcA::Km, was performed by the technique of transduction with phage P1 (Protocol 2).

The deletion Δndh::Cm and the others modifications were checked using the oligonucleotides described in Table 5.

The strain obtained was named E. coli MG1655 Δedd-eda ΔgloA, ΔaldA, ΔaldB, ΔarcA::Km, Δndh::Cm.

1.9. Construction of the Modified Strain E. coli MG1655 Δedd-eda, ΔgloA, ΔaldA, ΔaldB, ΔarcA, Δndh The antibiotic resistance cassettes were eliminated in the strain E. coli MG1655 Δedd-eda ΔgloA, ΔaldA, ΔaldB, ΔarcA::Km, Δndh::Cm according to Protocol 3.

The loss of the antibiotic resistance cassettes was checked by PCR analysis with the oligonucleotides given in Table 5. The presence of the modifications previously built in the strain was also checked using the oligonucleotides given in Table 5.

The strain obtained was named E. coli MG1655 Δedd-eda ΔgloA, ΔaldA, ΔaldB, ΔarcA, Δndh.

1.10. Construction of the Modified Strain E. coli MG1655 Δedd-eda, ΔgloA, ΔaldA, ΔaldB, ΔarcA, Δndh (pME101VB01-yqhD*(G149E)-gldA)

1.10.1. Construction of the Plasmid pME101-VB01-yqhD*(G149E)-gldA 1.10.1.1. Construction of the Plasmid pSCB-yqhD*(G149E)

The gene yqhD, PCR amplified from genomic DNA of E. coli MG1655 using the oligonucleotides yqhD F and yqhD R was cloned in pSCB (Strataclone®). The resulted plasmid was named pSCB-yqhD. A directed mutagenesis was performed on this plasmid with the following oligonucleotides: yqhD*G149EmutDirF (consisting of 45 pb, ggttcagaatc-caacgcagaagcggtgatAtcccgtaaaaccacaggc, SEQ ID NO 15) and yqhD*G149EmutDirR (consisting of 45 pb gcctgtggttt-tacgggaTatcaccgcttctgcgttggattctgaacc, SEQ ID NO 16). The two oligonucleotides were homologous to the region 3153803 to 3153850. In bold face letter, bases which were changed to create the mutation G149E and capital letter, the base which were changed to create EcoRV restriction site. The resulted plasmid was named pSCB-yqhD*(G149E).

1.10.1.2. Construction of the pME101VB01-yqhD*(G149E)-gldA

The pSCB-yqhD*(G149E) was cut with the restriction enzymes BspHI and NheI and the fragment containing yqhD*(G149E) was cloned into the NcoI/NheI sites of the vector pME101VB01. The resulting plasmid was named pME101VB01-yqhD*(G149E).

The gene gldA was PCR amplified from genomic DNA of E. coli MG1655 using the oligonucleotides, gldA F (SEQ ID NO 13) and gldA R (SEQ ID NO 14)

The PCR amplified fragment was cut with the restriction enzymes avrII and SacI and cloned into the avrII/SacI sites of the vector pME101VB01-yqhD*(G149E). The resulted plasmid was named pME101VB01-yqhD*(G149E)-gldA.

1.10.2. Construction of the Modified Strain E. coli MG1655 Δedd-eda, ΔgloA, ΔaldA, ΔaldB, ΔarcA, Δndh (pME101VB01-yqhD*(G149E)-gldA)

The plasmid pME101VB01-yqhD*(G149E)-gldA was introduced by electroporation into the strain E. coli MG1655 Ptrc01-gapA::cm, Δedd-eda, ΔgloA, ΔaldA, ΔaldB, ΔarcA, Δndh.

The strain obtained was named E. coli MG1655 Δedd-eda, ΔgloA, ΔaldA, ΔaldB, ΔarcA, Δndh (pME101VB01-yqhD*(G149E)-gldA)

1.11. Construction of the Modified Strain E. coli MG1655 mgsA*(H21Q)::Km Δedd-eda, ΔgloA, ΔaldA, ΔaldB, ΔarcA, Δndh (pME101VB01-yqhD*(G149E)-gldA)

1.11.1. Construction of the Modified Strain E. coli MG1655 mgsA*(H21Q)::Km 1.11.1.1. Construction of the Modified Strain E. coli MG1655 mgsA*(H21Q)

A mutation was introduced in the mgsA gene in order to obtain the mutant protein MgsA*(H21Q). The technique used to build this modification was described by Heermann et al. (2008), Microbial Cell Factories. 7 (14): 1-8.

The following oligonucleotides were used to amplify the rpsL-Neo cassette:

1. mgsA*(H21Q) ::rpsL-Neo F, consisting in 105 pb,
(SEQ ID NO 17)
gttaactacggatgtacattatggaactgacgactcgcactttacctgc gcggaaacatattgcgctggtggcacacgatcaggcctggtgatgatgg cgggatc with, a region (underlined letter) homologous to the sequence of the gene mgsA.

a region (bold face letter) to amplified rpsL-Neo cassette.

2. mgsA*(H21Q) ::rpsL-Neo R
(SEQ ID NO 18)
gggaaattaagttaccggtagtgcctgttgcatacagtacgtgttgttc cagtaacggttgatgccgttccacccagctcatcagcatctgtttgcat tcagaagaactcgtcaagaagg with, a region (underlined letter) homologous to the sequence of the gene mgsA with to mutation, the first one (in red) to create the mutation H21Q and the second one (in yellow) to create the restriction site AlwN1.

a region (bold face letter) to amplified rpsL-Neo cassette.

The fragment obtained was introduced into the strain MG1655 rpsL*(built as described in Heermann et al.) according to Protocol 1. The strain obtained is checked by PCR and sequence analysis. The strain obtained is named E. coli mgsA*(H21Q)::rpsL-Neo.

The deletion of the cassette rpsL-Neo was performed according to Protocol 1. The fragment transformed was obtained by the restriction with NcoI and SacI of the plasmid pETTOPO-mgsA*(H21Q).

The modification was checked by PCR using oligonucleotides described in Table 5.

The strain obtained is named strain E. coli MG1655 mgsA*(H21Q).

1.11.1.2. Construction of the Modified Strain E. coli MG1655 mgsA*(H21Q)::Km

A kanamycin resistance cassette was introduced in 3' of mgsA*(H21Q) open reading frame using the following primers:

mgsA ::Km F consisting of 100 bp:
(SEQ ID NO 19)
tccagtcgccgcatttcaacgacgcggtcgatattctgatccccgatta tcagcgttatctcgcggaccgtctgaagtaatgtaggctggagctgctt cg with:

a region (underlined letters) homologous to the end of mgsA*(H21Q) ORF, a region (Bold letter) to amplified Kanamycin cassette.

mgsA ::Km R consisting of 100 bp:

(SEQ ID NO 20)

<u>tgtggaaatactgaaaaatctggatgtgccggtggcgagaaaaccgtaa</u>

<u>gaaacaggtggcgtttgccacctgtgcaata</u>catatgaatatcctcctt ag a region (underlined letters) homologous to the end of helD ORF, a region (Bold letter) to amplified Kanamycin cassette.

The fragment obtained was introduced into the strain MG1655 mgsA*(H21Q) according to Protocol 1. The strain obtained was checked by PCR. The strain obtained was named *E. coli* mgsA*(H21Q)::Km 1.11.2. Construction of the Modified Strain *E. coli* MG1655 mgsA*(H21Q)::Km ΔeddA-eda, ΔgloA, ΔaldA, ΔaldB, ΔarcA, Δndh (pME101VB01-yqhD*(G149E)-gldA)

The replacement of the mgsA with the mgsA*(H21Q)::Km into the strain *E. coli* Δedd-eda ΔgloA, ΔaldA, ΔaldB, ΔarcA, Δndh (pME101VB01-yqhD*(G149E)-gldA) was performed by the technique of transduction with phage P1. IPTG was added to the culture to promote the expression of the genes borne on the plasmid.

The modifications mgsA*(H21Q)::Km and the others deletion were checked using the oligonucleotides described in Table 5.

2. Construction of the Modified Strain *E. coli* MG1655 mgsA*(H21Q)::Km, Δedd-eda, ΔgloA, ΔaldA, ΔaldB, ΔarcA, Δndh (pME101-VB01-yqhD*(G149E)-gldA* (A160T))

2.1. Construction of the Plasmid (pME101-VB01-yqhD* (G149E)-gldA*(A160T))

2.1.1. Construction of the Plasmid pSCB-yqhD*(G149E)

This plasmid was built previously.

2.1.2. Construction of the Plasmid (pME101VB01-yqhD* (G149E)-gldA*(A160T)

The pSCB-yqhD*(G149E) is cut with the restriction enzymes BspHI and NheI and the fragment containing yqhD* (G149E) was cloned into the NcoI/NheI sites of the vector pME101VB01. The resulting plasmid was named pME101VB01-yqhD*(G149E).

The pSCB-gldA*(A160T) (see example 3) was cut with the restriction enzymes avrII and SacI and the fragment containing gldA*(A160T) was cloned into the avrII/SacI sites of the vector pME101VB01-yqhD*(G149E). The resulted plasmid was named pME101VB01-yqhD*(G149S)-gldA* (A160T).

2.2. Construction of the Modified Strain *E. coli* MG1655 Δedd-eda, ΔgloA, ΔaldA, ΔaldB, ΔarcA, Δndh (pME101-VB01-yqhD*(G149E)-gldA*(A160T))

The plasmid pME101-VB01-yqhD*(G149E)-gldA* (A160T) was introduced by electroporation into the strain *E. coli* MG1655 Δedd-eda, ΔgloA, ΔaldA, ΔaldB, ΔarcA, Δndh.

The strain obtained was named *E. coli* MG1655 Δedd-eda, ΔgloA, ΔaldA, ΔaldB, ΔarcA, Δndh (pME101-VB01-yqhD* (G149E)-gldA*(A160T)).

2.3. Construction of the Modified Strain *E. coli* MG1655 mgsA*(H21Q)::Km, Δedd-eda, ΔgloA, ΔaldA, ΔaldB, ΔarcA, Δndh (pME101-VB01-yqhD*(G149E)-gldA* (A160T))

The replacement of the mgsA with the mgsA*(H21Q)::Km into the strain *E. coli* Δedd-eda ΔgloA, ΔaldA, ΔaldB, ΔarcA, Δndh (pME101VB01-yqhD*(G149E)-gldA*(A160T)) was performed by the technique of transduction with phage P1. IPTG was added to the culture to promote the expression of the genes borne on the plasmid.

The modifications mgsA*(H21Q)::Km and the other deletions were checked using the oligonucleotides described in Table 5.

The strain obtained was named *E. coli* MG1655 mgsA* (H21Q)::Km, Δedd-eda, ΔgloA, ΔaldA, ΔaldB, ΔarcA, Δndh (pME101-VB01-yqhD*(G149E)-gldA*(A160T)).

3. Assessment of 1,2-propanediol Production in Two *E. coli* Isogenic Strains Differing Only in the gldA Alleles The two strains described above were cultivated in an Erlenmeyer flask assay (500 ml flasks with 50 ml of medium) under aerobic conditions in minimal medium MML11PG1_100 (see composition in Table 10) with 20 g/l glucose as sole carbon source. Spectinomycin was added at a concentration of 50 mg/l.

TABLE 10 composition of minimal medium MML11PG1_100.

| Constituent | Concentration (g/l) |
|---|---|
| EDTA | 0.0084 |
| $CoCl_2\ 6H_2O$ | 0.0025 |
| $MnCl_2\ 4H_2O$ | 0.0150 |
| $CuCl_2\ 2H_2O$ | 0.0015 |
| $H_3BO_3$ | 0.0030 |
| $Na_2MoO_4\ 2H_2O$ | 0.0025 |
| $Zn(CH_3COO)_2\ 2H_2O$ | 0.0130 |
| Fe(III) citrate $H_2O$ | 0.1064 |
| Citric acid | 1.70 |
| $KH_2PO_4$ | 1.65 |
| $K_2HPO_4\ 3H_2O$ | 0.92 |
| $(NH_4)_2HPO_4$ | 0.40 |
| $(NH_4)_2SO_4$ | 4.88 |
| $MgSO_4\ 7H_2O$ | 1.00 |
| $CaCl_2\ 2H_2O$ | 0.08 |
| Thiamine | 0.01 |
| Glucose or Sucrose | 20.00 |
| MOPS buffer | 40.00 |

The pH of the medium was adjusted to 6.8 with sodium hydroxide

The culture was carried out at 37° C. and the pH was maintained by buffering the culture medium with MOPS.

At the end of the culture, 1,2-propanediol, and residual glucose in the fermentation broth were analysed by HPLC using a Biorad HPX 97H column for the separation and a refractometer for the detection. The yields of 1,2-propanediol over glucose were then calculated.

TABLE 11 production of 1,2-propanediol in minimal medium with glucose as carbon source.

| Strain | Carbon source | 1,2-propanediol yield (g/g carbon source) |
|---|---|---|
| *E. coli* MG1655 mgsA*(H21Q)::Km ΔgloA Δedd-eda ΔaldA ΔaldB ΔarcA Δndh (pME101VB01-yqhD*(G149E)-gldA) | glucose | 0.116 +/− 0.006 (n = 3) |
| *E. coli* MG1655 mgsA*(H21Q)::Km ΔgloA Δedd-eda ΔaldA ΔaldB ΔarcA Δndh (pME101VB01-yqhD*(G149E)-gldA*(A160T)) | glucose | 0.133 +/− 0.009 (n = 3) | n is the number of repetitions of the same experiment - The figures given are the mean and standard deviation of the figures obtained for n repetitions.

The yield of production of 1,2-propanediol in the *E. coli* strain with a mutant GlyDH enzyme, encoded by the gldA* (A160T) allele, was improved as compared with the isogenic strain with a native GlyDH.

Example 5

Production of 1,2-propanediol by *E. coli* with a Mutant MGS, a Mutant YqhD and a Mutant GlyDH on Glucose and Sucrose 1. Construction of the Modified Strain *E. coli* MG1655 mgsA*(H21Q), Δedd-eda, ΔgloA, ΔaldA, ΔaldB, ΔarcA, Δndh (pME101-VB01-yqhD*(G149E)-gldA*(A160T)))

The construction of this strain was described in example 4.

2. Construction of the Modified Strain *E. coli* MG1655 mgsA*(H21Q), Δedd-eda, ΔgloA, ΔaldA, ΔaldB, ΔarcA, Δndh (pME101-VB01-yqhD*(G149E)-gldA*(A160T)) (pBBR1MCS5-cscBKAR)

2.1. Construction of the Plasmid pBBR1MCS5-cscBKAR

The plasmid pKJL101.1 (Jahreis et al. (2002), J. Bacteriol. 184:5307-5316) was digested by EcoRI. The fragment containing the cscBKAR gene was cloned in pBBR1MCS5 (Kovach et al. (1995), Gene, 166 175-176) also digested by EcoRI.

The plasmid obtained was named pBBR1MCS5-cscBKAR.

2.2. Construction of the Modified Strain *E. coli* MG1655 mgsA*(H21Q), Δedd-eda, ΔgloA, ΔaldA, ΔaldB, ΔarcA, Δndh (pME101-VB01-yqhD*(G149E)-gldA*(A160T)) (pBBR1MCS5-cscBKAR)

The plasmid pBBR1MCS5-cscBKAR was introduced by electroporation in the strain *E. coli* MG1655 mgsA*(H21Q), Δedd-eda, ΔgloA, ΔaldA, ΔaldB, ΔarcA, Δndh. pME101-VB01-yqhD*(G149E)-gldA*(A160T))

The strain obtained was named strain *E. coli* MG1655 mgsA*(H21Q), Δedd-eda, ΔgloA, ΔaldA, ΔaldB, ΔarcA, Δndh (pME101-VB01-yqhD*(G149E)-gldA*(A160T)) (pBBR1MCS5-cscBKAR).

3. Assessment of 1,2-propanediol Production in Two *E. coli* with a Mutant MGS, a Mutant YqhD and a Mutant GlyDH on Glucose and Sucrose The two strains obtained as described above were cultivated in an Erlenmeyer flask assay (500 ml flasks with 50 ml of medium) under aerobic conditions in minimal medium MML11PG1_100 (see composition in Table 10) with 20 g/l glucose or sucrose as sole carbon source. Spectinomycin was added at a concentration of 50 mg/l.

The culture was carried out at 37° C. and the pH was maintained by buffering the culture medium with MOPS.

At the end of the culture, 1,2-propanediol, and residual glucose or sucrose in the fermentation broth were analysed by HPLC using a Biorad HPX 97H column for the separation and a refractometer for the detection. The yields of 1,2-propanediol over glucose or sucrose were then calculated.

TABLE 12 production of 1,2-propanediol in minimal medium with glucose or sucrose as carbon source.

| Strain | Carbon source | 1,2-propanediol yield (g/g carbon source) |
| --- | --- | --- |
| *E. coli* MG1655 mgsA*(H21Q)::Km ΔgloA Δedd-eda ΔaldA ΔaldB ΔarcA Δndh (pME101VB01-yqhD*(G149E)-gldA*(A160T)) | glucose | 0.133 +/− 0.009 (n = 3) |
| *E. coli* MG1655 mgsA*(H21Q)::Km ΔgloA Δedd-eda ΔaldA ΔaldB ΔarcA Δndh (pME101VB01-yqhD*(G149E)-gldA*(A160T)) (pBBR1MCS5-cscBKAR) | sucrose | 0.196 +/− 0.007 (n = 3) | n is the number of repetitions of the same experiment - The figures given are the mean and standard deviation of the figures obtained for n repetitions.

The yield of 1,2-propanediol in an *E. coli* strain with a mutant GlyDH was improved on sucrose as sole carbon source as compared with glucose.

Example 6

Construction of Two *Saccharomyces cerevisiae* 1,2-propanediol Producer Strains Expressing Wildtype or Modified GlyDH and Assessment of 1,2-propanediol Production 1—Construction of Two *S. cerevisiae* Strains CENPK Δgpd2, Δtpi1, gldA*(A160T), yqhD, mgsA*(H21Q) and CENPK Δgpd2, Δtpi1, gldA*(A160T), yqhD*(G149E), mgsA*(H21Q)

1-1. Construction of *S. cerevisiae* Strain CENPK Δgpd2, gldA*(A160T).

The *S. cerevisiae* strain used was CEN.PK2-1C (MATa; ura3-52; trp1-289; leu2-3,112; his3 Δ1; MAL2-8C; SUC2) from Euroscarf.

The gene GPD2 was inactivated by transforming the strain CEN.PK2-1C with a PCR fragment corresponding to pTDH3-gldA*(A160T)-CYCt-pTEF1-ble-TEF1t cassette, built using the "short flanking homology" (SFH) method described by Guldener et al. (1996). The pTDH3-gldA*(A160T)-CYCt-pTEF1-ble-TEF1t cassette was constructed using long PCR-based fusion of several fragments as described by Shevchuk et al. (2004).

pTDH3 and CYCt were amplified from the plasmid p406TDH3 (Addgene) using pTDH3/GPD2 F and pTDH3 R primers and CYCt/gldA F and CYCt/Zeo R primers respectively. gldA*(A160T)—was amplified from pSCB gldA*(A160T)—using primers gldA/TDH3F and gldA/CYCtR.

pTEF1-ble-TEF1t was amplified from the plasmid pUG66 from Euroscarf using Zeo/CYCt F and ZEO/GPD2 R as primers.

All fragments were amplified using primers having overlapping ends as described in Table 13. Each fragment was then purified.

100 ng of each fragment was used in a PCR experiment without primers, using low annealing conditions allowing their simultaneous fusion.

The unpurified product obtained in this step was used as a matrix a in a PCR experiment at high Tm, using pTDH3/GPD2 F and ZEO/GPD2 R primers having an extension of 40 bp homologous to the 40 first and 40 last bp of the GPD2 locus (Table 13).

This fragments was integrated in the GPD2 locus, replacing the GPD2 open reading frame. The transformation method used was the lithium acetate method described by Schiestl and Gietz (1989). The strain CENPK, Δgpd2, gldA*(A160T) was selected on YEPD rich medium (1% bacto yeast extract, 2% bactopeptone, 2% glucose) supplemented with 75

µg/ml of phleomycin (Cayla, France). The integration of gldA*(A160T) and the deletion of GPD2 gene were confirmed by PCR on genomic DNA extracted, using GPD2 ver F and GPD2 ver R primers (Table 13).

This resulted in the heterologous expression of gldA* (A160T) and deletion of GPD2. The resulting strain was named CENPK Δgpd2, gldA*(A160T).

TABLE 13

| Primer Name | Sequence | Description |
|---|---|---|
| pTDH3/GPD2 F | ATG CTT GCT GTC AGA AGA TTA ACA AGA TAC ACA TTC CTT AGT TTA TCA TTA TCA ATA CTC G (SEQ ID NO 21) | The underlined 40 nucleotides correspond to the 40 first bp of GPD2 gene 21 nucleotides in bold are homologous to the 21 first bp of pTDH3 |
| pTDH3 R | ATCCTCGAAACTAAGTTCTTGGT (SEQ ID NO 22) | 23 nucleotides homologous to the 23 last bp of pTDH3 |
| gldA/TDH3F | AAA CAC CAG AAC TTA GTT TCG AAC TAG TTT ATT CCC ACT CTT (SEQ ID NO 23) | The underlined 22 nucleotides underlined correspond to the last bp of pTDH3 20 nucleotides in bold are homologous to the 20 first bp of gldA or gldA* (A160T) |
| gldA/CYCtR | TCA AAT ATA AAT AAC GTT CTT AAT ACT AAC ATA ACT ATA AAC TAG TAT GGA CCG CAT TAT TC (SEQ ID NO 24) | The underlined 42 nucleotides correspond to the 42 first bp of CYCt 20 nucleotides in bold are homologous to the 20 last bp of gldA or gldA*(A160I) |
| CYCt/gldA F | CCT GGA TCT ATT TAC CCG GTG ATT GAA TAA TGC GGT CCA TAC TAG TTT ATA GTT ATG TTA GTA TTA (SEQ ID NO 25) | The underlined 46 nucleotides correspond to the 46 last bp gldA or gldA 20 nucleotides in bold are homologous to the 20 first bp of CYCt |
| CYCt/Zeo R | GAG GCA AGC TAA ACA GAT CTC TAG ACC TAG GTA CCC GCC GGC AAA TTA AAG CCT TCG AGC (SEQ ID NO 26) | The underlined 40 nucleotides correspond to the 40 first bp of ble gene 20 nucleotides in bold are homologous to the 20 last bp of CYCt |
| Zeo/CYCt F | GCT TGA GAA GGT TTT GGG ACG CTC GAA GGC TTT AAT TTC CTA GGT CTA GAG ATC TGT TTA GC (SEQ ID NO 27) | The underlined 40 nucleotides correspond to the 40 last bp of CYCt 22 nucleotides in bold are homologous to the 22 first bp of TEF1p |
| ZEO/GPD2 R | CTA TTC GTC ATC GAT GTC TAG CTC TTC AAT CAT CTC CGG TCC ACT AGT GGA TCT GAT ATC ACC T (SEQ ID NO 28) | The underlined 40 nucleotides correspond to the 40 last bp of GPD2 gene 24 nucleotides in bold are homologous to the 24 last bp of TEF1t |
| GPD2 ver F | ATG CTT GCT GTC AGA AGA TT (SEQ ID NO 29) | 20 nucleotides homologous to the 20 first bp of GPD2 gene |
| GPD2 ver R | TAG TAT GGA CCG CAT TAT TC (SEQ ID NO 30) | 20 nucleotides homologous to the 20 last nucleotides of gldA and gldA*(A160I) |

1-2. Construction of Two S. cerevisiae Strains CENPK Δgpd2, gldA*(A160T), yqhD and CENPK Δgpd2, gldA*(A160T), yqhD*(G149E)

The strain used was CENPK, Δgpd2, gldA*(A160T), previously built. The expression of yqhD or yqhD*(G149E) was realised by transforming the strains with a PCR fragment corresponding to a pTEF1-yqhD-CYCt-pTEF1-nat1-TEF1t cassette or pTEF1-yqhD*(G149E)-CYCt-pTEF1-nat1-TEF1t cassette using the "short flanking homology" (SFH) method.

The pTEF1-yqhD-CYCt-pTEF1-nat1-TEF1t cassette or pTEF1-yqhD*(G149E)-CYCt-pTEF1-nat1-TEF1t cassette were constructed using long PCR-based fusion of several fragments.

pTEF1 and CYCt were amplified from the plasmid p405TEF1 (Addgene) using pTEF1/URA3 F and pTEF R primers and CYCt/yqhD F and CYCt/Nat1R primers respectively. yqhD and yqhD* were amplified respectively from pSCB-yqhD and pSCB yqhD*(G149E) using primers yqhD/TEF-F and yqhD/CYCtR.

pTEF1-nat1-TEF1t was amplified from the plasmid pAG35 from Euroscarf using Nat1/CYCt F and Nat1/Leu2 as primers.

All fragments were amplified using primers having overlapping ends as described in Table 14. Each fragment was then purified.

100 ng of each fragment was used in a PCR experiment without primers using low annealing conditions allowing their simultaneous fusion.

The unpurified product obtained in this step was used as a matrix in a PCR experiment with at high Tm, using pTEF1/LEU2 F and Nat1/Leu2 primers having an extension of 40 bp homologous to the 40 first and 40 last bp of the LEU2 locus (Table 14).

These fragments were integrated in the LEU2 locus, replacing the LEU2 open reading frame.

The transformation method used was the lithium acetate method. The strain CENPK, Δgpd2, gldA*(A160T) was transformed either by pTEF1-yqhD-CYCt-pTEF1-nat1-TEF1t cassette or by pTEF1-yqhD*(G149E)-CYCt-pTEF1-nat1-TEF1t to obtained CENPK, Δgpd2, gldA*(A160T), yqhD and CENPK, Δgpd2, gldA*(A160T), yqhD*(G149E). Transformants were selected on YEPD rich medium (1% bacto yeast extract, 2% bactopeptone, 2% glucose) supplemented with 50 µg/ml of nourseothricine (Weber bioagents, Germany). The integration of yqhD or yqhD*(G149E) were confirmed by PCR on genomic DNA extracted, using YQHD ver F and YQHD ver R primers (Table 14). This resulted in the heterologous expression of yqhD and yqhD*(G149E). The resulting strains were named CENPK Δgpd2, gldA*(A160T), yqhD and CENPK Δgpd2, gldA*(A160T), yqhD*(G149E).

TABLE 14

| Primer Name | Sequence | Description |
|---|---|---|
| pTEF1/LEU2 F | <u>ATG TCT GCC CCT AAG AAG ATC GTC GTT TTG CCA GGT GAC CAG</u> CTG GAG CTC ATA GCT TCA (SEQ ID NO 31) | The underlined 40 nucleotides correspond to the 40 first bp of LEU2 gene<br>20 nucleotides in bold are homologous to the 20 first bp pTEF1 |
| pTEF R | <u>TCC GGG TTG GGG TGT GCA GAT TAA AGT TGT TCA TAC TAG TGG</u> ATC CAC TAG TTC TAG AAA (SEQ ID NO 32) | The underlined 40 nucleotides correspond to the 40 first bp of yqhD*(G419E)<br>20 nucleotides bold are homologous to the 20 last bp of pTEF1 |
| yqhD/TEF-F | <u>CAT AGC AAT CTA ATC TAA GTT TTC TAG AAC TAG TGG ATC CAC</u> TAG TAT GAA CAA CTT TAA (SEQ ID NO 33) | The underlined 40 nucleotides correspond to the 40 last bp of pTEF1<br>20 nucleotides in bold are homologous to the 20 first bp yqhD*(G419E) |
| yqhD/CYCtR | <u>TGA AAT ATA AAT AAC GTT CTT AAT ACT AAC ATA ACT ATA AAC</u> TAG TTT AGC GGG CGG CTT (SEQ ID NO 34) | The underlined 40 nucleotides correspond to the 40 first bp of CYCt<br>20 nucleotides in bold are homologous to the 20 last bp of yqhD*(G419E) |
| CYCt/yqhD F | <u>TGT CAG CCG CCG TAT ATA CGA AGC CGC CCG CTA AAC TAG TTT</u> ATA GTT ATG TTA GTA TTA (SEQ ID NO 35) | The underlined 40 nucleotides correspond to the 40 last bp of yqhD*(G419E)<br>20 nucleotides in bold are homologous to the 20 first bp of CYCt |
| CYCt/Nat1R | <u>CTCCATGTCGCTGGCCGGGTGACCCGG CGGGGACGAGGCA</u>GCAAATTAAA GCCTTCGAGC (SEQ ID NO 36) | The underlined 40 nucleotides correspondto the 40 first bp of pTEF1<br>20 nucleotides in bold are homologous to the 20 last bp of CYCt |
| Nat1/CYCt F | <u>GCT TGA GAA GGT TTT GGG ACG CTC GAA GGC TTT AAT TTC CTG</u> CCT CGT CCC CGC CGG GTC (SEQ ID NO 37) | The underlined 40 nucleotides correspond to the 40 last bp of CYCt<br>20 nucleotides in bold are |

TABLE 14-continued

| Primer Name | Sequence | Description |
|---|---|---|
| | | homologous to the 20 first bp of pTEF1 |
| Nat1/Leu2 | TTA AGC AAG GAT TTT CTT AAC TTC TTC GGC GAC AGC ATC ACA GTA TAG CGA CCA GCA TTC (SEQ ID NO 38) | The underlined 40 nucleotides correspond to the 40 last bp of LEU2 gene 20 nucleotides in bold are homologous to the 20 last bp of TEF1t |
| YQHD ver F | ATG TCT GCC CCT AAG AAG ATC (SEQ ID NO 39) | 20 nucleotides homologous to the 20 first bp of LEU2 gene |
| YQHD ver R | AC TAG TTT AGC GGG CGG CTT (SEQ ID NO 40) | 20 nucleotides homologous to the 20 last bp of yqhD* (G149E) |

1-3. Construction of Two *S. cerevisiae* Strain CENPK Δgpd2, Δtpi1, gldA*(A160T), yqhD, mgsA*(H21Q) and CENPK Δgpd2, Δtpi1, gldA*(A160T), yqhD*(G149E), mgsA*(H21Q)

The two strains used was CENPK, Δgpd2, gldA*(A160T), yqhD or CENPK, Δgpd2, gldA*(A160T), yqhD*, previously built.

The gene TPI1 was inactivated by transforming the strains with a PCR fragment corresponding to a pTEF1-hph-TEF1t-pPGK1-msgA*(H21Q) cassette using the "short flanking homology" (SFH) method.

The pTEF1-hph-TEF1t-pPGK1-msgA*(H21Q) cassette was constructed using long PCR-based fusion of several fragments.

The pTEF1-hph-TEF1t-pPGK1 were amplified from the plasmid pAG35pPGK1 constructed from pAG35 (Euroscarf) using PGK1/TPI1F and PGK1/mgsAR.

mgsA*(H21Q) was amplified from pETTOPO mgsA* (H21Q) using the primers mgsA/PGK1F and mgsA/TPI R as primers.

All fragments were amplified using primers having overlapping ends as described in Table 15. Each fragment was then purified.

100 ng of each fragment was used in a PCR experiment without primers and using low annealing conditions, allowing their simultaneous fusion.

The unpurified product obtained in this step was used as a matrix in a PCR experiment at high Tm, using PGK1/TPI1F and mgsA/TPI R primers having an extension of 40 bp homologous to the 40 first and 40 last bp of the TPI1 locus (Table 15).

This fragment was integrated in the TPI1 locus, replacing TPI1 open reading frame.

The transformation method used is the lithium acetate method. The strain CENPK, Δgpd2, gldA*(A160T), yqhD and the strain CENPK, Δgpd2, gldA*(A160T), yqhD* (G149E) was transformed by pTEF1-hph-TEF1t-pPGK1-msgA*(H21Q) cassette to obtained CENPK, Δgpd2, Δtpi1, gldA*(A160T), yqhD*(G419E), msgA*(H21Q), CENPK, Δgpd2, Δtpi1, gldA*(A16 Transformants were selected on YEPD rich medium (1% bacto yeast extract, 2% bactopeptone, 2% glucose) supplemented with 250 μg/ml of hygromycin (Sigma-Aldrich).

The integration of msgA*(H21Q) was confirmed by PCR on genomic DNA extracted, using mgsA ver F and mgsA ver R primers (Table 15).

This resulted in the heterologous expression of mgsA* (H21Q) and deletion of TPI1. The resulting strains were named CENPK Δgpd2, Δtpi1, gldA*(A160T), yqhD, mgsA* (H21Q) and CENPK Δgpd2, Δtpi1, gldA*(A160T), yqhD* (G149E), mgsA*(H21Q).

TABLE 15

| Primer Name | Sequence | Description |
|---|---|---|
| PGK1/TPI1F | ATG TCC AAA GCT ACA TAT AAG GAA CGT GCT GCT ACT CAT CGC CAG ATC TGT TTA GCT TGC (SEQ ID NO 41) | The underlined 40 nucleotides correspond to the 40 first bp of TPI1 gene 20 nucleotides in bold are homologous to 20 the first bp pTEF1 |
| PGK1/mgsAR | GTG CGA GTC GTC AGT TCC ATA ATA CGC AAA CCG CCT CTC C (SEQ ID NO 42) | The underlined 21 nucleotides correspond to the 40 first bp of msgA*(H21Q) 19 nucleotides in bold are homologous to 20 the last bp of pPGK1 |
| mgsA/PGK1F | GGA GAG GCG GTT TGC GTA TTA TGG AAC TGA CGA CTC GCA C (SEQ ID NO 43) | The underlined 22 nucleotides correspond to the 40 last bp of pPGK1 18 nucleotides in bold are homologous to the 20 first bp of msgA*(H21Q) |
| mgsA/TPI R | TTA GTT TTC CTG GCC GCA TCT TCT CAA ATA TGC TTC CCT TTA CTT CAG ACG GTC CGC GAG (SEQ ID NO 44) | The underlined 40 nucleotides correspond to the 40 last bp of TPI1 20 nucleotides in bold are homologous to the 20 last bp of msgA*(H21Q) |

TABLE 15-continued

| Primer Name | Sequence | Description |
|---|---|---|
| mgsA ver F | GG AAC TGA CGA CTC GCA C (SEQ ID NO 45) | 20 nucleotides homologous to the 20 first bp of TPI1 gene |
| mgsA ver R | TTAGTTTCTAGAGTTGATGA (SEQ ID NO 46) | 20 nucleotides homologous to the 20 last bp of msgA*(H21Q) |

2—Assessment of 1,2-propanediol Production in *S. cerevisiae* CENPK Δgpd2, Δtpi1, gldA*(A160T), yqhD, mgsA*(H21Q)

The strain CENPK, Δgpd2, Δtpi1, gldA*(A160T), yqhD, msgA*(H21Q) described above and the control strain CEN.PK2-1C were cultivated in batch culture, under anaerobic or aerobic conditions in minimal medium (SD medium 0.67% of Yeast nitrogen base without amino acid (DIFCO)) containing either 5% of glucose or 5% of sucrose as sole carbon source. Minimal medium was supplemented with 50 mg/l of uracil, 250 mg/l of leucine, 50 mg/L of histidine and 50 mg/L of tryptophan. Cultures were performed at 28° C. under agitation at 225 rpm.

Aerobic cultures were carried out in shake flask of 250 ml containing 50 ml of medium. Anaerobic cultures were carried out in penicillin flask of 100 ml containing 90 ml of medium.

At the end of the culture, 1,2-propanediol in the fermentation broth were analysed by gas chromatography/mass spectrometry (GC/MS) with an Agilent 7890A Series gas chromotograph coupled to an Agilent 5975C Series mass selective detector (EI) and a HP INNOWax column. The retention time and mass spectrum of 1,2-propanediol generated were compared to those of authentic 1,2-propanediol. Residual glucose or sucrose in the fermentation broth were analysed by HPLC using a Biorad HPX 97H column for the separation and a refractometer for the detection. The yields of 1,2-propanediol over glucose or sucrose were then calculated.

TABLE 16 production of 1,2-propanediol in minimal medium in aerobic or anaerobic conditions with glucose or sucrose as carbon source.

| Strain | Condition | Carbon source | 1,2-propanediol titer (mg/l) | 1,2-propanediol yield (mg/g carbon source) |
|---|---|---|---|---|
| CEN.PK2-1C | aerobic culture | glucose | 44 | 0.9 |
| CENPK, Δgpd2, Δtpi1, gldA*(A160T), yqhD, msgA*(H21Q) | aerobic culture | glucose | 75 | 1.6 |
| CEN.PK2-1C | aerobic culture | sucrose | 41 | 0.9 |
| CENPK, Δgpd2, Δtpi1, gldA*(A160T), yqhD, msgA*(H21Q) | aerobic culture | sucrose | 69 | 1.6 |
| CEN.PK2-1C | anaerobic culture | glucose | 11 | 0.2 |
| CENPK, Δgpd2, Δtpi1, gldA*(A160T), yqhD, msgA*(H21Q) | anaerobic culture | glucose | 44 | 0.9 |

The production of 1,2-propanediol in a *S. cerevisiae* strain with a mutant GlyDH was improved under anaerobic or aerobic conditions with glucose or sucrose as compared with the non-modified control strain.

REFERENCES

Asnis R E and Broadie A F (1953), *J. Biol. Chem.* 203: 153-159

McGregor W G, Philips J, Suelter C H (1974), *J. Biol. Chem.* 249: 3132-3139

Nishise H, Nagao A, Tani Y, Yamada H (1984), *Agric. Biol. Chem.* 48: 1603-1609

Spencer P, Brown K J, Scawen M D, Atkinson T, Gore M G (1989), *Biochim. Biophys. Acta.* 994: 270-279

Ruzheinikov S N, Burke J, Sedelnikova S, Baker P J, Taylor R, Bullough P A, Muir N M, Gore M G, Rice D W (2001), *Structure* 9: 789-802

Mallinder P R, Pritchard A, Moir A (1991), *Gene* 110: 9-16

Truniger V and Boos W (1994), *J. Bacteriol.* 176: 1796-1800

Kelley J J and Decker E E (1984), *J. Biol. Chem.* 259: 2124-2129

Tang C T, Ruch F E Jr, Lin C C (1979), *J. Bacteriol.* 140: 182-187

Lee L G and Whitesides G M (1985), *J. Org. Chem.* 51: 25-36

Subedi K P, Kim I, Kim J, Min B, Park C (2007), *FEMS Microbiol. Lett.* 279: 180-187

Altaras N E and Cameron D C (1999), *Appl. Environ. Microbiol.* 65: 1180-1185

Cooper R A (1984), *Annu. Rev. Microbiol.* 38: 49-68 *Arch. Microbiol.* 170: 209-219

Tötemeyer S, Booth N A, Nichols W W, Dunbar B, Booth I R (1998), *Mol. Microbiol.* 27: 553-562

Ferguson G P, Tötemeyer S, MacLean M J, Booth I R (1998), *Arch. Microbiol.* 170: 209-218

Misra K, Banerjee A R, Ray S, Ray M (1995), *Biochem. J.* 305: 999-1003

Cameron D C, Altaras N E, Hoffman M L, Shaw A J (1998), *Biotechnol. Prog.* 14: 116-125

Bennett G N and San K Y, (2001), *Appl. Microbiol. Biotechnol.* 55: 1-9

Ko J, Kim I, Yoo S, Min B, Kim K, Park C (2005), *J. Bacteriol.* 187: 5782-578

The UniProt consortium, (2008), *Nucleic Acids Res.* 36: D190-195

Guldener, U., et al., (1996), *Nucleic Acids Res.* 24: 2519-24

Schiestl, R. H. and Gietz, R. D., (1989), *Curr Genet.* 16: 339-46.

Shevchuk, N. A., et al., (2004), *Nucleic Acids Res.* 32: e19

The invention claimed is:

1. A mutant bacterial glycerol dehydrogenase (GlyDH) enzyme, wherein unmutated GlyDH enzyme from *E.coli* comprises at least one amino acid sequence selected from the group consisting of:
   (a) an amino acid sequence consisting of a Conserved Region 1 (CR1): -Pro-Thr-X1-X2-X3-X4-X5-X6-X7-X8-X9-(CR1)
   Wherein X1 is Ile,
   X2 is Ala,
   X3 is Ser,
   X4 is Thr,
   X5 is Asp,
   X6 is Ala,
   X7 is Pro,
   X8 is Cys, and
   X9 is Ser; and
   (b) an amino acid sequence consisting of a Conserved Region 2 (CR2): -X10-X11-X12-X13-X14-X15-X16-X17-X18-X19-X20-Gly-X21-X22-Asp (CR2) wherein
   X10 is Val,
   X11 is Ala,
   X12 is Gly,
   X13 is Ala,
   X14 is Pro,
   X15 is Ala,
   X16 is Arg,
   X17 is Leu,
   X18 is Leu,
   X19 is Ala,
   X20 is Ala,
   X21 is Ile, and
   X22 is Gly,
   wherein said unmutated GlyDH enzyme comprises an amino acid substitution at amino acid X4 in CR1 and/or an amino acid substitution at amino acid X13 in CR2, and wherein inhibition of said mutant GlyDH enzyme activity by NAD$^+$and/or by enzyme's substrate and/or by enzyme's product are reduced compared to the unmutated parent GlyDH enzyme.

2. The mutant bacterial glycerol dehydrogenase GlyDH enzyme of claim 1, wherein said mutant GlyDH enzyme comprises the conserved regions CR1 and/or CR2, wherein each of said CR1 and CR2 comprises said substitution, and wherein CR1 consists of Pro Thr The Ala Ser Asn Asp Ala Pro Cys Ser, and CR2 consists of Val Ala Gly Thr Pro Ala Arg Leu Leu Ala Ala Gly Ile Gly Asp.

3. The mutant bacterial GlyDH enzyme of claim 1, wherein said mutant GlyDH enzyme comprises the sequence selected from the group consisting of SEQ ID NO:1 and SEQ ID NO: 2.

4. A method for production of 1,2-propanediol, comprising: culturing a bacterium comprising the mutant GlyDH enzyme of claim 1 for an improved production of said 1,2-propanediol in an appropriate culture medium and recovering a 1,2-propanediol wherein said improved production is compared to the production of 1,2-propanediol in the bacterium which does not comprise the mutant GlyDH enzyme.

5. The method of claim 1, wherein said mutant bacterial GlyDH enzyme of claim 1 comprises the conserved regions CR1 and/or CR2, wherein said CR1 or CR2 comprises said substitution, and wherein CR1 consists of Pro Thr Ile Ala Ser Asn Asp Ala Pro Cys Ser, and CR2 consists of Val Ala Gly Thr Pro Ala Arg Leu Leu Ala Ala Gly Ile Gly Asp, respectively.

6. The method of claim 1, wherein the mutant GlyDH enzyme comprises the sequence selected from the group consisting of SEQ ID NO: 1 and SEQ ID NO: 2.

7. The method of claim 1, wherein said microorganism is *E. coli*.

8. The method of claim 1, wherein said 1,2-propanediol is purified.

9. The method of claim 1, wherein said appropriate culture medium comprises at least one carbon source selected from the group consisting of glucose, sucrose, mono- or disaccharides, starch and derivatives thereof.

10. The method of claim 9, wherein said carbon source is selected from the group consisting of glucose and sucrose.

11. The method of claim 1, wherein said production comprises a batch, fed-batch or continuous process.

* * * * *